United States Patent
Suzuki

(10) Patent No.: US 11,397,314 B2
(45) Date of Patent: Jul. 26, 2022

(54) ENDOSCOPE SYSTEM, OPTICAL ADAPTOR FOR ENDOSCOPE, AND METHOD OF CONTROLLING ENDOSCOPE SYSTEM

(71) Applicant: OLYMPUS CORPORATION, Tokyo (JP)

(72) Inventor: Shinpei Suzuki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 287 days.

(21) Appl. No.: 16/903,467

(22) Filed: Jun. 17, 2020

(65) Prior Publication Data
US 2020/0310101 A1 Oct. 1, 2020

Related U.S. Application Data

(63) Continuation of application No. PCT/JP2018/047794, filed on Dec. 26, 2018.

(30) Foreign Application Priority Data

Dec. 27, 2017 (JP) .............................. JP2017-250403

(51) Int. Cl.
*G02B 23/24* (2006.01)
*G01N 21/954* (2006.01)
*A61B 1/00* (2006.01)

(52) U.S. Cl.
CPC ...... *G02B 23/2407* (2013.01); *A61B 1/00163* (2013.01); *A61B 1/00183* (2013.01); *G01N 21/954* (2013.01); *G01N 2201/062* (2013.01); *G01N 2201/0612* (2013.01); *G01N 2201/0638* (2013.01); *G01N 2201/0648* (2013.01)

(58) Field of Classification Search
CPC ............................ G02B 23/24; A61B 1/00163
See application file for complete search history.

(56) References Cited

U.S. PATENT DOCUMENTS 8,876,706 B2 * 11/2014 Mizuyoshi ........... A61B 1/0684
600/109

FOREIGN PATENT DOCUMENTS

| EP | 2 666 401 A1 | 11/2013 |
| EP | 3 017 747 A1 | 5/2016 |
| JP | H09-248276 A | 9/1997 |
| JP | 2001-137186 A | 5/2001 |

(Continued)

OTHER PUBLICATIONS

International Search Report dated Apr. 9, 2019 issued in International Application No. PCT/JP2018/047794.

*Primary Examiner* — Rebecca C Bryant
(74) *Attorney, Agent, or Firm* — Scully, Scott, Murphy & Presser, P.C.

(57) ABSTRACT

In an endoscope system, a first actuator is configured to move a first optical member when a control signal is applied to the first actuator. A second actuator is configured to move a second optical member only when the control signal having a signal value greater than or equal to a predetermined value is applied to the second actuator. A signal source is configured to apply the control signal having the signal value greater than or equal to the predetermined value or the control signal having a signal value less than the predetermined value to the first actuator and is configured to apply the control signal having the signal value greater than or equal to the predetermined value to the second actuator.

18 Claims, 33 Drawing Sheets

(56) References Cited

FOREIGN PATENT DOCUMENTS

| | | |
|---|---|---|
| JP | 2014-023776 A | 2/2014 |
| JP | 2014-028008 A | 2/2014 |
| WO | 2013/042647 A | 3/2013 |
| WO | 2015/001852 A1 | 1/2015 |
| WO | 2016/170568 A1 | 10/2016 |

\* cited by examiner

FIG. 18A
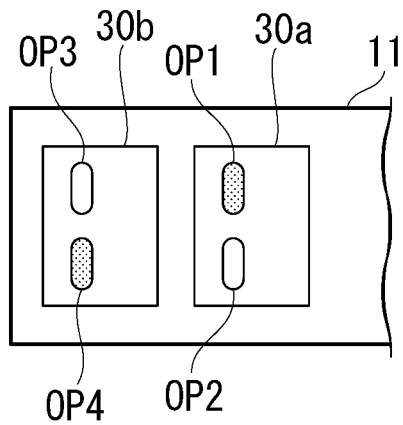
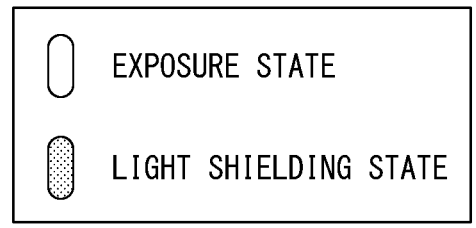
FIG. 18B
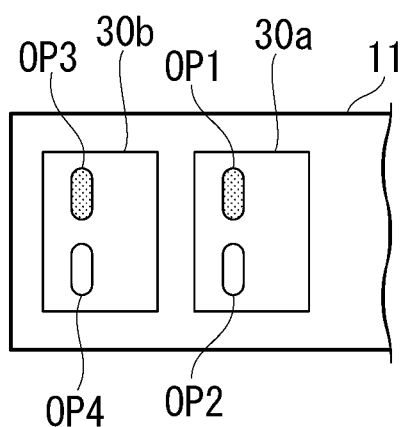
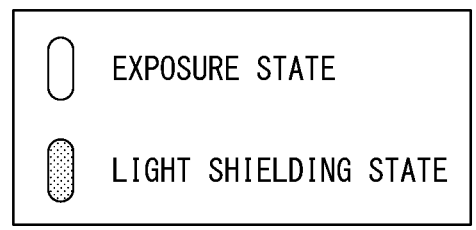
FIG. 18C
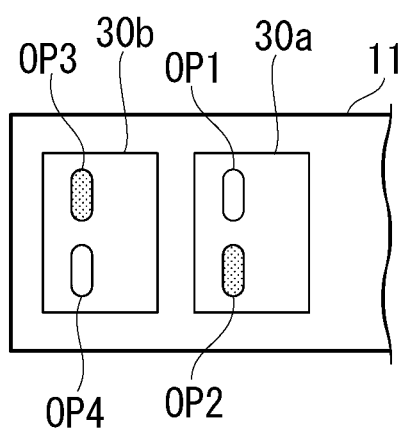
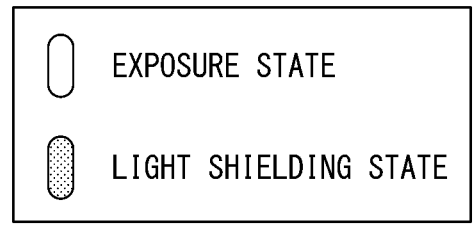

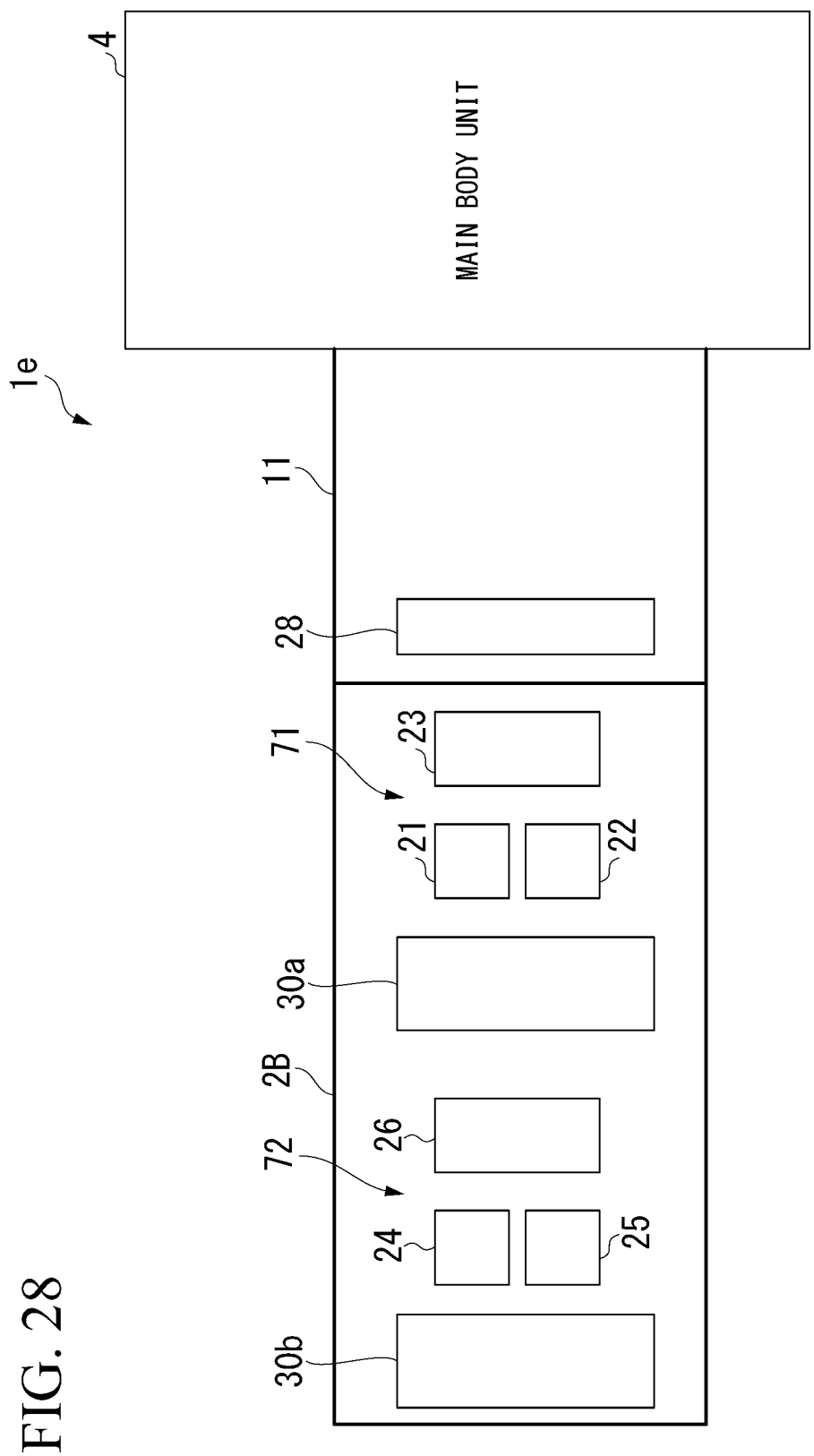

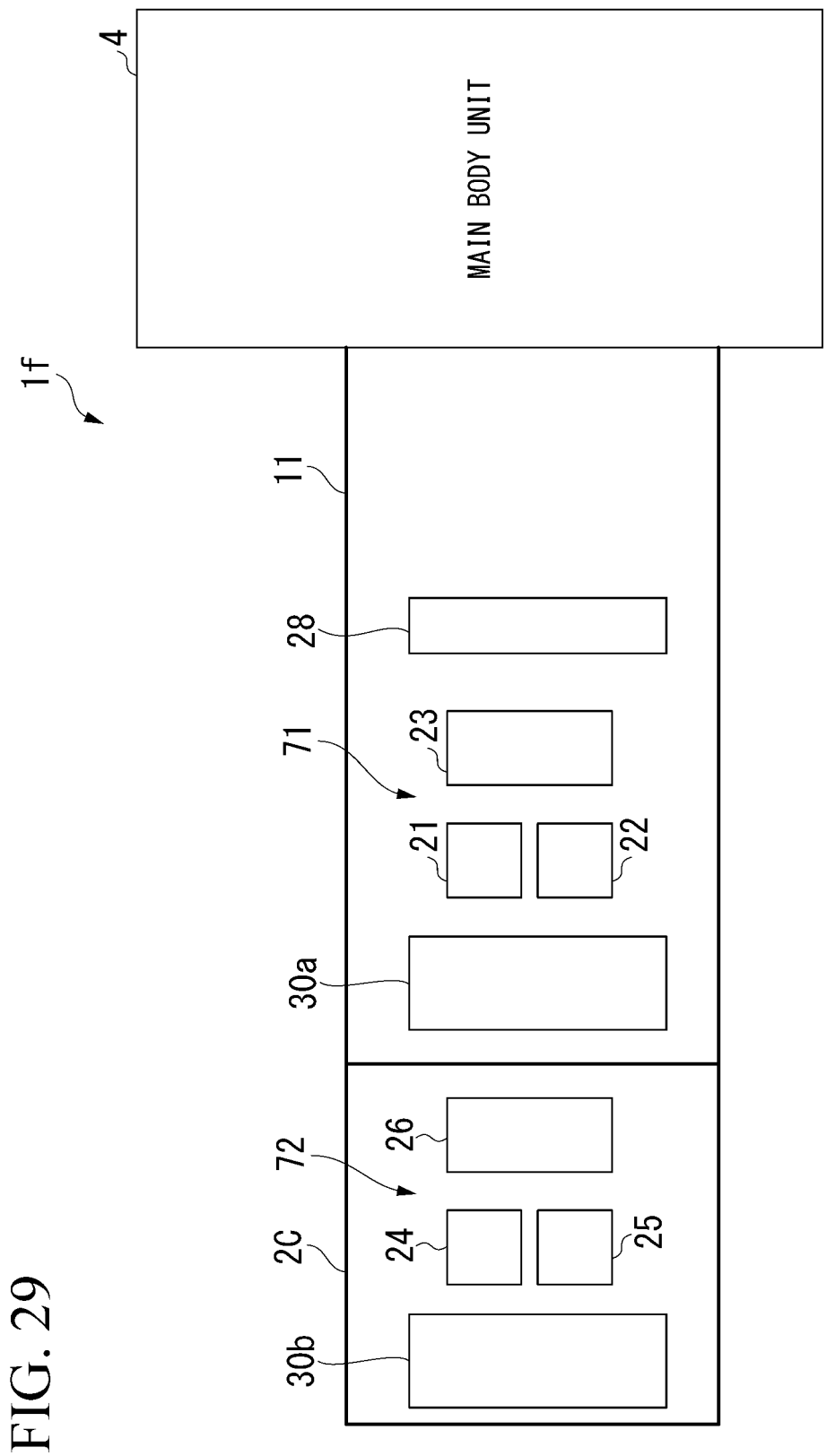

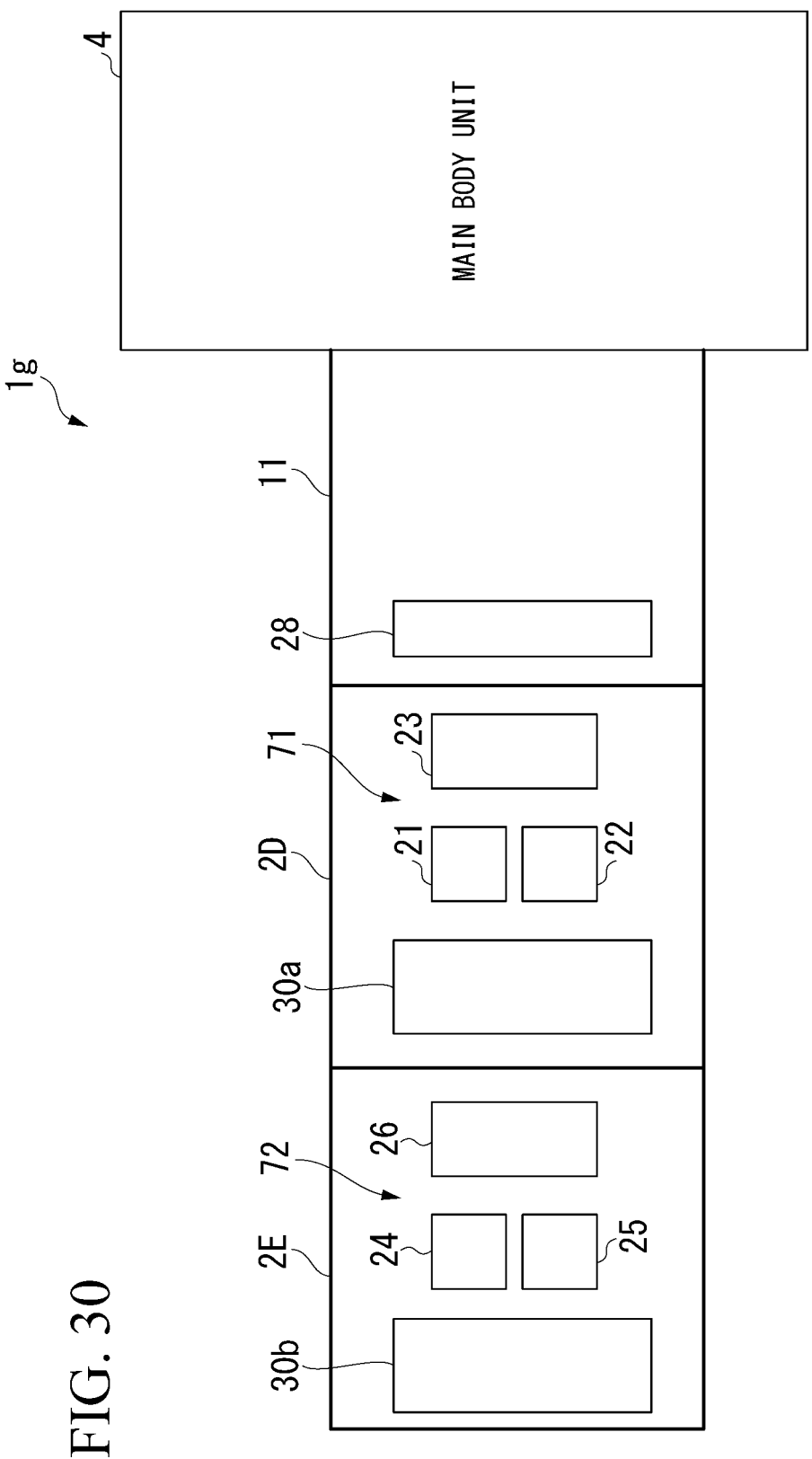

RELATED ART

RELATED ART

RELATED ART

RELATED ART

ENDOSCOPE SYSTEM, OPTICAL ADAPTOR FOR ENDOSCOPE, AND METHOD OF CONTROLLING ENDOSCOPE SYSTEM

The present application claims priority to Japanese Patent Application No. 2017-250403, filed on Dec. 27, 2017 and is a continuation application based on PCT Patent Application No. PCT/JP2018/047794, filed on Dec. 26, 2018, and the content of both the Japanese patent application and the PCT patent application is incorporated herein by reference.

BACKGROUND OF THE INVENTION

Field of the Invention

The present invention relates to an endoscope system, an optical adaptor for an endoscope, and a method of controlling an endoscope system.

Description of Related Art

Industrial endoscopes have been used for observation and inspection of internal damage, corrosion, and the like of boilers, pipes, and the like. An optical adaptor that is a lens unit for changing optical characteristics is used in an industrial endoscope. An industrial endoscope includes an insertion unit to be inserted into the inside of an object. The insertion unit and the optical adaptor are designed such that it is possible to attach the optical adaptor to the insertion unit and detach the optical adaptor from the insertion unit.

An optical adaptor of a type that is in accordance with usage and conditions of inspection is used. For this reason, an industrial endoscope is able to acquire an optimal image. For example, an industrial endoscope is able to acquire a direct-view image, a side-view image, an image for which the focus is close to a near point, an image for which the focus is close to a distant point, and the like. There are cases in which a plurality of lenses are disposed in an optical adaptor in order to enable an industrial endoscope to acquire a left image and a right image having the parallax therebetween. In such cases, an industrial endoscope is able to measure the dimension of a subject by using the principle of triangulation.

There are many cases in which an actuator called a micro magnetic actuator is mounted in industrial endoscopes that have been developed in recent years in order to switch optical characteristics inside an optical adaptor. A shutter for switching lenses and optical paths inside an optical adaptor moves by using an actuator. An industrial endoscope is able to switch a plurality of types of images by controlling movement of the shutter. For example, the industrial endoscope is able to switch between a near point and a distant point, direct view and side view, left and right, and the like. For this reason, it is unnecessary to exchange optical adaptors.

An endoscope device including an actuator unit is disclosed in PCT International Publication No. WO2015/001852. In PCT International Publication No. WO2015/001852, optical paths are switched when an actuator moves a shutter. An actuator is a driving mechanism using a coil and a magnet. Such technology is used as a driving mechanism of a lens mounted in cameras, optical storage devices, and the like. The direction and amount of driving force are controlled in accordance with the direction and amount of current applied to a coil.

Hereinafter, usefulness of switching optical characteristics will be described. An inspector inserts an endoscope into an object until the tip end of the endoscope reaches an observation part in order to inspect structures of an engine, a pipe, and the like by using the endoscope. An inspector performs observation, inspection, measurement, and the like of damage, dirt, and the like. An image suitable for insertion operation is not always an image suitable for observation or the like. In an image suitable for insertion operation, a wide range is often bright and the resolution may be low. In an image suitable for observation or the like, the resolution of a range close to a subject is often high and a wide range is not necessarily bright. Sometimes observation of a subject facing the side of an insertion unit is necessary.

An inspector generally needs to deal with such a wide variety of situations. In other words, an inspector needs to retrieve an endoscope that has been inserted into an object, exchange optical adaptors, and thereafter insert the endoscope into the object again. In a case in which an optical adaptor for measurement is used, an inspector needs to perform insertion operation or the like while monitoring one of two images corresponding to left and right regions of a light receiving surface of an imaging device. For this reason, the operation is difficult. In such a situation, it is desirable that a control unit in a main body of a device switch optical characteristics of an optical adaptor. In this way, the workload of insertion work and exchange work of an optical adaptor is reduced. As a result, it is possible to significantly reduce the complexity of inspection work.

In the endoscope device disclosed in PCT International Publication No. WO2015/001852, one actuator is disposed at the tip end of an insertion unit. One actuator is able to switch up to two types of optical characteristics, but is unable to switch, for example, four types of optical characteristics. For example, in a case in which it is necessary to switch between a near point and a distant point and switch direct view and side view, it is necessary to exchange an optical adaptor capable of switching between a near point and a distant point for an optical adaptor capable of switching between direct view and side view.

In order to make exchanging optical adaptors unnecessary, it may be effective to increase the number of mounted actuators. As the number of actuators increases, the number of types of optical characteristics that can be switched increases. For example, in a case in which two actuators are mounted, exchanging optical adaptors is unnecessary and it is possible to switch four types of optical characteristics. For example, one of the two actuators is able to switch between a near point and a distant point, and the other of the two actuators is able to switch between direct view and side view.

As described above, as the number of mounted actuators increases, more types of optical characteristics can be switched. As a result, it is possible to further reduce the workload of exchange work of an optical adaptor.

Hereinafter, a configuration and an operation of an endoscope device in which a plurality of actuators are mounted at the tip end of an insertion unit will be described. FIG. 32 shows a configuration of an endoscope device 101 in which two actuators are mounted. As shown in FIG. 32, the endoscope device 101 includes an insertion unit 111, a main body unit 104, and a light source 110.

The insertion unit 111 includes optical systems 121 to 126, an imaging device 128, a first actuator 130a, and a second actuator 130b. These configurations are disposed at the tip end of the insertion unit 111. The optical systems 121 to 126, the first actuator 130a, and the second actuator 130b are disposed optically in front of the imaging device 128. The main body unit 104 is disposed on the base end side of the insertion unit 111.

The optical systems 121 to 126 are disposed between a subject OB11 and the imaging device 128. The subject OB11 is away from the tip end of the insertion unit 111 in the optically forward direction of the insertion unit 111. The optical system 124, the optical system 125, and the optical system 126 are disposed between the first actuator 130a and the second actuator 130b. The optical system 124, the optical system 125, and the optical system 126 are optical members of a second imaging optical system 172. A shutter of the second actuator 130b is also the optical member of the second imaging optical system 172.

The optical system 121, the optical system 122, and the optical system 123 are disposed between the first actuator 130a and the imaging device 128. The optical system 121, the optical system 122, and the optical system 123 are optical members of a first imaging optical system 171. A shutter of the first actuator 130a is also the optical member of the first imaging optical system 171. For example, the optical systems 121 to 126 are lenses. The optical systems 121 to 126 form an optical image of the subject OB11 on a light receiving surface of the imaging device 128.

The first actuator 130a includes a first opening OP11 and a second opening OP12. The shutter disposed inside the first actuator 130a covers any one of the first opening OP11 and the second opening OP12. Light is not able to pass through the opening covered by the shutter. In other words, light from the subject OB11 passes through only any one of the first opening OP11 and the second opening OP12.

The second actuator 130b includes a third opening OP13 and a fourth opening OP14. The shutter disposed inside the second actuator 130b covers any one of the third opening OP13 and the fourth opening OP14. Light is not able to pass through the opening covered by the shutter. In other words, light from the subject OB11 passes through only any one of the third opening OP13 and the fourth opening OP14.

The optical system 124 is disposed at a position corresponding to the third opening OP13. Light passing through the third opening OP13 is incident to the optical system 124. The optical system 125 is disposed at a position corresponding to the fourth opening OP14. Light passing through the fourth opening OP14 is incident to the optical system 125. Light passing through the optical system 124 or the optical system 125 is incident to the optical system 126. Light passing through the optical system 126 reaches the first opening OP11 and the second opening OP12. In the example shown in FIG. 32, the state in which the fourth opening OP14 is shielded from light and the third opening OP13 is exposed to light is shown.

The optical system 121 is disposed at a position corresponding to the first opening OP11. Light passing through the first opening OP11 is incident to the optical system 121. The optical system 122 is disposed at a position corresponding to the second opening OP12. Light passing through the second opening OP12 is incident to the optical system 122. Light passing through the optical system 121 or the optical system 122 is incident to the optical system 123. Light passing through the optical system 123 is incident to the imaging device 128. The imaging device 128 generates an imaging signal in accordance with the incident light. In the example shown in FIG. 32, the state in which the first opening OP11 is shielded from light and the second opening OP12 is exposed to light is shown.

The light source 110 is connected to the main body unit 104. The light source 110 generates illumination light emitted to the subject OB11.

The main body unit 104 includes a control unit 129 and an operation unit 104a. The control unit 129 controls the light source 110 and the imaging device 128. In addition, the control unit 129 generates a control signal. The imaging device 128 is electrically connected to the control unit 129 by a signal line 155. The imaging device 128 outputs an imaging signal to the signal line 155. The signal line 155 transfers the imaging signal output from the imaging device 128 to the control unit 129.

The control unit 129 is electrically connected to a signal line 151, a signal line 152, a signal line 153, and a signal line 154. The signal line 151, the signal line 152, the signal line 153, and the signal line 154 are disposed inside the insertion unit 111. The signal line 151 and the signal line 153 are electrically connected to the first actuator 130a. The signal line 152 and the signal line 154 are electrically connected to the second actuator 130b.

The control unit 129 applies a first control signal to the first actuator 130a by outputting the first control signal to the signal line 151. The first control signal applied to the first actuator 130a is output to the signal line 153. The control unit 129 applies a second control signal to the second actuator 130b by outputting the second control signal to the signal line 152. The second control signal applied to the second actuator 130b is output to the signal line 154.

The first actuator 130a to which the first control signal in a +direction having a signal value greater than or equal to a predetermined value is applied moves the shutter to a position to cover the second opening OP12. In addition, the first actuator 130a to which the first control signal in a −direction having a signal value greater than or equal to a predetermined value is applied moves the shutter to a position to cover the first opening OP11.

The second actuator 130b to which the second control signal in the +direction having a signal value greater than or equal to a predetermined value is applied moves the shutter to a position to cover the fourth opening OP14. In addition, the second actuator 130b to which the second control signal in the −direction having a signal value greater than or equal to a predetermined value is applied moves the shutter to a position to cover the third opening OP13.

A user is able to specify a position of the shutter of each of the first actuator 130a and the second actuator 130b by operating the operation unit 104a disposed in the main body unit 104. In other words, a user is able to input an instruction for switching optical characteristics. When a user inputs the instruction by operating the operation unit 104a, the instruction is input to the control unit 129. The control unit 129 outputs a control signal in accordance with the instruction.

FIG. 33 shows an equivalent circuit of the first actuator 130a and the second actuator 130b. The first actuator 130a and the second actuator 130b are electromagnetic actuators. The first actuator 130a is equivalent to a circuit in which a coil L11 and a resistor R11 are connected in series to each other. The second actuator 130b is equivalent to a circuit in which a coil L12 and a resistor R12 are connected in series to each other. The first actuator 130a and the second actuator 130b are connected in parallel to the control unit 129.

FIGS. 34A to 34D show four types of optical characteristics that the endoscope device 101 is able to switch. In FIGS. 34A to 34D, the optical systems 121 to 126 are not shown. The endoscope device 101 is able to switch optical paths within the imaging optical systems by switching the optical characteristics. In other words, the endoscope device 101 is able to switch light beams incident to the imaging device 128.

FIG. 34A shows first optical characteristics. The shutter of the first actuator 130*a* covers the second opening OP12 and the shutter of the second actuator 130*b* covers the fourth opening OP14. For this reason, light emitted from the subject OB11 passes through the third opening OP13 and the first opening OP11.

FIG. 34B shows second optical characteristics. The shutter of the first actuator 130*a* covers the first opening OP11 and the shutter of the second actuator 130*b* covers the fourth opening OP14. For this reason, light emitted from the subject OB11 passes through the third opening OP13 and the second opening OP12.

FIG. 34C shows third optical characteristics. The shutter of the first actuator 130*a* covers the second opening OP12 and the shutter of the second actuator 130*b* covers the third opening OP13. For this reason, light emitted from the subject OB11 passes through the fourth opening OP14 and the first opening OP11.

FIG. 34D shows fourth optical characteristics. The shutter of the first actuator 130*a* covers the first opening OP11 and the shutter of the second actuator 130*b* covers the third opening OP13. For this reason, light emitted from the subject OB11 passes through the fourth opening OP14 and the second opening OP12.

As described above, optical systems through which light emitted from the subject OB11 passes are different in accordance with the positions of the shutters of the first actuator 130*a* and the second actuator 130*b*. In the examples shown in FIGS. 34A to 34D, four patterns of optical paths through which light emitted from the subject OB11 passes are shown. It is possible to switch the first to the fourth optical characteristics by switching the positions of the shutters of the first actuator 130*a* and the second actuator 130*b*.

FIG. 35 shows a procedure of an operation of the endoscope device 101. In FIG. 35, an operation of the endoscope device 101 is shown when the optical characteristics of the endoscope device 101 are switched from the second optical characteristics shown in FIG. 34B to the third optical characteristics shown in FIG. 34C.

Before the processing shown in FIG. 35 is executed, the shutter of the first actuator 130*a* covers the first opening OP11 and the shutter of the second actuator 130*b* covers the fourth opening OP14. When a user inputs an instruction for switching optical characteristics through the operation unit 104*a*, switching of the optical characteristics is executed. The operation unit 104*a* outputs the instruction input by a user to the control unit 129. At this time, the control unit 129 accepts an instruction for switching to the third optical characteristics (Step S1000).

After Step S1000, the control unit 129 outputs a control signal in the +direction having a predetermined signal value to the signal line 151. In this way, the control unit 129 applies the control signal to the first actuator 130*a* (Step S1010).

After Step S1010, the control unit 129 outputs a control signal in the −direction having a predetermined signal value to the signal line 152. In this way, the control unit 129 applies the control signal to the second actuator 130*b* (Step S1020).

FIG. 36A shows a waveform of the control signal applied to the first actuator 130*a* in Step S1010. FIG. 36B shows a waveform of the control signal applied to the second actuator 130*b* in Step S1020. The horizontal axis in each drawing represents time and the vertical axis in each drawing represents current.

As shown in FIG. 36A, the signal value of the control signal is H111 and the duration during which the control signal is applied to the first actuator 130*a* is T111. As shown in FIG. 36B, the signal value of the control signal in the −direction is H112 and the duration during which the control signal is applied to the second actuator 130*b* is T111. The signal value H111 represents a signal value in the +direction. The signal value H112 represents a signal value in the −direction. The sizes of the signal value H111 and the signal value H112 are the same.

The shutter of the first actuator 130*a* to which the control signal is applied in Step S1010 moves to a position to cover the second opening OP12. The shutter of the second actuator 130*b* to which the control signal is applied in Step S1020 moves to a position to cover the third opening OP13. According to the operation shown in FIG. 35, the optical characteristics of the endoscope device 101 are switched from the second optical characteristics to the third optical characteristics specified by a user.

In this way, when a user inputs the instruction for switching optical characteristics through the operation unit 104*a*, the control signal in accordance with the instruction is applied to the first actuator 130*a* or the second actuator 130*b*. Consequently, the optical characteristics of the endoscope device 101 are switched to the desired optical characteristics.

The signal line 151 to which the control signal is output in Step S1010 and the signal line 152 to which the control signal is output in Step S1020 are different from each other. For this reason, the first actuator 130*a* and the second actuator 130*b* are able to operate independently of each other. The order in which the two control signals are output to the signal line 151 and the signal line 152 is not limited to the order shown in FIG. 35. The two control signals may be simultaneously applied to the signal line 151 and the signal line 152.

An example of an endoscope device in which two actuators are mounted is described in the above. Three or more actuators may be mounted in an endoscope device. Each of the actuators is connected to the control unit 129 by two signal lines. In the example shown in FIG. 32, the first actuator 130*a* is connected to the control unit 129 by the signal line 151 and the signal line 153. In addition, the second actuator 130*b* is connected to the control unit 129 by the signal line 152 and the signal line 154.

When switching of the optical characteristics is executed, the control unit 129 outputs a control signal to a signal line connected to each actuator. The direction (polarity) of the control signal applied to each actuator is a direction (polarity) for which the position of the shutter of each actuator becomes the desired position. The signal value of the control signal applied to each actuator is greater than or equal to a predetermined signal value.

When it is assumed that the number of actuators mounted in an endoscope device is N, the number of optical characteristics that the endoscope device is able to switch is two to the power of N. The number N is a natural number of two or more. For example, in a case in which three actuators are mounted in an endoscope device, the endoscope device is able to switch eight types of optical characteristics.

SUMMARY OF THE INVENTION

According to a first aspect of the present invention, an endoscope system includes a first optical member, a second optical member, a first actuator capable of controlling the first optical member, a second actuator capable of controlling the second optical member, and a signal source configured to output a control signal to the first actuator and the second actuator. The first actuator and the second actuator are electrically connected to the signal source. The first actuator is configured to move the first optical member when the control signal is applied to the first actuator. The second actuator is configured to move the second optical member only when the control signal having a signal value greater than or equal to a predetermined value is applied to the second actuator. The signal source is configured to apply the control signal having the signal value greater than or equal to the predetermined value or the control signal having a signal value less than the predetermined value to the first actuator and is configured to apply the control signal having the signal value greater than or equal to the predetermined value to the second actuator.

According to a second aspect of the present invention, in the first aspect, the signal source may be configured to apply the control signal having the signal value less than the predetermined value to the first actuator and the second actuator after the signal source applies the control signal having the signal value greater than or equal to the predetermined value to the first actuator and the second actuator.

According to a third aspect of the present invention, in the first aspect, the first actuator and the second actuator may be electromagnetic actuators. The first optical member may be a shutter or a prism. The second optical member may be a shutter different from the first optical member in a case in which the first optical member may be a shutter. The second optical member may be a prism different from the first optical member in a case in which the first optical member is a prism.

According to a fourth aspect of the present invention, in the first aspect, the first actuator may include a first coil that generates a magnetic force acting on the first optical member when the control signal is applied to the first actuator. The second actuator may include a second coil that generates a magnetic force acting on the second optical member when the control signal is applied to the second actuator. A number of turns of the first coil may be greater than a number of turns of the second coil.

According to a fifth aspect of the present invention, in the first aspect, the first actuator may include a first permanent magnet fixed to the first optical member. The second actuator may include a second permanent magnet fixed to the second optical member. A magnetic force of the first optical member may be stronger than a magnetic force of the second permanent magnet.

According to a sixth aspect of the present invention, in the first aspect, the first actuator may include a first magnetic substance and a first coil. The first coil may be wound around the first magnetic substance and may beconfigured to cause the first magnetic substance to be magnetized when the control signal is applied to the first actuator. The second actuator may include a second magnetic substance and a second coil. The second coil may be wound around the second magnetic substance and may be configured to cause the second magnetic substance to be magnetized when the control signal is applied to the second actuator. A magnetic force generated in the first magnetic substance when the first magnetic substance is magnetized may be stronger than a magnetic force generated in the second magnetic substance when the second magnetic substance is magnetized.

According to a seventh aspect of the present invention, in the first aspect, the endoscope system may further include a signal line connecting the first actuator and the second actuator to the signal source. The first actuator and the second actuator may be connected in parallel to the signal line. The second actuator may include a resistor electrically connected to the signal line.

According to an eighth aspect of the present invention, in the first aspect, the endoscope system may further include a resistor and a signal line connecting the first actuator and the second actuator to the signal source. The first actuator and the second actuator may be connected in parallel to the signal line. The resistor may be connected in series to the second actuator and electrically connected to the signal line.

According to a ninth aspect of the present invention, in the first aspect, the endoscope system may further include a signal line connecting the first actuator and the second actuator to the signal source and may further include a first resistor and a second resistor. The first actuator and the second actuator may be connected in parallel to the signal line. The first resistor may be connected in series to the first actuator and electrically connected to the signal line. The second resistor may be connected in series to the second actuator and electrically connected to the signal line.

According to a tenth aspect of the present invention, in the first aspect, the first actuator may be configured to move the first optical member when the control signal is continuously applied to the first actuator for longer than or equal to a first application duration. The second actuator may be configured to move the second optical member only when the control signal having the signal value greater than or equal to the predetermined value is continuously applied to the second actuator for longer than or equal to a second application duration. The first application duration may be longer than the second application duration. The signal source may be configured to continuously apply the control signal having the signal value greater than or equal to the predetermined value to the first actuator and the second actuator for longer than or equal to the second application duration and shorter than the first application duration. The signal source may be configured to continuously apply the control signal having the signal value less than the predetermined value to the first actuator and the second actuator for longer than or equal to the first application duration.

According to an eleventh aspect of the present invention, in the tenth aspect, a timing at which the control signal having the signal value greater than or equal to the predetermined value is applied to the first actuator and the second actuator may be different from a timing at which the control signal having the signal value less than the predetermined value is applied to the first actuator and the second actuator.

According to a twelfth aspect of the present invention, in the tenth aspect, the first actuator and the second actuator may be electromagnetic actuators. The first optical member may be a shutter. The second optical member may be a shutter different from the first optical member.

According to a thirteenth aspect of the present invention, in the tenth aspect, the first optical member may be heavier than the second optical member.

According to a fourteenth aspect of the present invention, in the tenth aspect, the endoscope system may further include a condenser and a signal line connecting the first actuator and the second actuator to the signal source. The first actuator and the second actuator may be connected in series to each other. The condenser may be connected to the signal line in parallel with the first actuator.

According to a fifteenth aspect of the present invention, in the tenth aspect, the endoscope system may further include a detector and a control circuit. The detector may be configured to detect positions of the first optical member and the second optical member. The control circuit may be configured to control the signal source such that a state of the endoscope system becomes any one of a first state and a second state on the basis of the positions detected by the detector. The first state is a state in which the control signal having the signal value less than the predetermined value is continuously applied to the first actuator and the second actuator for longer than or equal to the first application duration. The second state is a state in which the control signal having the signal value greater than or equal to the predetermined value is continuously applied to the first actuator and the second actuator for longer than or equal to the second application duration and shorter than the first application duration.

According to a sixteenth aspect of the present invention, an optical adaptor for an endoscope includes a first optical member, a second optical member, a first actuator, and a second actuator. The first actuator is configured to operate when a control signal having a predetermined signal value is applied to the first actuator and configured to move the first optical member. The second actuator is configured to operate only when a control signal having a signal value greater than the predetermined signal value is applied to the second actuator and is configured to move the second optical member. The first actuator and the second actuator are electrically connected to each other.

According to a seventeenth aspect of the present invention, in the sixteenth aspect, the first actuator may be configured to move the first optical member when the control signal having the predetermined signal value is continuously applied to the first actuator for longer than or equal to a first application duration. The second actuator may be configured to move the second optical member only when the control signal having the signal value greater than or equal to the predetermined signal value is continuously applied to the second actuator for longer than or equal to a second application duration. The first application duration may be longer than the second application duration.

According to an eighteenth aspect of the present invention, a method of controlling an endoscope system includes a first step and a second step. The endoscope system includes a first optical member, a second optical member, a first actuator capable of controlling the first optical member, a second actuator capable of controlling the second optical member, and a signal source configured to output a control signal to the first actuator and the second actuator. The first actuator and the second actuator are electrically connected to the signal source. The first actuator is configured to move the first optical member when the control signal is applied to the first actuator. The second actuator is configured to move the second optical member only when the control signal having a signal value greater than or equal to a predetermined value is applied to the second actuator. The signal source is configured to apply the control signal having the signal value greater than or equal to the predetermined value or the control signal having a signal value less than the predetermined value to the first actuator in the first step. The signal source is configured to apply the control signal having the signal value greater than or equal to the predetermined value to the second actuator in the second step.

BRIEF DESCRIPTION OF THE DRAWINGS

FIG. 18A is a diagram showing optical characteristics in the endoscope device according to the fifth embodiment of the present invention.

FIG. 18B is a diagram showing optical characteristics in the endoscope device according to the fifth embodiment of the present invention.

FIG. 18C is a diagram showing optical characteristics in the endoscope device according to the fifth embodiment of the present invention.

FIG. 28 is a block diagram showing a configuration of an endoscope device according to a third modified example of the first to seventh embodiments of the present invention.

FIG. 29 is a block diagram showing a configuration of an endoscope device according to the third modified example of the first to seventh embodiments of the present invention.

FIG. 30 is a block diagram showing a configuration of an endoscope device according to the third modified example of the first to seventh embodiments of the present invention.

DETAILED DESCRIPTION OF THE INVENTION

Hereinafter, embodiments of the present invention will be described with reference to the drawings.

(First Embodiment)

Figure 1:
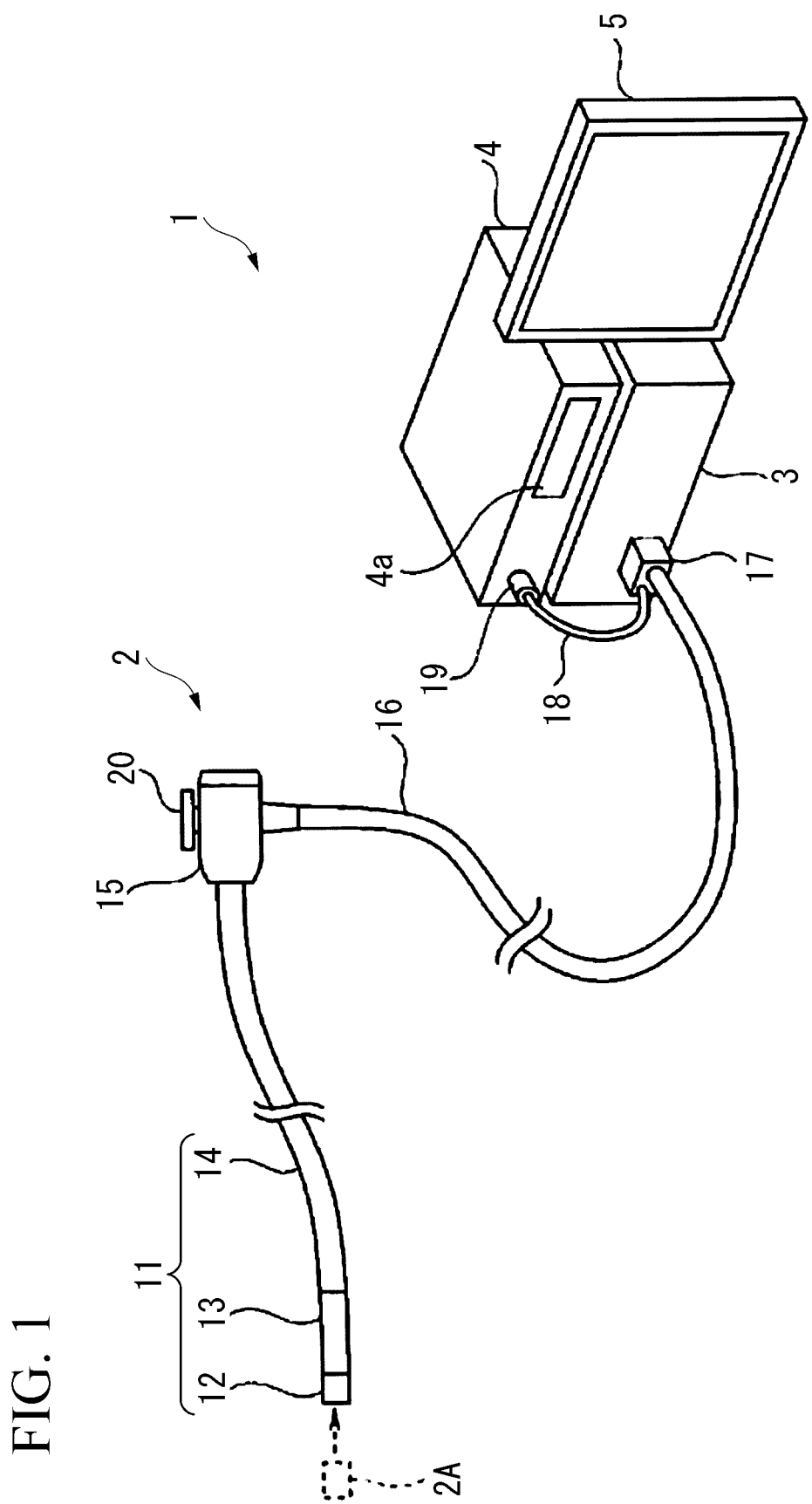
FIG. 1 is a perspective view of an endoscope device according to a first embodiment of the present invention.

FIG. 1 shows the exterior of an endoscope device 1 according to a first embodiment of the present invention. As shown in FIG. 1, the endoscope device 1 includes an endoscope 2, a light source device 3, a main body unit 4, and a display unit 5.

The endoscope 2 includes an insertion unit 11, an operation unit 15, and a cable 16. The insertion unit 11 is elongated and flexible. The operation unit 15 is connected to the insertion unit 11. The cable 16 is connected to the operation unit 15.

The tip end of the cable 16 connected to the operation unit 15 is connected to a connector 17. The connector 17 is attached to the light source device 3. In addition to the cable 16, a cable 18 is connected to the connector 17. The cable 18 is connected to a connector 19. The connector 19 is attached to the main body unit 4.

The insertion unit 11 of the endoscope 2 includes a tip end part 12, a bending part 13, and a base end part 14. The tip end part 12 is disposed at the tip end of the insertion unit 11. The base end part 14 is disposed at the base end of the insertion unit 11. An optical adaptor 2A is attached to the tip end part 12. It is possible to attach the optical adaptor 2A to the tip end part 12 and detach the optical adaptor 2A from the tip end part 12. The bending part 13 is disposed between the tip end part 12 and the base end part 14. The bending part 13 is flexible and capable of bending freely. A user is able to bend the bending part 13 by operating a bending knob 20 disposed on the operation unit 15. The base end part 14 is connected to the operation unit 15. An imaging signal output from the insertion unit 11 is transmitted to the main body unit 4 by the cable 16.

The light source device 3 generates illumination light. The illumination light generated by the light source device 3 is transmitted to the tip end part 12 of the insertion unit 11 by the cable 16 and a light guide disposed inside the insertion unit 11. The main body unit 4 includes an operation unit 4a. A user is able to input a variety of instructions by operating the operation unit 4a. The main body unit 4 outputs an image signal that is based on the imaging signal output from the insertion unit 11 to the display unit 5. The display unit 5 displays an image on the basis of the image signal.

Figure 2:
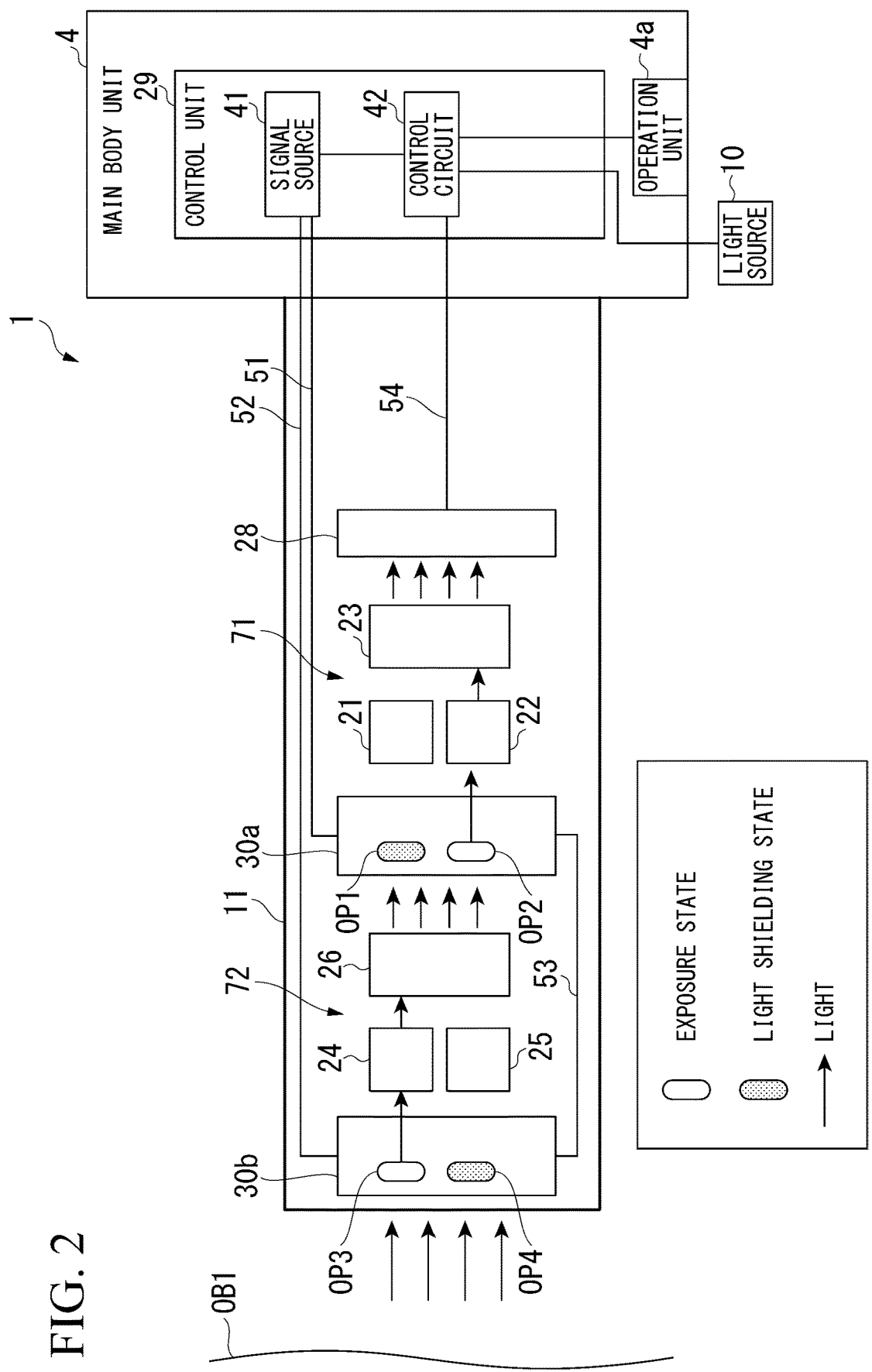
FIG. 2 is a block diagram showing a configuration of the endoscope device according to the first embodiment of the present invention.

FIG. 2 shows a configuration of the endoscope device 1. In FIG. 2, the display unit 5, the operation unit 15, the cable 16, and the like are not shown.

A schematic configuration of the endoscope device 1 will be described. The endoscope device 1 includes a light source 10, the insertion unit 11, and a signal source 41. As shown in FIG. 1, the insertion unit 11 includes the tip end part 12 and the base end part 14. The signal source 41 is disposed outside the insertion unit 11. The signal source 41 outputs a control signal to a signal line 51 passing through the tip end part 12 and the base end part 14 of the insertion unit 11. The tip end part 12 includes an imaging device 28, a first imaging optical system 71, a second imaging optical system 72, a first actuator 30a, and a second actuator 30b. The first imaging optical system 71 and the second imaging optical system 72 include at least one optical member disposed between a subject OB1 and the imaging device 28. The control signal output to the signal line 51 is applied to the first actuator 30a. The control signal output to the signal line 51 is applied to the second actuator 30b. A first optical member is any optical member included in a plurality of optical members included in an optical system of the endoscope device 1. The optical system of the endoscope device 1 is the first imaging optical system 71 and the second imaging optical system 72. The optical system of the endoscope device 1 may include an illumination optical system not shown in FIG. 2. A second optical member is any optical member included in the plurality of optical members included in the optical system of the endoscope device 1 and is different from the first optical member.

When a first control signal having a signal value less than a predetermined value or a second control signal having a signal value greater than or equal to the predetermined value is applied to the first actuator 30a, the first actuator 30a moves the first optical member. Only when the second control signal is applied to the second actuator 30b, the second actuator 30b moves the second optical member. The signal source 41 applies the second control signal to the first actuator 30a and the second actuator 30b through the signal line 51 in a first period. The signal source 41 applies the first control signal to the first actuator 30a and the second actuator 30b through the signal line 51 in a second period after the first period.

Specifically, only when the first control signal having a first signal value greater than or equal to a first value and less than a second value or the second control signal having a second signal value greater than or equal to the second value is applied to the first actuator 30a, the first actuator 30a moves the first optical member. The second value is greater than the first value. Only when the second control signal having the second signal value is applied to the second actuator 30b, the second actuator 30b moves the second optical member. The signal source 41 applies the second control signal to the first actuator 30a and the second actuator 30b through the signal line 51 in the first period. The signal source 41 applies the first control signal having the first signal value to the first actuator 30a and applies the first control signal having the first signal value or a third signal value less than the first signal value to the second actuator 30b through the signal line 51 in the second period after the first period.

A detailed configuration of the endoscope device 1 will be described. The insertion unit 11 includes optical systems 21 to 26, the imaging device 28, the first actuator 30a, and the second actuator 30b. These configurations are disposed at the tip end part 12 of the insertion unit 11. The optical systems 21 to 26, the first actuator 30a, and the second actuator 30b are disposed optically in front of the imaging device 28. The main body unit 4 is disposed on the side of the base end part 14 of the insertion unit 11.

The optical systems 21 to 26 are disposed between the subject OB1 and the imaging device 28. The subject OB1 is away from the tip end part 12 of the insertion unit 11 in the optically forward direction of the insertion unit 11. The optical system 24, the optical system 25, and the optical system 26 are disposed between the first actuator 30a and the second actuator 30b. The optical system 24, the optical system 25, and the optical system 26 are optical members of the second imaging optical system 72. A shutter of the second actuator 30b is also the optical member of the second imaging optical system 72.

The optical system 21, the optical system 22, and the optical system 23 are disposed between the first actuator 30a and the imaging device 28. The optical system 21, the optical system 22, and the optical system 23 are optical members of the first imaging optical system 71. A shutter of the first actuator 30a is also the optical member of the first imaging optical system 71. For example, the optical systems 21 to 26 are lenses. The optical systems 21 to 26 form an optical image of the subject OB1 on a light receiving surface of the imaging device 28.

The first actuator 30a includes a first opening OP1 and a second opening OP2. The shutter disposed inside the first actuator 30a covers any one of the first opening OP1 and the second opening OP2. Light is not able to pass through the opening covered by the shutter. In other words, light from the subject OB1 passes through only any one of the first opening OP1 and the second opening OP2.

The second actuator 30b includes a third opening OP3 and a fourth opening OP4. The shutter disposed inside the second actuator 30b covers any one of the third opening OP3 and the fourth opening OP4. Light is not able to pass through the opening covered by the shutter. In other words, light from the subject OB1 passes through only any one of the third opening OP3 and the fourth opening OP4.

The optical system 24 is disposed at a position corresponding to the third opening OP3. Light passing through the third opening OP3 is incident to the optical system 24. The optical system 25 is disposed at a position corresponding to the fourth opening OP4. Light passing through the fourth opening OP4 is incident to the optical system 25. Light passing through the optical system 24 or the optical system 25 is incident to the optical system 26. Light passing through the optical system 26 reaches the first opening OP1 and the second opening OP2. In the example shown in FIG.

2, the state in which the fourth opening OP4 is shielded from light and the third opening OP3 is exposed to light is shown.

The optical system 21 is disposed at a position corresponding to the first opening OP1. Light passing through the first opening OP1 is incident to the optical system 21. The optical system 22 is disposed at a position corresponding to the second opening OP2. Light passing through the second opening OP2 is incident to the optical system 22. Light passing through the optical system 21 or the optical system 22 is incident to the optical system 23. Light passing through the optical system 23 is incident to the imaging device 28. The imaging device 28 is an image sensor. The imaging device 28 generates an imaging signal in accordance with the incident light. In the example shown in FIG. 2, the state in which the first opening OP1 is shielded from light and the second opening OP2 is exposed to light is shown.

The light source 10 is connected to the main body unit 4. The light source 10 is a light emitting device such as a light emitting diode (LED) and a laser diode (LD). The light source 10 is included in the light source device 3 shown in FIG. 1. The light source 10 generates illumination light emitted to the subject OB1.

The main body unit 4 includes a control unit 29 and an operation unit 4a. The control unit 29 includes the signal source 41 and a control circuit 42 (controller). The signal source 41 is a current source or a voltage source. The signal source 41 generates a control signal. The signal source 41 outputs the generated control signal to the signal line 51.

The control circuit 42 is constituted by at least one of a processor and a logic circuit. For example, the processor is at least one of a central processing unit (CPU), a digital signal processor (DSP), and a graphics processing unit (GPU). For example, the logic circuit is at least one of an application specific integrated circuit (ASIC) and a field-programmable gate array (FPGA). The control circuit 42 may include one or a plurality of processors. The control circuit 42 may include one or a plurality of logic circuits.

The control circuit 42 controls the light source 10, the signal source 41, and the imaging device 28. The imaging device 28 is electrically connected to the control circuit 42 by a signal line 54. The imaging device 28 outputs an imaging signal to the signal line 54. The signal line 54 transfers the imaging signal output from the imaging device 28 to the control circuit 42.

The signal source 41 is electrically connected to the signal line 51 and a signal line 52. The signal line 51 and the signal line 52 are disposed inside the insertion unit 11. The signal line 51 and the signal line 52 pass through the tip end part 12 and the base end part 14 of the insertion unit 11. The signal line 51 and the signal line 52 go outside the insertion unit 11 from the base end part 14 of the insertion unit 11. The signal line 51 is electrically connected to the first actuator 30a. The signal line 52 is electrically connected to the second actuator 30b. The first actuator 30a and the second actuator 30b are electrically connected to each other by a signal line 53. Therefore, the first actuator 30a and the second actuator 30b are connected in series to each other. The first actuator 30a is connected to the signal line 52 through the signal line 53 and the second actuator 30b. The second actuator 30b is connected to the signal line 51 through the signal line 53 and the first actuator 30a.

The signal source 41 applies the first control signal and the second control signal to the first actuator 30a and the second actuator 30b by outputting the first control signal and the second control signal to the signal line 51. The first control signal and the second control signal transmitted by the signal line 51 are input to the first actuator 30a. The first control signal and the second control signal applied to the first actuator 30a are output to the signal line 53. The first control signal and the second control signal transmitted by the signal line 53 are input to the second actuator 30b. The first control signal and the second control signal applied to the second actuator 30b are output to the signal line 52. Details of each control signal will be described later.

A computer of the endoscope device 1 may read a program including commands defining the operations of the control circuit 42 and may execute the read program. In other words, the functions of the control circuit 42 may be realized by software. The program, for example, may be provided by using a "computer-readable storage medium" such as a flash memory. In addition, the program may be transmitted from a computer including a storage device or the like storing the program to the endoscope device 1 through a transmission medium or transmission waves in a transmission medium. The "transmission medium" transmitting the program is a medium having a function of transmitting information. The medium having the function of transmitting information includes a network (communication network) such as the Internet and a communication circuit line (communication line) such as a telephone line. In addition, the program described above may realize some of the functions described above. Further, the above-described program may be a differential file (differential program) capable of implementing the above-described function in combination with a program already recorded on the computer.

A user is able to specify a position of the shutter of each of the first actuator 30a and the second actuator 30b by operating the operation unit 4a disposed in the main body unit 4. In other words, a user is able to input an instruction for switching optical characteristics. When a user inputs the instruction by operating the operation unit 4a, the instruction is input to the control circuit 42. The control circuit 42 controls the signal source 41 on the basis of the instruction.

In FIG. 1, the operation unit 4a is disposed in the main body unit 4. The operation unit 4a may transmit an instruction for switching optical characteristics to the control unit 29 through wired or wireless communication. Therefore, the operation unit 4a may be constituted as a remote controller or the like and may be independent of the main body unit 4.

In FIG. 2, the first actuator 30a is disposed on the side close to the imaging device 28 and the second actuator 30b is disposed on the side far from the imaging device 28. The first actuator 30a may be disposed on the side far from the imaging device 28 and the second actuator 30b may be disposed on the side close to the imaging device 28.

Figure 3:
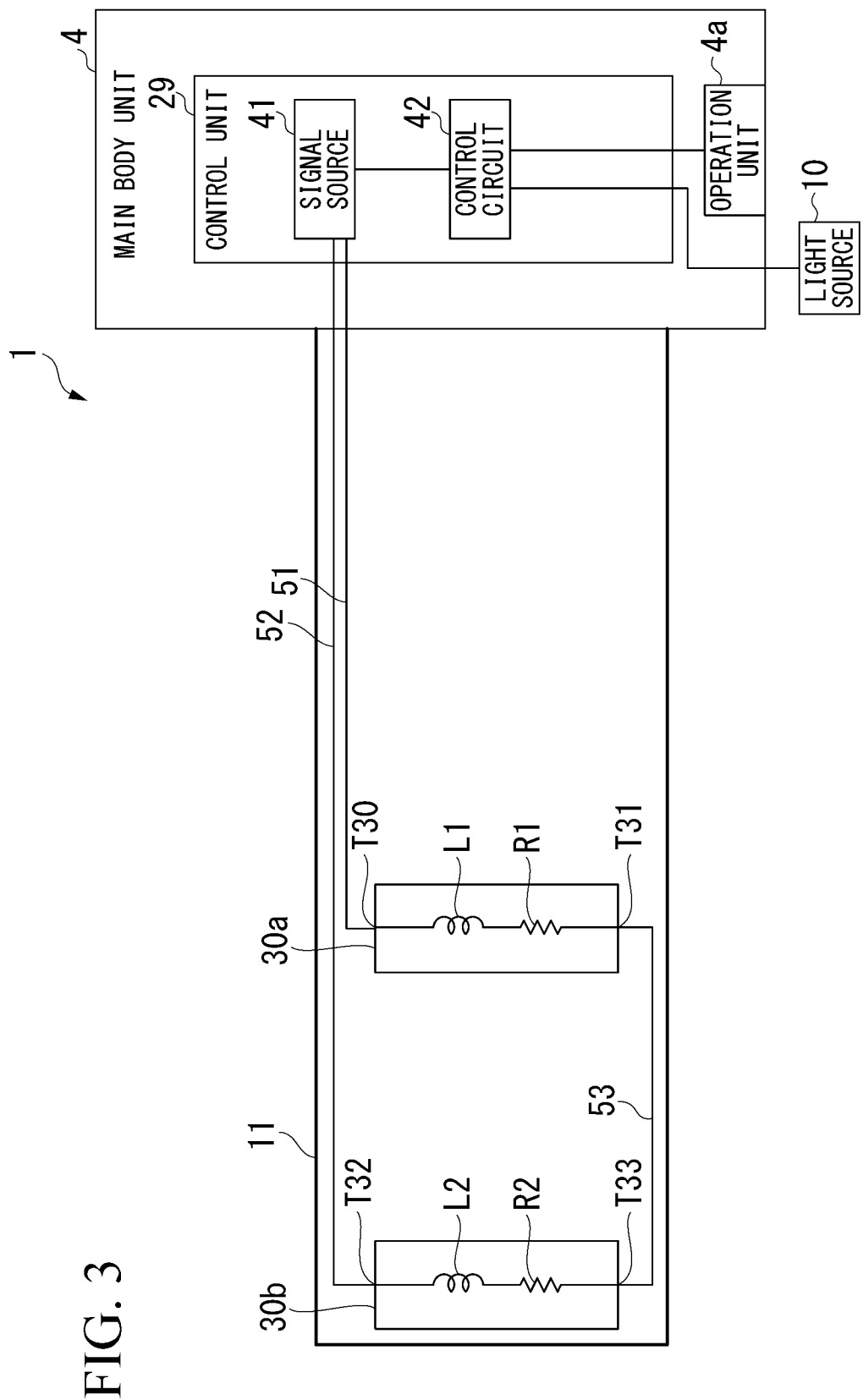
FIG. 3 is a diagram showing an equivalent circuit of actuators in the endoscope device according to the first embodiment of the present invention.

FIG. 3 shows an equivalent circuit of the first actuator 30a and the second actuator 30b. The first actuator 30a and the second actuator 30b are electromagnetic actuators. The first actuator 30a is equivalent to a circuit in which a coil L1 and a resistor R1 are connected in series to each other. The second actuator 30b is equivalent to a circuit in which a coil L2 and a resistor R2 are connected in series to each other.

The first actuator 30a includes a first terminal T30 and a second terminal T31. The second actuator 30b includes a first terminal T32 and a second terminal T33. The first terminal T30 of the first actuator 30a is connected to the signal line 51 and the second terminal T31 of the first actuator 30a is connected to the signal line 53. The first terminal T32 of the second actuator 30b is connected to the signal line 52 and the second terminal T33 of the second actuator 30b is connected to the signal line 53. The coil L1 and the resistor R1 are connected in series to each other between the first terminal T30 and the second terminal T31 of the first actuator 30a. The coil L2 and the resistor R2 are connected in series to each other between the first terminal T32 and the second terminal T33 of the second actuator 30b.

The coil L1 and the resistor R1 are electrically connected to the signal line 51. The coil L1 and the resistor R1 are electrically connected to the signal line 52 through the signal line 53 and the second actuator 30b. The coil L2 and the resistor R2 are electrically connected to the signal line 52. The coil L2 and the resistor R2 are electrically connected to the signal line 51 through the signal line 53 and the first actuator 30a. For example, the resistance values of the resistor R1 and the resistor R2 are the same.

When current having the amount satisfying a condition for driving a shutter flows in the coil L1 or the coil L2 for the duration satisfying the condition, the shutter moves. In order to drive the shutter, current satisfying the condition needs to flow in the coil L1 or the coil L2. However, the shutter does not need to be driven by constant current. In other words, as long as the current satisfying the condition for driving the shutter flows in the coil L1 or the coil L2, the shutter may be driven by constant voltage.

A configuration of the first actuator 30a will be described with reference to FIGS. 4 to 6. Since the second actuator 30b is constituted similarly to the first actuator 30a, a configuration of the first actuator 30a as a representative will be described and a configuration of the second actuator 30b will not be described. For the convenience of description, the configuration shown in FIGS. 4 to 6 is cited in the description using the configuration of the second actuator 30b.

Figure 4:
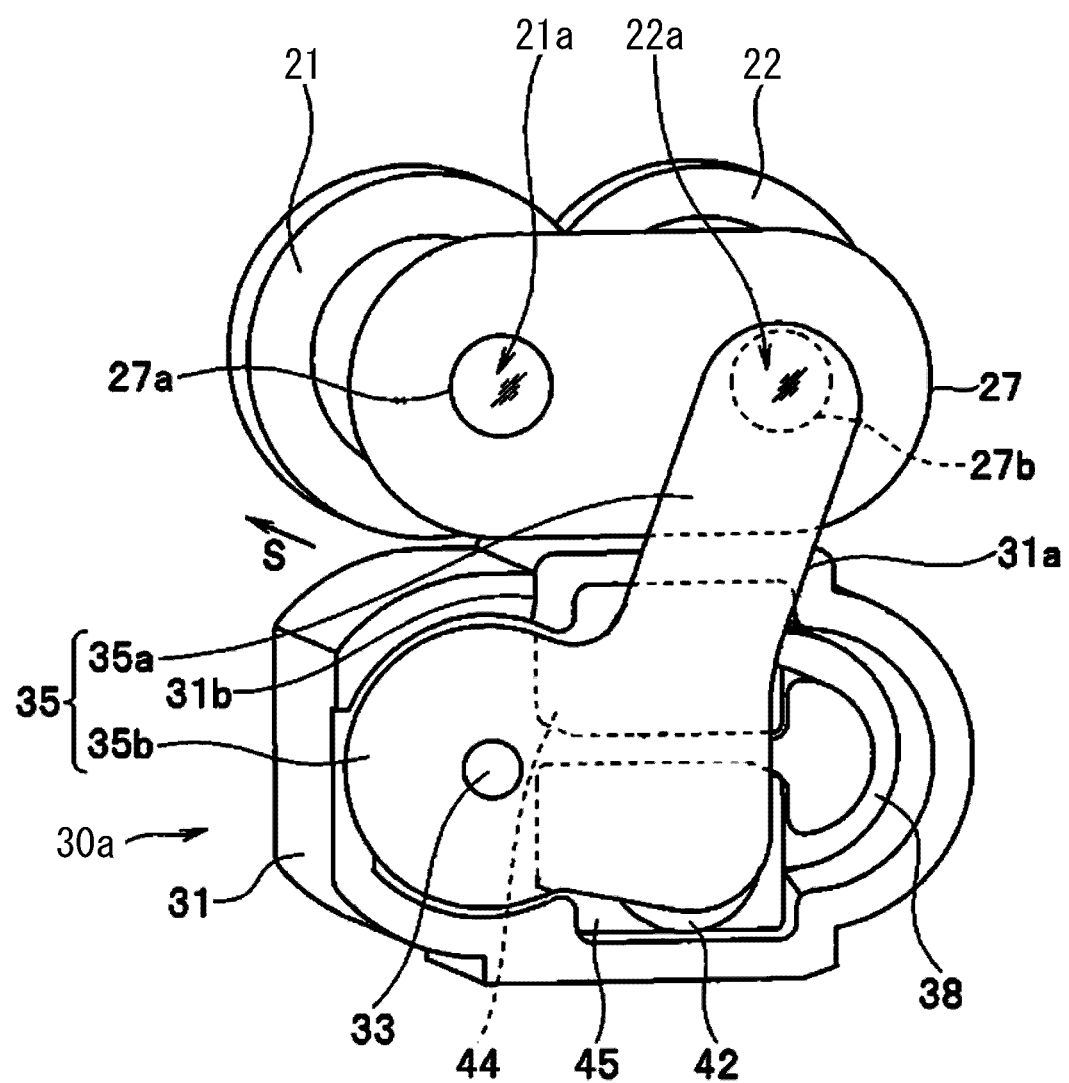
FIG. 4 is a perspective view of an actuator in the endoscope device according to the first embodiment of the present invention.
Figure 5:
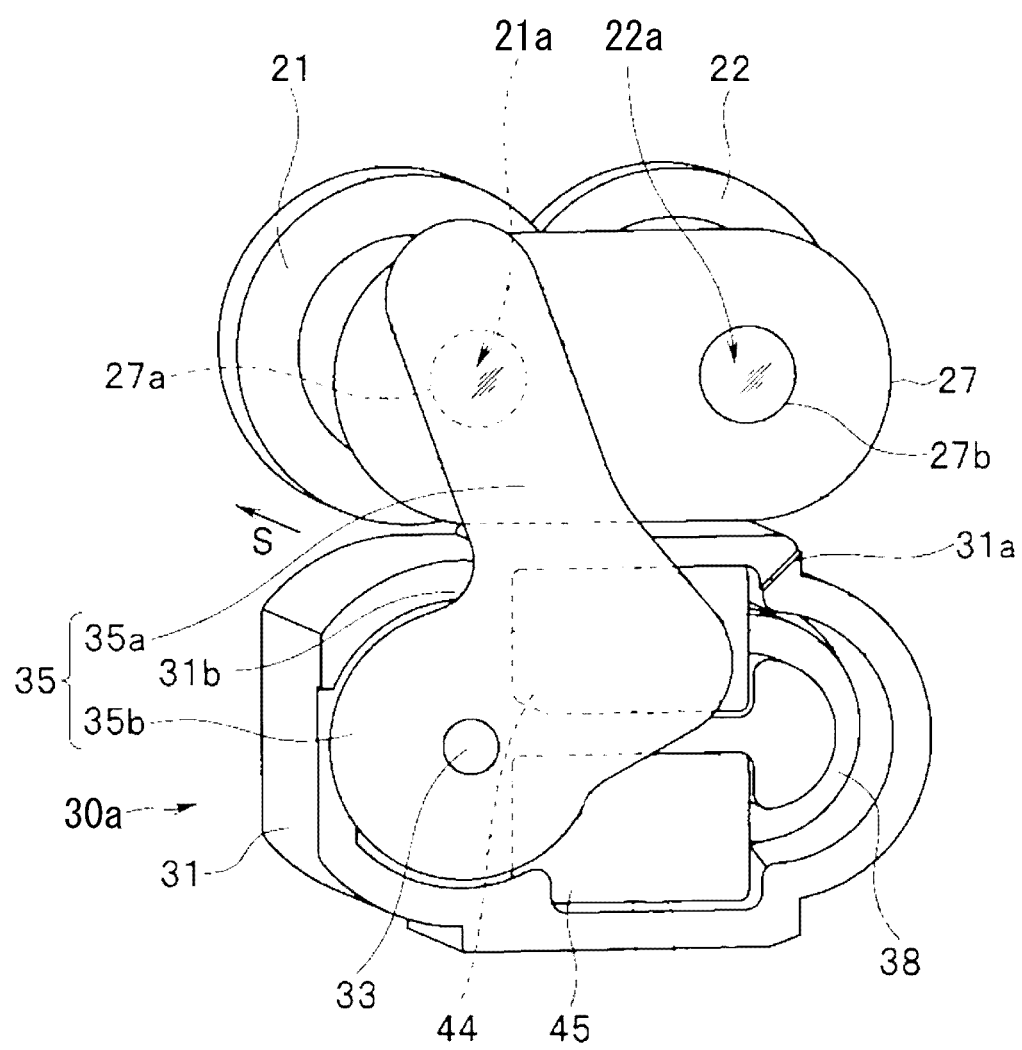
FIG. 5 is a perspective view of an actuator in the endoscope device according to the first embodiment of the present invention.
Figure 6:
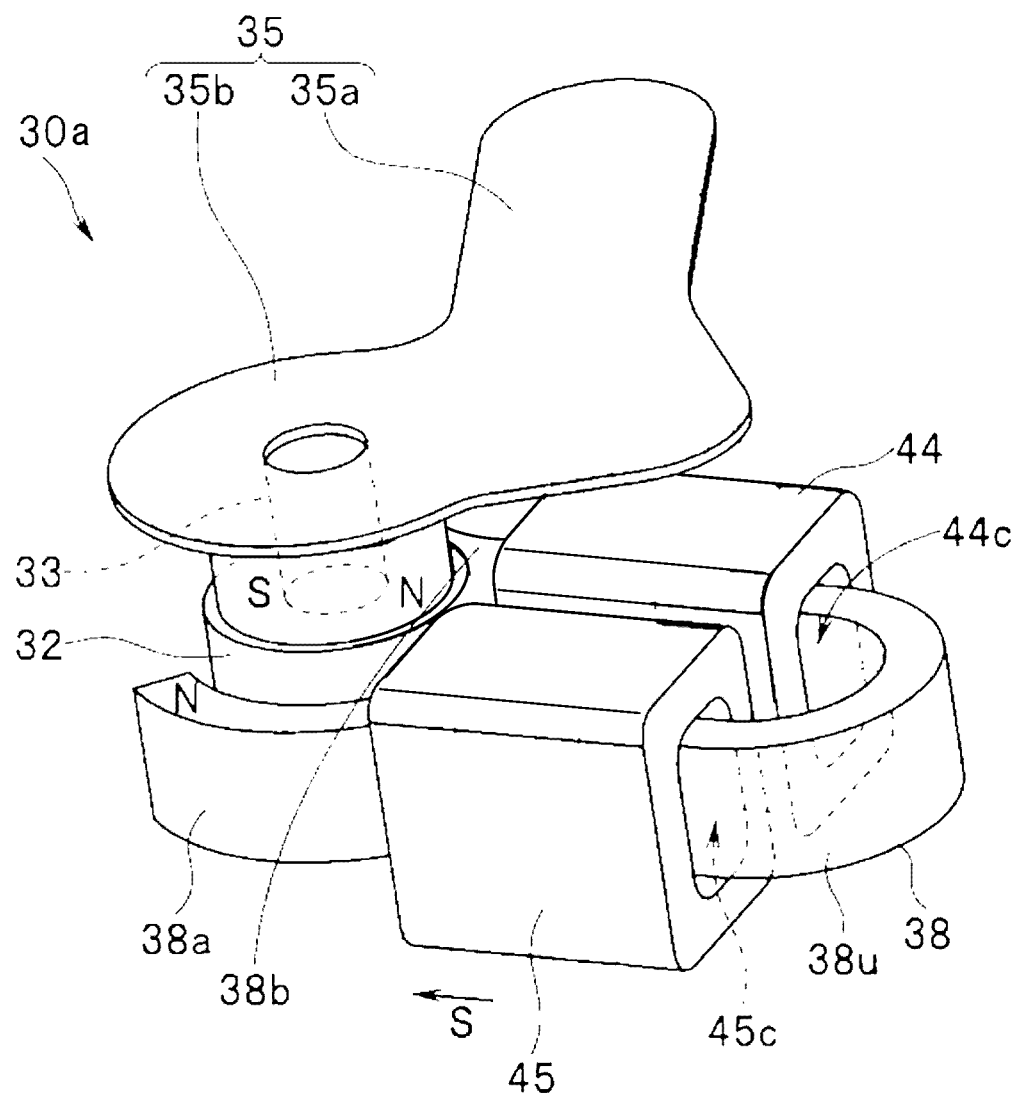
FIG. 6 is a perspective view of an actuator in the endoscope device according to the first embodiment of the present invention.

As shown in FIGS. 4 to 6, the first actuator 30a includes a diaphragm plate 27, a holding member 31, a magnet rotor 32, a rotation axis 33, a shutter 35, a yolk 38, a coil 44, and a coil 45.

The holding member 31 is disposed close to the optical system 21 and the optical system 22 below the optical system 21 and the optical system 22. The magnet rotor 32, the rotation axis 33, a fixed part 35b of the shutter 35, and the yolk 38 are disposed inside the holding member 31.

As shown in FIGS. 4 to 6, the rotation axis 33 is held so as to rotate with respect to the holding member 31. The circular magnet rotor 32 is fixed on the circumference at the end of the rotation axis 33. The magnet rotor 32 is a permanent magnet. An N pole is formed in one half of the magnet rotor 32 and an S pole is formed in the other half of the magnet rotor 32. When the rotation axis 33 rotates, the magnet rotor 32 rotates together with the rotation axis 33.

The shutter 35 is a non-magnetic substance and has a thin plate shape. The shutter 35 includes a light shielding part 35a and the fixed part 35b. The fixed part 35b of the shutter 35 is fixed to the base end of the rotation axis 33.

The diaphragm plate 27 is disposed between the optical system 21 and the optical system 22, and the light shielding part 35a of the shutter 35. The diaphragm plate 27 includes a first opening 27a corresponding to the first opening OP1 and a second opening 27b corresponding to the second opening OP2. The diaphragm plate 27 is disposed such that the first opening 27a overlaps an end surface 21a of the optical system 21 and the second opening 27b overlaps an end surface 22a of the optical system 22.

The shutter 35 is able to rotate from a first position shown in FIG. 5 to a second position shown in FIG. 4. When the shutter 35 is at the first position, the light shielding part 35a covers the first opening 27a. When the shutter 35 is at the second position, the light shielding part 35a covers the second opening 27b. When the shutter 35 touches a stopper 31b of the holding member 31, the first position is specified.

When the shutter 35 touches a stopper 31a of the holding member 31, the second position is specified.

The yolk 38 is a ferromagnetic substance. The yolk 38 includes a moving part 38u having a U shape and positioned on the side of the base end in an insertion direction S. The moving part 38u passes through a hollow part 44c of the coil 44 and a hollow part 45c of the coil 45. The yolk 38 includes a yolk 38a and a yolk 38b positioned on the side of the tip end in the insertion direction S. The yolk 38a covers one part of the circumference of the magnet rotor 32. The yolk 38b faces the yolk 38a and covers the other part of the circumference of the magnet rotor 32.

When a direct current is applied to the coil 44 and the coil 45, the yolk 38a and the yolk 38b generate a magnetic field. At this time, the yolk 38a and the yolk 38b become different magnetic poles. When the yolk 38a becomes the N pole, the yolk 38b becomes the S pole. When the yolk 38a becomes the S pole, the yolk 38b becomes the N pole. The direction of the magnetic pole generated in the yolk 38a and the yolk 38b changes in accordance with the direction of the direct current applied to the coil 44 and the coil 45.

For example, the yolk 38a becomes the N pole and the yolk 38b becomes the S pole. When the S pole of the magnet rotor 32 is on the side of the yolk 38a and the N pole of the magnet rotor 32 is on the side of the yolk 38b, the yolk 38a (N pole) and the S pole of the magnet rotor 32 attract each other and the yolk 38b (S pole) and the N pole of the magnet rotor 32 attract each other. In this way, the magnet rotor 32 and the rotation axis 33 rotate. Since the rotation axis 33 rotates, the shutter 35 rotates. The shutter 35 rotates until the shutter 35 touches the stopper 31a.

For example, the yolk 38a becomes the N pole and the yolk 38b becomes the S pole. When the N pole of the magnet rotor 32 is on the side of the yolk 38a and the S pole of the magnet rotor 32 is on the side of the yolk 38b, the yolk 38a (N pole) and the N pole of the magnet rotor 32 repel each other and the yolk 38b (S pole) and the S pole of the magnet rotor 32 repel each other. In this way, the magnet rotor 32 and the rotation axis 33 rotate. Since the rotation axis 33 rotates, the shutter 35 rotates. The shutter 35 rotates until the shutter 35 touches the stopper 31b.

As described above, the magnet rotor 32 moves due to the magnetic force generated by the coil 44 and the coil 45. In other words, the magnet rotor 32 rotates. Since the magnet rotor 32 is fixed to the shutter 35, the shutter 35 moves due to the rotation of the magnet rotor 32.

The yolk 38 is inserted into the coil 44 and the coil 45. Wires of the coil 44 and the coil 45 are wound around the yolk 38. Due to the magnetic field generated by the coil 44 and the coil 45, two different magnetic poles (N pole and S pole) are generated in the yolk 38. For this reason, the yolk 38 generates a magnetic force. The magnetic force generated by the yolk 38 acts on the magnet rotor 32. Due to the magnetic force generated by the yolk 38, the magnet rotor 32 moves.

The light shielding part 35a of the shutter 35 fixed to the rotation axis 33 is able to rotate between the first position and the second position. The rotation direction of the rotation axis 33 changes in accordance with the direction of the direct current applied to the coil 44 and the coil 45.

The shutter 35 of the first actuator 30a is the first optical member. The shutter 35 of the first actuator 30a is included in the first imaging optical system 71. The shutter 35 of the second actuator 30b is the second optical member. The shutter 35 of the second actuator 30b is included in the second imaging optical system 72.

The first actuator 30a includes a first coil that generates a magnetic force acting on the first optical member when a control signal is applied to the first actuator 30a. The first coil is the coil 44 and the coil 45. The second actuator 30b includes a second coil that generates a magnetic force acting on the second optical member when a control signal is applied to the second actuator 30b. The second coil is the coil 44 and the coil 45. For example, the number of turns of the first coil is greater than the number of turns of the second coil. In other words, the number of turns of the coil L1 shown in FIG. 3 is greater than the number of turns of the coil L2 shown in FIG. 3.

When control signals having the same signal values are applied to the first actuator 30a and the second actuator 30b, the driving force of the shutter 35 of the first actuator 30a is greater than the driving force of the shutter 35 of the second actuator 30b. For this reason, even when the control signal having a signal value less than that of a control signal to be able to move the shutter 35 of the second actuator 30b is applied to the first actuator 30a, the first actuator 30a is able to switch positions of the shutter 35.

The relationship between a position of the shutter 35 of each actuator and a control signal applied to each actuator will be described. First, a signal value of the control signal is defined. Hereinafter, a first control signal and a second control signal having different signal values will be used. A first signal value of the first control signal is less than a predetermined value. Specifically, the first signal value of the first control signal is greater than or equal to a first value and less than a second value. The second value is greater than the first value. A second signal value of the second control signal is greater than or equal to the predetermined value. Specifically, the second signal value of the second control signal is greater than or equal to the second value. Therefore, the second signal value of the second control signal is greater than the first signal value of the first control signal. The second signal value of the second control signal is less than or equal to the maximum signal value of the control signal that the signal source 41 is able to generate.

The polarity of the control signal is any one of a +direction and a −direction. Whether the polarity of the control signal is the +direction or the −direction, the size of the signal value of the control signal is expressed as a positive value. The first signal value and the second signal value are greater than zero.

The first signal value is a signal value with which the first actuator 30a is able to switch positions of the shutter 35. The first signal value is a signal value with which the second actuator 30b is unable to switch positions of the shutter 35. The second signal value is a signal value with which the first actuator 30a is able to switch positions of the shutter 35 and the second actuator 30b is able to switch positions of the shutter 35.

The first actuator 30a and the second actuator 30b are connected in series to each other. For this reason, a control signal output to the signal line 51 and a control signal applied to each actuator are the same.

The first actuator 30a to which the first control signal in the +direction having the first signal value is applied moves the shutter 35 to a position to cover the second opening OP2. In addition, the first actuator 30a to which the first control signal in the −direction having the first signal value is applied moves the shutter 35 to a position to cover the first opening OP1.

The first actuator 30a to which the second control signal in the +direction having the second signal value is applied moves the shutter 35 to a position to cover the second opening OP2. In addition, the first actuator 30a to which the second control signal in the −direction having the second signal value is applied moves the shutter 35 to a position to cover the first opening OP1.

When the first control signal having the first signal value is applied to the second actuator 30b, the shutter 35 of the second actuator 30b does not move. In order to switch positions of the shutter 35 of the second actuator 30b, the second control signal having the second signal value greater than the first signal value needs to be applied to the second actuator 30b. The second actuator 30b to which the second control signal in the +direction having the second signal value is applied moves the shutter 35 to a position to cover the fourth opening OP4. In addition, the second actuator 30b to which the second control signal in the −direction having the second signal value is applied moves the shutter 35 to a position to cover the third opening OP3.

In the first embodiment, the endoscope device 1 is able to switch four types of optical characteristics. The endoscope device 1 is able to switch optical paths within the imaging optical systems by switching the optical characteristics. In other words, the endoscope device 1 is able to switch light beams incident to the imaging device 28. The four types of optical characteristics that the endoscope device 1 is able to switch are similar to the four types of optical characteristics shown in FIGS. 34A to 34D.

Figure 7:
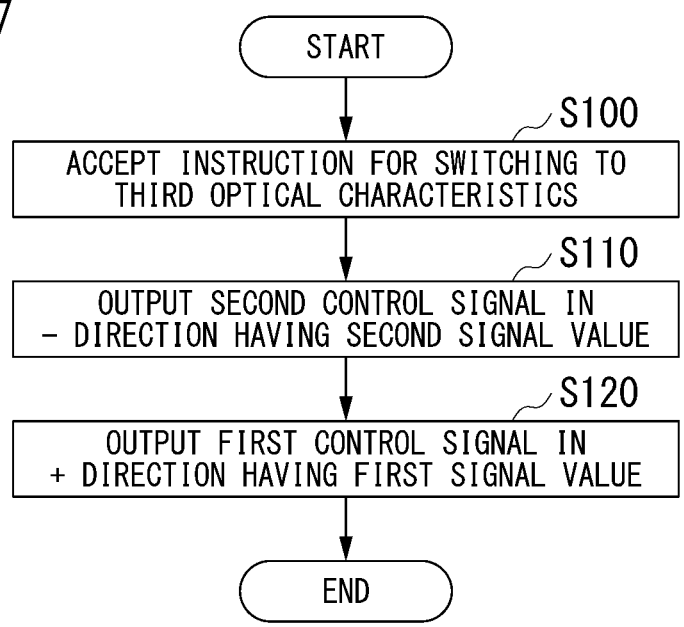
FIG. 7 is a flow chart showing a procedure of an operation of the endoscope device according to the first embodiment of the present invention.
Figure 8A:
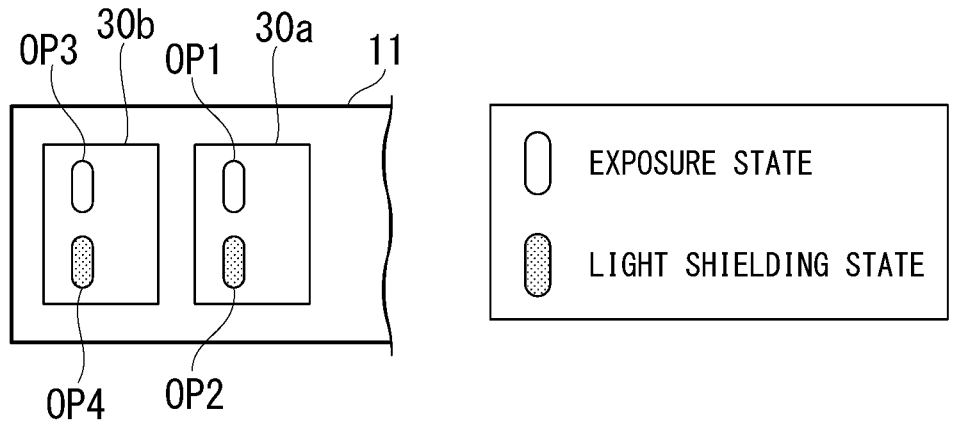
FIG. 8A is a diagram showing optical characteristics in the endoscope device according to the first embodiment of the present invention.
Figure 8B:
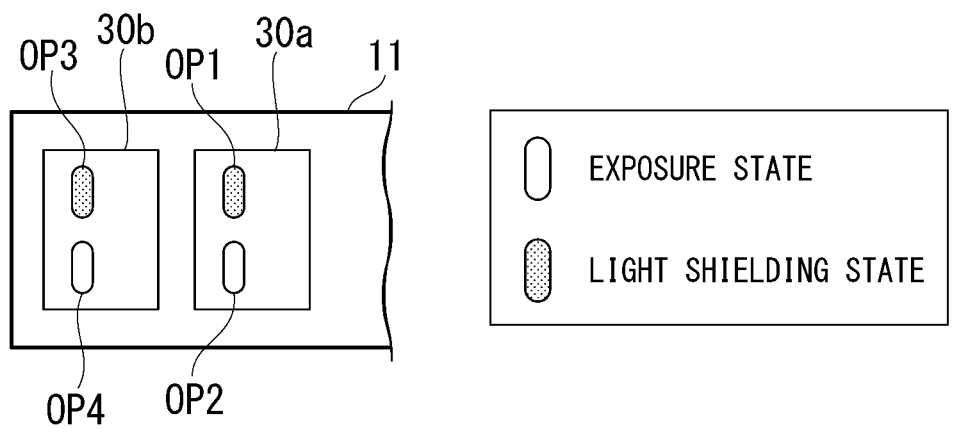
FIG. 8B is a diagram showing optical characteristics in the endoscope device according to the first embodiment of the present invention.
Figure 8C:
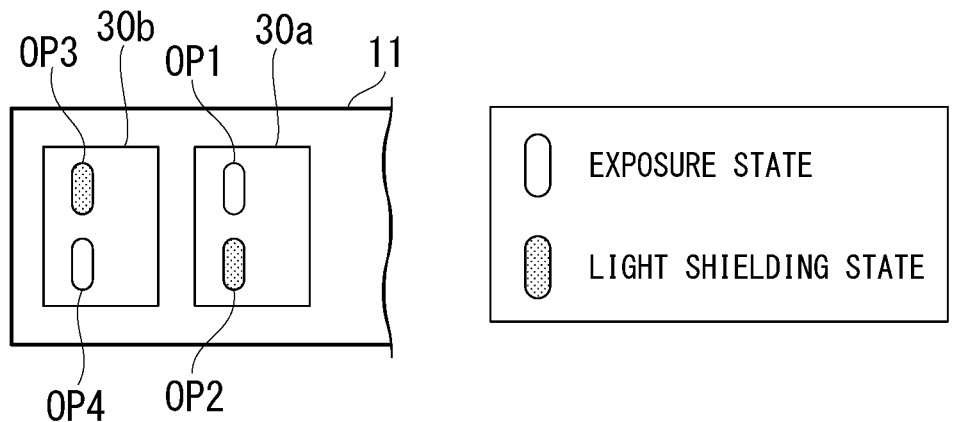
FIG. 8C is a diagram showing optical characteristics in the endoscope device according to the first embodiment of the present invention.

FIG. 7 shows a procedure of an operation of the endoscope device 1. In FIG. 7, an operation of the endoscope device 1 is shown when the optical characteristics of the endoscope device 1 are switched from the first optical characteristics to the third optical characteristics. FIGS. 8A to 8C show the change of the optical characteristics in the operation shown in FIG. 7. In FIGS. 8A to 8C, the optical systems 21 to 26 are not shown.

Before the processing shown in FIG. 7 is executed, the shutter 35 of the first actuator 30a covers the second opening OP2 and the shutter 35 of the second actuator 30b covers the fourth opening OP4 as shown in FIG. 8A. When a user inputs an instruction for switching optical characteristics through the operation unit 4a, switching of the optical characteristics is executed. The operation unit 4a outputs the instruction input by a user to the control circuit 42. At this time, the control circuit 42 accepts an instruction for switching to the third optical characteristics (Step S100).

After Step S100, the control circuit 42 causes the signal source 41 to generate the second control signal in the −direction having the second signal value. The signal source 41 generates the second control signal and outputs the generated second control signal to the signal line 51. In this way, the second control signal is applied to the first actuator 30a and the second actuator 30b (Step S110).

When Step S110 is executed, the shutter 35 of the first actuator 30a and the shutter 35 of the second actuator 30b move. For this reason, as shown in FIG. 8B, the shutter 35 of the first actuator 30a covers the first opening OP1 and the shutter 35 of the second actuator 30b covers the third opening OP3. In this way, the optical characteristics of the endoscope device 1 becomes the fourth optical characteristics.

After Step S110, the control circuit 42 causes the signal source 41 to generate the first control signal in the +direction having the first signal value. The signal source 41 generates the first control signal and outputs the generated first control signal to the signal line 51. In this way, the first control signal is applied to the first actuator 30a and the second actuator 30b (Step S120).

When Step S120 is executed, the shutter 35 of the first actuator 30a moves. The driving force of the shutter 35 generated in the second actuator 30b by the first control signal is not large enough to move the shutter 35. For this reason, the shutter 35 of the second actuator 30b does not move. Consequently, as shown in FIG. 8C, the shutter 35 of the first actuator 30a covers the second opening OP2 and the shutter 35 of the second actuator 30b covers the third opening OP3. In this way, the optical characteristics of the endoscope device 1 becomes the third optical characteristics.

Therefore, the signal source 41 applies the second control signal having the second signal value to the first actuator 30a and the second actuator 30b through the signal line 51 in a first period in which Step S110 is executed. The signal source 41 applies the first control signal having the first signal value to the first actuator 30a and the second actuator 30b through the signal line 51 in a second period in which Step S120 is executed.

Figure 9A:
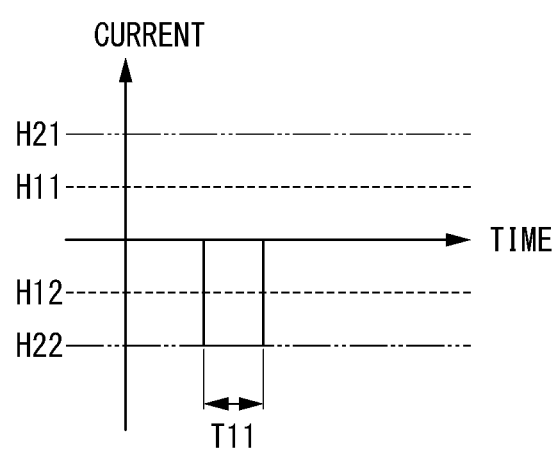
FIG. 9A is a diagram showing a waveform of a control signal applied to an actuator in the endoscope device according to the first embodiment of the present invention.
Figure 9B:
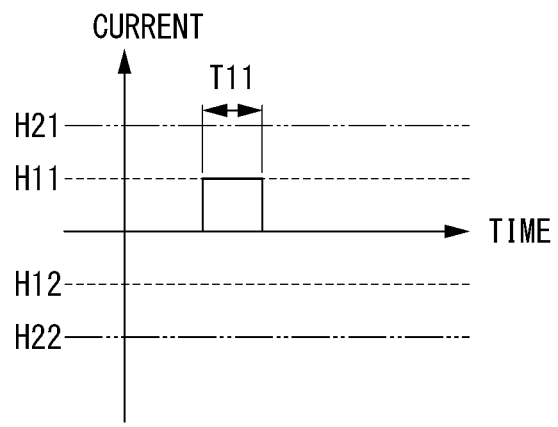
FIG. 9B is a diagram showing a waveform of a control signal applied to the actuator in the endoscope device according to the first embodiment of the present invention.

FIG. 9A shows a waveform of the second control signal applied to the first actuator 30a and the second actuator 30b in Step S110. FIG. 9B shows a waveform of the first control signal applied to the first actuator 30a and the second actuator 30b in Step S120. The horizontal axis in each drawing represents time and the vertical axis in each drawing represents current.

As shown in FIG. 9A, the signal value of the second control signal in the −direction is H22 and the duration during which the second control signal is applied to the first actuator 30a and the second actuator 30b is T11. The signal value of the second control signal in the +direction not shown in FIG. 9A is H21 and the duration during which the second control signal is applied to the first actuator 30a and the second actuator 30b is T11.

As shown in FIG. 9B, the signal value of the first control signal in the +direction is H11 and the duration during which the first control signal is applied to the first actuator 30a and the second actuator 30b is T11. The signal value of the first control signal in the −direction not shown in FIG. 9B is H12 and the duration during which the first control signal is applied to the first actuator 30a and the second actuator 30b is T11.

The signal value H11 and the signal value H21 represent a signal value in the +direction. The signal value H12 and the signal value H22 represent a signal value in the −direction. The sizes of the signal value H11 and the signal value H12 are the same. The sizes of the signal value H21 and the signal value H22 are the same.

The shutter 35 of the first actuator 30a to which the second control signal is applied in Step S110 moves to a position to cover the first opening OP1. The shutter 35 of the first actuator 30a to which the first control signal is applied in Step S120 moves to a position to cover the second opening OP2. The shutter 35 of the second actuator 30b to which the second control signal is applied in Step S110 moves to a position to cover the third opening OP3. According to the operation shown in FIG. 7, the optical characteristics of the endoscope device 1 are switched from the first optical characteristics to the third optical characteristics specified by a user.

In this way, when a user inputs the instruction for switching optical characteristics through the operation unit 4a, the control signal in accordance with the instruction is applied to the first actuator 30a and the second actuator 30b. Consequently, the optical characteristics of the endoscope device 1 are switched to the desired optical characteristics.

The instruction for switching optical characteristics does not need to be input through the operation unit 4a. In other words, the processing in Step S100 is not essential. For example, a program defining the procedure of switching predetermined optical characteristics may be stored on a memory of the endoscope device 1 in advance. The control circuit 42 may read the program from the memory and may execute the processing in Step S110 and Step S120 in accordance with the program.

In the endoscope device of the related art, the two actuators are connected in parallel to the control unit. The two actuators and the control unit are connected to each other by four signal lines. On the other hand, in the endoscope device 1 according to the first embodiment, the two actuators are connected in series to each other. The two actuators and the control unit 29 are connected to each other by two signal lines.

Since the two actuators are connected in series to each other, the signal values of control signals flowing in the two actuators are the same. In a case in which the two actuators are identically constituted, the combinations of positions of the two actuators are only two combinations corresponding to a control signal in the +direction and a control signal in the −direction. In such a case, the number of optical characteristics that the endoscope device 1 is able to switch is two. In other words, just connecting the two actuators in series to each other does not increase the number of optical characteristics that the endoscope device 1 is able to switch.

In the endoscope device 1 according to the first embodiment, the numbers of turns of the coils of the two actuators are different from each other in addition to connecting the two actuators in series to each other. For this reason, when the first control signal having the first signal value is applied to the first actuator 30a and the second actuator 30b, the driving force of the shutter 35 of the first actuator 30a is greater than the driving force of the shutter 35 of the second actuator 30b. When the first control signal is applied to the first actuator 30a, positions of the shutter 35 of the first actuator 30a are switched. On the other hand, positions of the shutter 35 of the second actuator 30b are not switched unless the second control signal having the second signal value greater than the first signal value is applied. When the first control signal is applied to the first actuator 30a, the endoscope device 1 is able to switch positions of the shutter 35 of the first actuator 30a independently of positions of the shutter 35 of the second actuator 30b. For this reason, the endoscope device 1 is able to switch four types of optical characteristics.

As described above, in the endoscope device 1 according to the first embodiment, the two actuators and the control unit 29 are connected to each other by two signal lines. Even when the number of mounted actuators is greater than two, the number of signal lines connecting a plurality of actuators and the control unit 29 to each other does not need to increase. For this reason, the endoscope device 1 is able to restrict increase in thickness of the insertion unit 11.

The two actuators are mounted in the tip end part 12 of the insertion unit 11. Three or more actuators may be mounted in the tip end part 12 of the insertion unit 11. Even when the number of actuators is three or more, the actuators are connected in series to each other. A plurality of actuators and the control unit 29 are connected to each other by two signal lines regardless of the number of actuators.

It is assumed that N actuators are mounted in the tip end part 12 of the insertion unit 11. The number N is a natural number of three or more. The number of turns of the coil L1 of the first actuator 30a is set such that positions of the shutter 35 of the first actuator 30a are switched when a control signal in a predetermined direction having the first signal value is applied to the first actuator 30a. The number of turns of the coil L1 of the first actuator 30a is set such that the number is the greatest among the numbers of turns of all the coils. The number of turns of a coil of a (K+1)-th actuator is set such that positions of the shutter 35 are switched when a (K+1)-th control signal in a predetermined direction having a (K+1)-th signal value greater than or equal to a K-th signal value is applied to the(K+1)-th actuator. The number K is a natural number of one or more and less than N. The number of turns of the coil of the (K+1)-th actuator is less than the number of turns of a coil of a K-th actuator.

Each control signal is applied to each actuator in order of the size of a signal value. Before a control signal having less signal value is applied to each actuator, a control signal having greater signal value is applied to each actuator. A control signal in a direction causing the position of the shutter 35 of the K-th actuator to become the desired position is applied to each actuator. In this way, positions of the shutter 35 of the K-th actuator are switched. Even when three or more actuators are mounted in the tip end part 12 of the insertion unit 11, the endoscope device 1 is able to switch positions of each shutter 35. In other words, the endoscope device 1 is able to switch optical characteristics of the endoscope device 1 to the desired optical characteristics.

When it is assumed that the number of actuators mounted in the endoscope device 1 is N, the number of optical characteristics that the endoscope device 1 is able to switch is two to the power of N. The number N is a natural number of two or more.

For example, in a case in which three actuators are mounted in the endoscope device 1, the endoscope device 1 is able to switch eight types of optical characteristics. As the number of actuators mounted in the endoscope device 1 increases, the number of optical characteristics that the endoscope device 1 is able to switch increases accordingly.

In the above-described examples, the numbers of turns of coils of a plurality of actuators are different from each other. The numbers of turns of coils of the plurality of actuators may be the same and magnetic forces of the magnet rotors 32 of the plurality of actuators may be different from each other. The magnet rotor 32 is a permanent magnet. For example, the first actuator 30a includes the magnet rotor 32 (first pennanent magnet) fixed to the shutter 35 (first optical member). The second actuator 30b includes the magnet rotor 32 (second permanent magnet) fixed to the shutter 35 (second optical member). A magnetic force of the magnet rotor 32 of the first actuator 30a may be stronger than a magnetic force of the magnet rotor 32 of the second actuator 30b.

It is assumed that N actuators are mounted in the tip end part 12 of the insertion unit 11. The number N is a natural number of three or more. The magnetic force of the magnet rotor 32 of the first actuator 30a is set such that positions of the shutter 35 of the first actuator 30a are switched when a control signal in a predetermined direction having the first signal value is applied to the first actuator 30a. The magnetic force of the magnet rotor 32 of the first actuator 30a is set such that the magnetic force is the strongest among magnetic forces of magnet rotors 32 of all the actuators. A magnetic force of the magnet rotor 32 of a (K+1)-th actuator is set such that positions of the shutter 35 are switched when a (K+1)-th control signal in a predetermined direction having a (K+1)-th signal value greater than or equal to a K-th signal value is applied to the(K+1)-th actuator. The number K is a natural number of one or more and less than N. The magnetic force of the magnet rotor 32 of the (K+1)-th actuator is weaker than the magnetic force of the magnet rotor 32 of a K-th actuator. The order in which each control signal is applied to each actuator is the same as the order in which each control signal is applied to each actuator in a case in which the numbers of turns of coils of the plurality of actuators are different from each other.

In a case in which the numbers of turns of coils or magnetic forces of permanent magnets of the plurality of actuators are different from each other, ease of movement of the shutter 35 with respect to current, that is, mechanical sensitivity of the shutter 35 is different among the plurality of actuators. In other words, a condition has only to be realized in which the shutter 35 of one or more actuators moves and the shutter 35 of other one or more actuators does not move when a control signal is applied to each actuator. As long as the condition is realized, the configuration of the endoscope device 1 is not limited to the above-described configuration.

For example, ease of rotation of the rotation axis 33 is different among the plurality of actuators. In other words, a friction coefficient of the rotation axis 33 is different among the plurality of actuators. In this way, the condition can be realized in which the shutters 35 of only some of the plurality of actuators move even when the same control signals are applied to the actuators.

A magnetic force of the yolk 38 that is a ferromagnetic substance may be different among the plurality of actuators. For example, components of the material constituting the yolk 38 are different among the plurality of actuators. In this way, the condition can be realized in which ease of rotation of the rotation axis 33 is different among the plurality of actuators.

For example, the first actuator 30a includes a first magnetic substance and a first coil. The first magnetic substance is the yolk 38. The first coil is the coil 44 and the coil 45. The first coil is wound around the first magnetic substance. When a control signal is applied to the first actuator 30a, the first coil causes the first magnetic substance to be magnetized. The second actuator 30b includes a second magnetic substance and a second coil. The second magnetic substance is the yolk 38. The second coil is the coil 44 and the coil 45. The second coil is wound around the second magnetic substance. When a control signal is applied to the second actuator 30b, the second coil causes the second magnetic substance to be magnetized. A magnetic force generated in the first magnetic substance when a control signal having a predetermined signal value is applied to the first actuator 30a may be stronger than a magnetic force generated in the second magnetic substance when the control signal having the predetermined signal value is applied to the second actuator 30b. In other words, a magnetic force generated in the first magnetic substance when a control signal is applied to the first actuator 30a may be stronger than a magnetic force generated in the second magnetic substance when a control signal having the same signal value as the aforementioned control signal is applied to the second actuator 30b.

(Second Embodiment)

Figure 10:
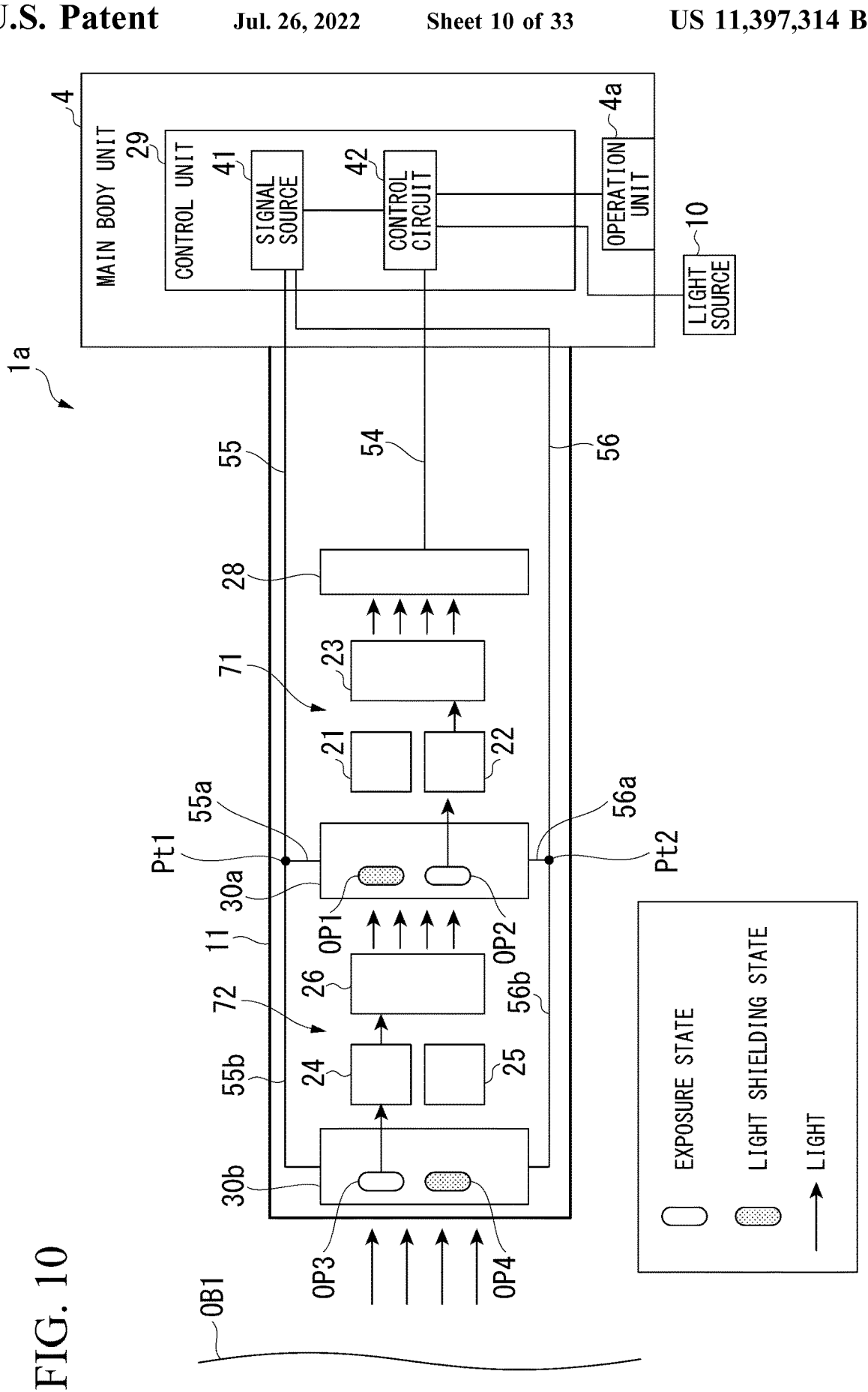
FIG. 10 is a block diagram showing a configuration of an endoscope device according to a second embodiment of the present invention.

FIG. 10 shows a configuration of an endoscope device 1a according to a second embodiment of the present invention. In terms of the configuration shown in FIG. 10, differences from the configuration shown in FIG. 2 will be described.

The signal source 41 is connected to a signal line 55 and a signal line 56. The signal line 55 and the signal line 56 are disposed inside the insertion unit 11. The signal line 55 and the signal line 56 pass through the tip end part 12 and the base end part 14 of the insertion unit 11. The signal line 55 and the signal line 56 go outside the insertion unit 11 from the base end part 14 of the insertion unit 11. The signal line 55 is connected to a signal line 55a and a signal line 55b at a connection point Pt1. The signal line 55a is connected to the first actuator 30a and the signal line 55b is connected to the second actuator 30b. The signal line 56 is connected to a signal line 56a and a signal line 56b at a connection point Pt2. The signal line 56a is connected to the first actuator 30a and the signal line 56b is connected to the second actuator 30b.

The signal line 55 branches off into the signal line 55a and the signal line 55b at the connection point Pt1. The signal line 56 branches off into the signal line 56a and the signal line 56b at the connection point Pt2. The connection point Pt1 and the connection point Pt2 are disposed away from the imaging device 28 toward the subject OB1.

A path through which a control signal output from the signal source 41 passes through includes a first path and a second path. The first path includes the signal line 55, the signal line 55a, the first actuator 30a, the signal line 56a, and the signal line 56. The second path includes the signal line 55, the signal line 55b, the second actuator 30b, the signal line 56b, and the signal line 56. In the first path and the second path, the signal line 55 and the signal line 56 are in common. The first actuator 30a and the second actuator 30b are connected in parallel to the signal line 55 and the signal line 56.

The signal source 41 applies a control signal to the first actuator 30a and the second actuator 30b by outputting the control signal to the signal line 55. The control signal transmitted by the signal line 55 and the signal line 55a is input to the first actuator 30a. The control signal applied to the first actuator 30a is output to the signal line 56a. The control signal output to the signal line 56a is output to the signal line 56. The control signal transmitted by the signal line 55 and the signal line 55b is input to the second actuator 30b. The control signal applied to the second actuator 30b is output to the signal line 56b. The control signal output to the signal line 56b is output to the signal line 56.

In terms of points other than the above, the configuration shown in FIG. 10 is similar to the configuration shown in FIG. 2.

In the endoscope device 1a shown in FIG. 10, the first actuator 30a and the second actuator 30b are connected in parallel to the signal line 55 and the signal line 56. For this reason, in the endoscope device 1a shown in FIG. 10, the voltages of control signals applied to the first actuator 30a and the second actuator 30b are the same.

The first actuator 30a includes the resistor R1 and the coil L1 shown in FIG. 3. The second actuator 30b includes the resistor R2 and the coil L2 shown in FIG. 3. The resistance values of the resistor R1 and the resistor R2 are the same. For this reason, the amount of current that flows in the first actuator 30a and the amount of current that flows in the second actuator 30b are the same. In other words, as with the first embodiment, the signal values of control signals flowing in the first actuator 30a and the second actuator 30b are the same. For this reason, the endoscope device 1a is able to switch optical characteristics of the endoscope device 1a to the desired optical characteristics as with the endoscope device 1 shown in FIG. 2.

In the second embodiment, the following effects are obtained in addition to the effects of the first embodiment. In the endoscope device 1a shown in FIG. 10, when a first voltage is output from the signal source 41 to the signal line 55, the first voltage is applied to the first actuator 30a and the second actuator 30b. In the endoscope device 1 shown in FIG. 2, the first actuator 30a and the second actuator 30b are connected in series to each other. In the endoscope device 1 shown in FIG. 2, it is assumed that a second voltage is applied to the second actuator 30b when the first voltage is applied to the first actuator 30a. A voltage output from the signal source 41 to the signal line 51 is the sum of the first voltage and the second voltage.

As described above, the voltage output from the signal source 41 to the signal line 55 is smaller than the voltage output from the signal source 41 to the signal line 51. From the point of view of security, it is relatively safe to output a small voltage to the tip end part 12 of the insertion unit 11. For this reason, the endoscope device 1a according to the second embodiment is safer than the endoscope device 1 according to the first embodiment.

(Third Embodiment)

Figure 11:
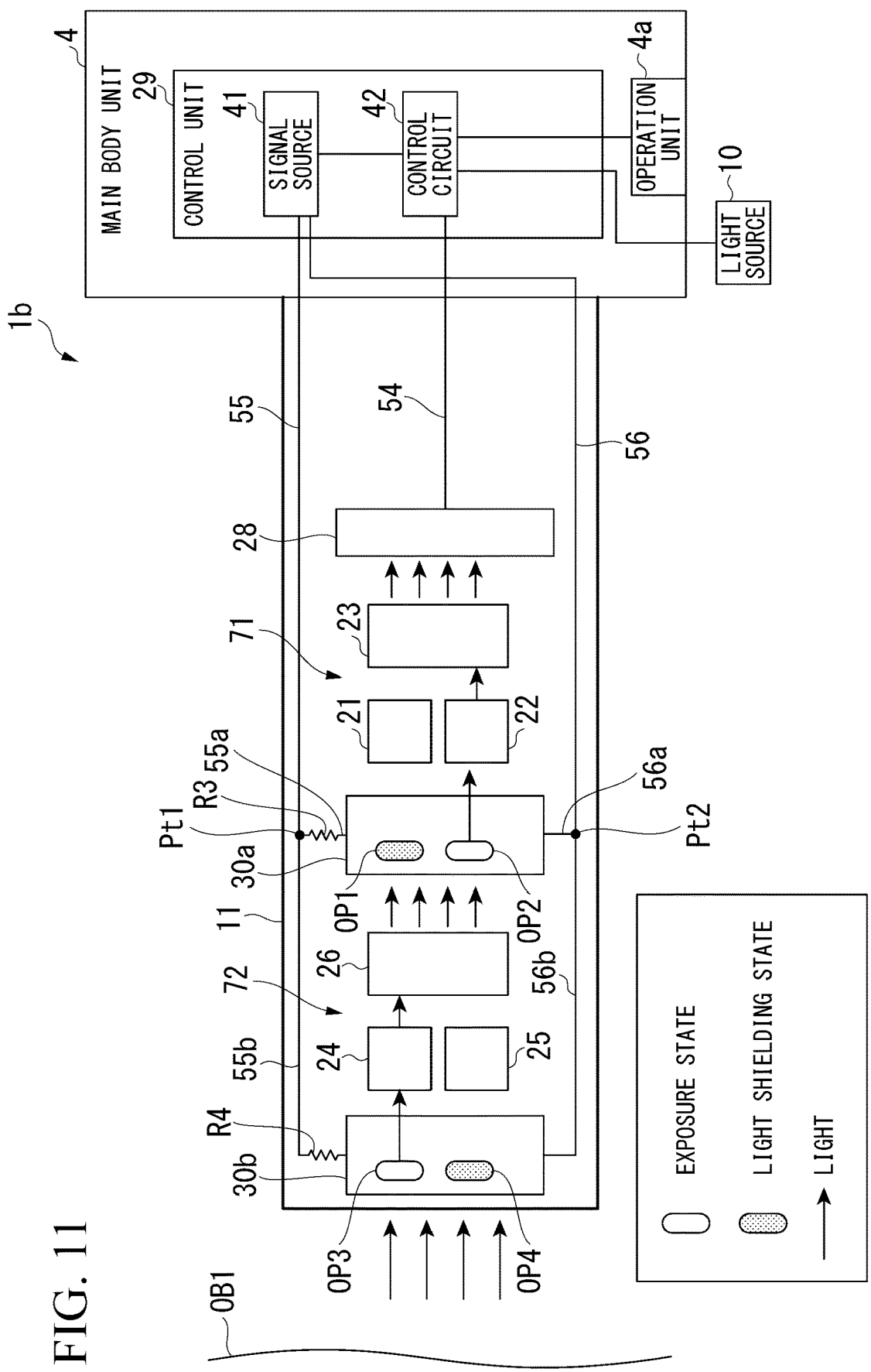
FIG. 11 is a block diagram showing a configuration of an endoscope device according to a third embodiment of the present invention.

FIG. 11 shows a configuration of an endoscope device 1b according to a third embodiment of the present invention. In terms of the configuration shown in FIG. 11, differences from the configuration shown in FIG. 10 will be described.

As with the endoscope device 1a shown in FIG. 10, the first actuator 30a and the second actuator 30b are connected in parallel to the signal line 55. The endoscope device 1b includes a resistor R3 (first resistor) and a resistor R4 (second resistor). The resistor R3 is connected in series to the first actuator 30a and is electrically connected to the signal line 55. The resistor R4 is connected in series to the second actuator 30b and is electrically connected to the signal line 55.

The resistor R3 is inserted into the signal line 55a. The resistor R4 is inserted into the signal line 55b. The resistor R3 may be inserted into the signal line 56a. The resistor R4 may be inserted into the signal line 56b.

In the endoscope device 1a according to the second embodiment, the numbers of turns of coils or the magnetic forces of permanent magnets of the first actuator 30a and the second actuator 30b are different from each other. However, in the endoscope device 1b according to the third embodiment, the first actuator 30a and the second actuator 30b may be identically constituted.

It is assumed that the first actuator 30a does not include the resistor R1 shown in FIG. 3. It is assumed that the second actuator 30b does not include the resistor R2 shown in FIG. 3. The resistance value of the resistor R3 is less than the resistance value of the resistor R4.

In terms of points other than the above, the configuration shown in FIG. 11 is similar to the configuration shown in FIG. 10.

The first actuator 30a and the second actuator 30b are connected in parallel to the signal line 55 and the signal line 56. For this reason, the voltages of control signals applied to the first actuator 30a and the second actuator 30b are the same. The resistance value of the resistor R3 is less than the resistance value of the resistor R4. For this reason, when the signal source 41 outputs a control signal having a predetermined signal value, the signal value of the control signal applied to the first actuator 30a is greater than the signal value of the control signal applied to the second actuator 30b. In other words, the signal source 41 is able to apply control signals having different signal values to the first actuator 30a and the second actuator 30b.

The resistance value of each of the resistor R3 and the resistor R4 is set as follows. In order to switch positions of the shutter 35 of the first actuator 30a, the first control signal has a first signal value greater than or equal to a first value and less than a second value. In order to switch positions of the shutter 35 of the second actuator 30b, the second control signal has a second signal value greater than or equal to the second value. The second value is greater than the first value.

When the second control signal having the second signal value is applied to the second actuator 30b, the control signal applied to the first actuator 30a has a signal value greater than the second signal value. For this reason, positions of the shutter 35 of the first actuator 30a are switched. if the resistance value of the resistor R3 is less than the resistance value of the resistor R4, the endoscope device 1b is able to switch positions of the shutters 35 of the two actuators at the same time.

When the first control signal is applied to the first actuator 30a, the control signal applied to the second actuator 30b has a third signal value less than the first signal value. In order not to switch positions of the shutter 35 of the second actuator 30b, the third signal value needs to be less than the second value. The resistance value of each of the resistor R3 and the resistor R4 is set such that this condition is satisfied.

The operation of the endoscope device 1b according to the third embodiment is similar to the operation of the endoscope device 1 according to the first embodiment. For example, the signal source 41 applies the second control signal having the second signal value to the second actuator 30b through the signal line 55 in a first period in which Step S110 shown in FIG. 7 is executed. In addition, the signal source 41 applies the second control signal having the signal value greater than the second signal value to the first actuator 30a through the signal line 55 in the first period.

When Step S110 is executed, the shutter 35 of the first actuator 30a and the shutter 35 of the second actuator 30b move. For this reason, as shown in FIG. 8B, the shutter 35 of the first actuator 30a covers the first opening OP1 and the shutter 35 of the second actuator 30b covers the third opening OP3. In this way, the optical characteristics of the endoscope device 1b becomes the fourth optical characteristics.

The signal source 41 applies the first control signal having the first signal value to the first actuator 30a through the signal line 55 in a second period in which Step S120 shown in FIG. 7 is executed. In addition, the signal source 41 applies the first control signal having the third signal value less than the first signal value to the second actuator 30b through the signal line 55 in the second period. The third signal value is less than the second value. The third signal value may be less than the first value.

In the third embodiment, the following effects are obtained in addition to the effects of the second embodiment. Configurations of the plurality of actuators mounted in the endoscope device 1b according to the third embodiment may be the same. Resistors having different resistance values are connected in series to the plurality of actuators. It is easier to produce a device including a plurality of same actuators to which resistors having different resistance values are connected in series than to produce a device including a plurality of actuators having different configurations. For this reason, the endoscope device 1b according to the third embodiment is produced more easily than the endoscope device 1 according to the first embodiment and the endoscope device 1a according to the second embodiment.

The coil L1 of the first actuator 30a shown in FIG. 3 and the coil L2 of the second actuator 30b shown in FIG. 3 may include resistance components. For example, the resistance values of the resistance components of the coil L1 and the coil L2 are the same. In such a case, the resistor R3 is unnecessary. The resistor R4 is connected in series to the second actuator 30b and is electrically connected to the signal line 55.

As described above, the resistors having different resistance values are connected in series to the first actuator 30a and the second actuator 30b having the same configurations. Instead of this, the resistors having different resistance values may be disposed inside the first actuator 30a and the second actuator 30b. In other words, the first actuator 30a may include the resistor R1 electrically connected to the signal line 55 and the second actuator 30b may include the resistor R2 electrically connected to the signal line 55. The resistance value of the resistor R1 is less than the resistance value of the resistor R2.

In a case in which the coil L1 and the coil L2 include resistance components, the resistor R1 is unnecessary. For example, the resistance values of resistance components of the coil L1 and the coil L2 are the same. The resistor R2 is electrically connected to the signal line 55.

The two actuators are mounted in the tip end part 12 of the insertion unit 11. Three or more actuators may be mounted in the tip end part 12 of the insertion unit 11. Even when the number of actuators is three or more, resistors having different resistance values are connected in series to each other.

It is assumed that N actuators are mounted in the tip end part 12 of the insertion unit 11. The number N is a natural number of three or more. The resistance value of the resistor connected to the first actuator 30a is set such that positions of the shutter 35 of the first actuator 30a are switched when a control signal in a predetermined direction having the first signal value is applied to the first actuator 30a. The resistance value of the resistor connected to the first actuator 30a is set such that the resistance value is the smallest among resistance values of all the resistors. The resistance value of the resistor connected to a (K+1)-th actuator is set such that positions of the shutter 35 are switched when a (K+1)-th control signal in a predetermined direction having a (K+1)-th signal value greater than or equal to a K-th signal value is applied to the(K+1)-th actuator. The number K is a natural number of one or more and less than N. The resistance value of the resistor connected to the (K+1)-th actuator is greater than the resistance value of the resistor connected to a K-th actuator.

Each control signal is applied to each actuator in order of the size of a signal value. Before a control signal having less signal value is applied to each actuator, a control signal having greater signal value is applied to each actuator. A control signal in a direction causing the position of the shutter 35 of the K-th actuator to become the desired position is applied to each actuator. In this way, positions of the shutter 35 of the K-th actuator are switched.

(Fourth Embodiment)

A configuration of an endoscope device according to a fourth embodiment of the present invention is the same as the configuration of the endoscope device according to any one of the first to third embodiments, excluding the configuration described below. Hereinafter, the endoscope device 1 described in the first embodiment will be used.

In the endoscope device 1 according to the fourth embodiment, the first actuator 30a moves the first optical member only when a control signal is continuously applied to the first actuator 30a for longer than or equal to a first duration. The second actuator 30b moves the second optical member only when a control signal is continuously applied to the second actuator 30b for longer than or equal to a second duration. The second duration is longer than the first duration. The signal source 41 continuously applies a control signal to the first actuator 30a and the second actuator 30b through the signal line 51 in a first period. The signal source 41 continuously applies a control signal to the first actuator 30a and the second actuator 30b through the signal line 51 for longer than or equal to the first duration and shorter than the second duration in a second period after the first period.

The principle of controlling positions of the shutter 35 of the first actuator 30a and the second actuator 30b in accordance with the application duration of a control signal will be described. As described above, the magnet rotor 32 is fixed to the rotation axis 33 of the shutter 35. Positions of the shutter 35 are switched through rotation of the magnet rotor 32. In order for the magnet rotor 32 to rotate, torque needs to be applied to the magnet rotor 32 from the outside. When the torque of greater than or equal to a predetermined amount is applied to the magnet rotor 32, the magnet rotor 32 rotates. The magnet rotor 32 does not rotate unless the amount of torque exceeds the amount of friction load of the magnet rotor 32.

The amount of torque is decided on the basis of the number of turns of the coil 44 and the coil 45, the magnetic force of the magnet rotor 32, the magnetic susceptibility of the yolk 38, and the amount of driving current (signal value of a control signal). In order to be able to control each actuator by changing only the application duration of a control signal, it is necessary to be able to control each actuator without changing the above-described conditions. In other words, the amount of torque is the same between the first actuator 30a and the second actuator 30b.

Therefore, in the following description, it is premised that the amount of torque is greater than or equal to the amount to rotate the magnet rotor 32. The speed (angular speed) at which the magnet rotor 32 rotates will be described. When torque is applied to the magnet rotor 32, the magnet rotor 32 starts to rotate by being accelerated at a predetermined acceleration (angular acceleration). The magnet rotor 32 continues to rotate until the magnet rotor 32 hits the stopper 31a or the stopper 31b. When the magnet rotor 32 hits the stopper 31a or the stopper 31b, the magnet rotor 32 stops.

The rotation speed (angular speed) of the magnet rotor 32 is represented in expression (1). Expression (1) is a motion equation of a general rotor.

$$I\alpha = T \quad (1)$$

In expression (1), I represents the moment of inertia, $\alpha$ represents the angular acceleration, and T represents the torque. Under a condition in which the torque is constant, when the moment of inertia is large, the angular acceleration is small. The moment of inertia is proportional to the mass of a rotor. The magnet rotor 32 is fixed to the shutter 35. For this reason, when the shutter 35 is heavy, the moment of inertia is large. Consequently, the rotation speed of the magnet rotor 32 becomes slow. By differentiating the weights of the shutters 35, it is possible to differentiate the ease of switching positions of the shutter 35 when the same torque is applied to the shutter 35 of the two actuators. In other words, it is possible to differentiate the moving speed of the shutter 35 of the two actuators.

The control method of the two actuators of which the moving speeds of the shutter 35 are different from each other. FIGS. 12A to 12D show movement of the magnet rotor 32 of an actuator of which the moving speed of the shutter 35 is high. FIGS. 13A to 13E show movement of the magnet rotor 32 of an actuator of which the moving speed of the shutter 35 is low. A case in which the moving speed of the shutter 35 of the first actuator 30a is higher than the moving speed of the shutter 35 of the second actuator 30b will be described.

Figure 12A:
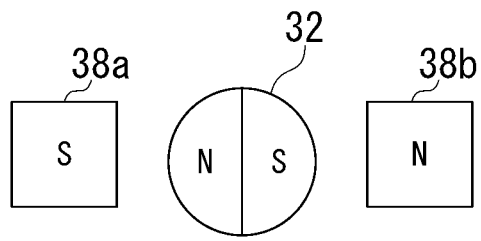
FIG. 12A is a diagram showing movement of a magnet rotor of an actuator in an endoscope device according to a fourth embodiment of the present invention.
Figure 13A:
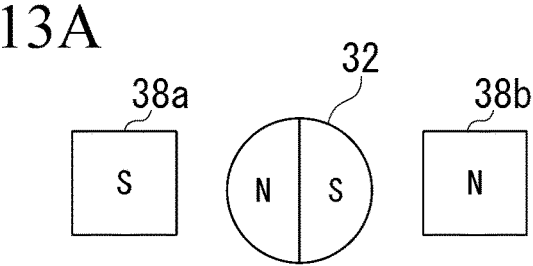
FIG. 13A is a diagram showing movement of the magnet rotor of the actuator in the endoscope device according to the fourth embodiment of the present invention.

FIGS. 12A and 13A show a state when current does not flow in the coil 44 and the coil 45. Since the yolk 38 is a ferromagnetic substance, the yolk 38a facing the N pole of the magnet rotor 32 is magnetized to become an S pole and the yolk 38b facing the S pole of the magnet rotor 32 is magnetized to become an N pole.

Figure 12B:
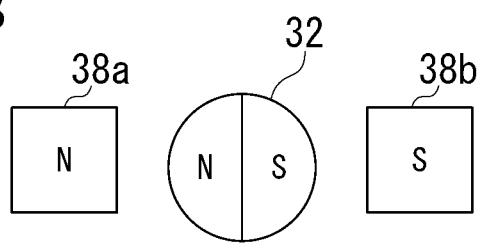
FIG. 12B is a diagram showing movement of the magnet rotor of the actuator in the endoscope device according to the fourth embodiment of the present invention.
Figure 13B:
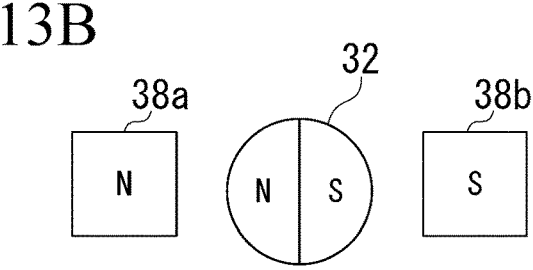
FIG. 13B is a diagram showing movement of the magnet rotor of the actuator in the endoscope device according to the fourth embodiment of the present invention.

FIGS. 12B and 13B show a state when current in a direction in which the magnet rotor 32 rotates flows in the coil 44 and the coil 45 for a short duration. While the current flows in the coil 44 and the coil 45, the yolk 38a is magnetized to become an N pole and the yolk 38b is magnetized to become an S pole due to the magnetic field generated in the coil 44 and the coil 45.

Figure 12C:
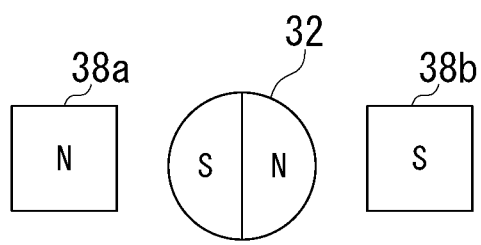
FIG. 12C is a diagram showing movement of the magnet rotor of the actuator in the endoscope device according to the fourth embodiment of the present invention.
Figure 13C:
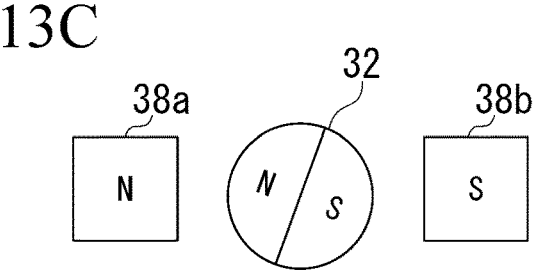
FIG. 13C is a diagram showing movement of the magnet rotor of the actuator in the endoscope device according to the fourth embodiment of the present invention.

FIGS. 12C and 13C show a state when the magnet rotor 32 rotates due to the magnetic force between the yolk 38 and the magnet rotor 32. As shown in FIG. 12C, the magnet rotor 32 half rotates in the first actuator 30a. For this reason, the yolk 38a that is the N pole faces the S pole of the magnet rotor 32 and the yolk 38b that is the S pole faces the N pole of the magnet rotor 32. As shown in FIG. 13C, the magnet rotor 32 slightly rotates in the second actuator 30b.

Figure 12D:
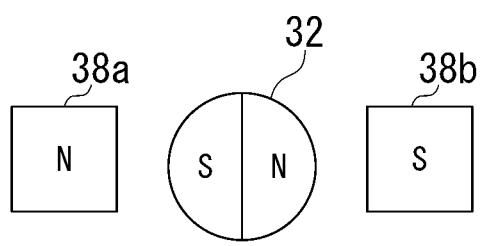
FIG. 12D is a diagram showing movement of the magnet rotor of the actuator in the endoscope device according to the fourth embodiment of the present invention.
Figure 13D:
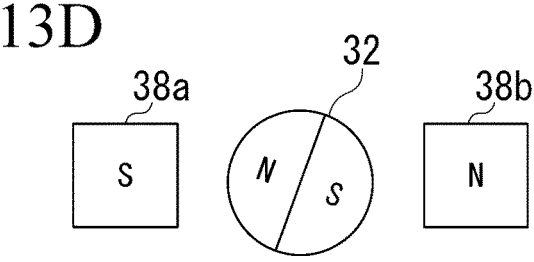
FIG. 13D is a diagram showing movement of the magnet rotor of the actuator in the endoscope device according to the fourth embodiment of the present invention.

FIGS. 12D and 13D show a state when the current flowing in the coil 44 and the coil 45 stops. The coil 44 and the coil 45 stop generating the magnetic field. Since the yolk 38 is a ferromagnetic substance, the yolk 38a facing the S pole of the magnet rotor 32 is magnetized to become an N pole and the yolk 38b facing the N pole of the magnet rotor 32 is magnetized to become an S pole as shown in FIG. 12D.

Figure 13E:
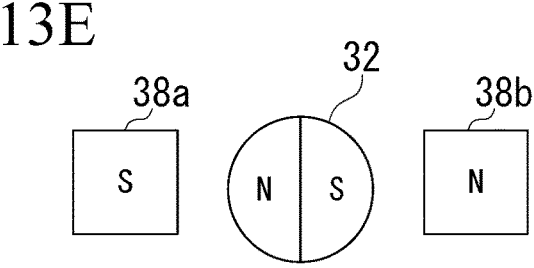
FIG. 13E is a diagram showing movement of the magnet rotor of the actuator in the endoscope device according to the fourth embodiment of the present invention.

On the other hand, as shown in FIG. 13D, the yolk 38a close to the N pole of the magnet rotor 32 is magnetized to become an S pole and the yolk 38b close to the S pole of the magnet rotor 32is magnetized to become an N pole in the second actuator 30b. Thereafter, as shown in FIG. 13E, the yolk 38a that is the S pole faces the N pole of the magnet rotor 32 and the yolk 38b that is the N pole faces the S pole of the magnet rotor 32 in the second actuator 30b. The state of the magnet rotor 32 shown in FIG. 13E is the same as the state shown in FIG. 13A in the second actuator 30b. In other words, the magnet rotor 32 returns to the original state without rotating by one turn.

As described above, in a case in which the application duration of a control signal is short, positions of only the shutter 35 of the first actuator 30a in which the moving speed of the shutter 35 is high are switched. However, positions of the shutter 35 are not switched in the second actuator 30b in which the moving speed of the shutter 35 is low. In a case in which the application duration of a control signal is long, positions of the shutter 35 are switched even in the second actuator 30b in which the moving speed of the shutter 35 is low.

In order to control switching positions of the shutter 35 of the first actuator 30a and the second actuator 30b in accordance with the application duration of a control signal, for example, the weight of the first actuator 30a and the weight of the second actuator 30b need to be different from each other. For example, the second optical member is heavier than the first optical member. In other words, the shutter 35 of the second actuator 30b is heavier than the shutter 35 of the first actuator 30a.

The weight of the shutter 35 of the first actuator 30a is set such that positions of the shutter 35 of the first actuator 30a are switched when a control signal in a predetermined direction having a predetermined signal value is continuously applied to the first actuator 30a for longer than or equal to the first duration. The weight of the shutter 35 of the second actuator 30b is set such that positions of the shutter 35 of the second actuator 30b are switched when a control signal in a predetermined direction having a predetermined signal value is continuously applied to the second actuator 30b for longer than or equal to the second duration.

A method other than the method of differentiating the weights of the shutters 35 of the first actuator 30a and the second actuator 30b may be used. For example, a lubricant such as grease may be applied to the shutter 35 of at least one of the two actuators. As long as it is possible to switch positions of the shutter 35 of each actuator when the above-described control signal is applied to each actuator, any method may be used.

The relationship between a position of the shutter 35 of each actuator and a control signal applied to each actuator will be described. First, the application duration of a control signal is defined. The application duration is the duration during which a control signal is continued to be applied to the first actuator 30a or the second actuator 30b. The application duration of a control signal for switching positions of the shutter 35 of the first actuator 30a is longer than or equal to the first duration. The application duration of a control signal for switching positions of the shutter 35 of the second actuator 30b is longer than or equal to the second duration.

The second duration is longer than the first duration. For this reason, when a control signal is continuously applied to the first actuator 30a and the second actuator 30b for longer than or equal to the second duration, positions of the shutter 35 of the first actuator 30a and the second actuator 30b are switched. In order to switch positions of only the shutter 35 of the first actuator 30a as with the endoscope device 1 according to the first embodiment, the signal source 41 continuously applies a control signal to the first actuator 30a and the second actuator 30b for longer than or equal to the first duration and shorter than the second duration. In this way, positions of only the shutter 35 of the first actuator 30a are switched.

The first actuator 30a and the second actuator 30b are connected in series to each other. For this reason, the control signal output to the signal line 51 and the control signal applied to each actuator are the same.

The first actuator 30a to which a control signal in the +direction having a predetermined signal value is applied for longer than or equal to the first duration moves the shutter 35 to a position to cover the second opening OP2. In addition, the first actuator 30a to which a control signal in the −direction having a predetermined signal value is applied for longer than or equal to the first duration moves the shutter 35 to a position to cover the first opening OP1.

The second actuator 30b to which a control signal in the +direction having a predetermined signal value is applied for longer than or equal to the second duration moves the shutter 35 to a position to cover the fourth opening OP4. In addition, the second actuator 30b to which a control signal in the −direction having a predetermined signal value is applied for longer than or equal to the second duration moves the shutter 35 to a position to cover the third opening OP3.

Figure 14:
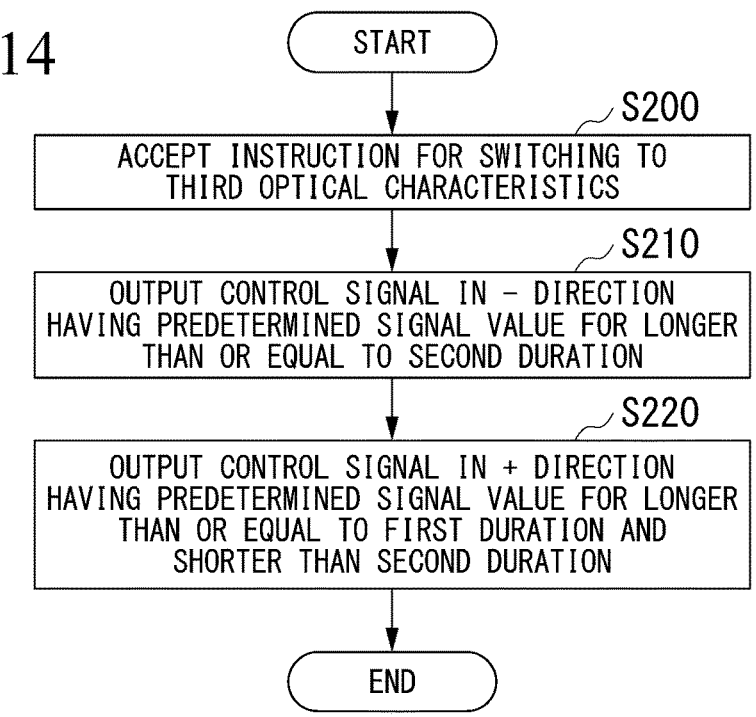
FIG. 14 is a flow chart showing a procedure of an operation of the endoscope device according to the fourth embodiment of the present invention.

FIG. 14 shows a procedure of an operation of the endoscope device 1. In FIG. 14, an operation of the endoscope device 1 is shown when the optical characteristics of the endoscope device 1 are switched from the first optical characteristics to the third optical characteristics. The change of the optical characteristics in the operation shown in FIG. 14 is similar to the change of the optical characteristics shown in FIGS. 8A to 8C.

Before the processing shown in FIG. 14 is executed, the shutter 35 of the first actuator 30a covers the second opening OP2 and the shutter 35 of the second actuator 30b covers the fourth opening OP4 as shown in FIG. 8A. When a user inputs an instruction for switching optical characteristics through the operation unit 4a, switching of the optical characteristics is executed. The operation unit 4a outputs the instruction input by a user to the control circuit 42. At this time, the control circuit 42 accepts an instruction for switching to the third optical characteristics (Step S200).

After Step S200, the control circuit 42 causes the signal source 41 to generate the control signal in the −direction having the predetermined signal value. The signal source 41 generates the control signal and continuously outputs the generated control signal to the signal line 51 for longer than or equal to the second duration. In this way, the control signal is applied to the first actuator 30a and the second actuator 30b (Step S210).

When Step S210 is executed, the shutter 35 of the first actuator 30a and the shutter 35 of the second actuator 30b move. For this reason, as shown in FIG. 8B, the shutter 35 of the first actuator 30a covers the first opening OP1 and the shutter 35 of the second actuator 30b covers the third opening OP3. In this way, the optical characteristics of the endoscope device 1 becomes the fourth optical characteristics.

After Step S210, the control circuit 42 causes the signal source 41 to generate the control signal in the +direction having the predetermined signal value. The signal source 41 generates the control signal and continuously outputs the generated control signal to the signal line 51 for longer than or equal to the first duration and shorter than the second duration. In this way, the control signal is applied to the first actuator 30a and the second actuator 30b (Step S220).

When Step S220 is executed, the shutter 35 of the first actuator 30a moves. The driving force of the shutter 35 generated in the second actuator 30b by the control signal generated in Step S220 is not large enough to move the shutter 35. For this reason, the shutter 35 of the second actuator 30b does not move. Consequently, as shown in FIG. 8C, the shutter 35 of the first actuator 30a covers the second opening OP2 and the shutter 35 of the second actuator 30b covers the third opening OP3. In this way, the optical characteristics of the endoscope device 1 becomes the third optical characteristics.

Therefore, the signal source 41 applies the control signal having the predetermined signal value to the first actuator 30a and the second actuator 30b through the signal line 51 for longer than or equal to the second duration in a first period in which Step S210 is executed. The signal source 41 applies the control signal having the predetermined signal value to the first actuator 30a and the second actuator 30b through the signal line 51 for longer than or equal to the first duration and shorter than the second duration in a second period in which Step S220 is executed.

Figure 15A:
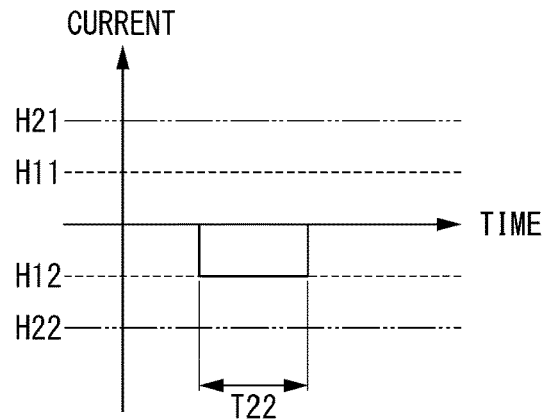
FIG. 15A is a diagram showing a waveform of a control signal applied to the actuator in the endoscope device according to the fourth embodiment of the present invention.
Figure 15B:
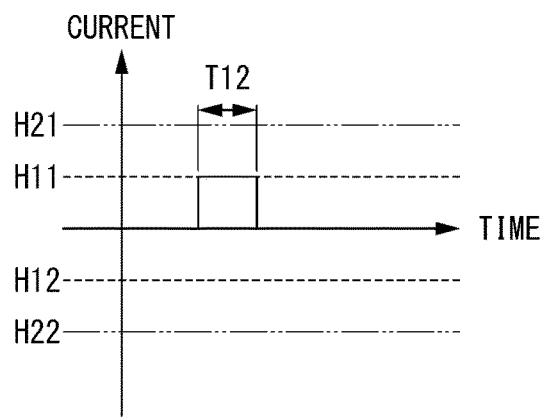
FIG. 15B is a diagram showing a waveform of a control signal applied to the actuator in the endoscope device according to the fourth embodiment of the present invention.

FIG. 15A shows a waveform of the control signal applied to the first actuator 30a and the second actuator 30b in Step S210. FIG. 15B shows a waveform of the control signal applied to the first actuator 30a and the second actuator 30b in Step S220. The horizontal axis in each drawing represents time and the vertical axis in each drawing represents current.

As shown in FIG. 15A, the signal value of the control signal in the −direction is H12 and the duration during which the control signal is applied to the first actuator 30a and the second actuator 30b is T22. The signal value of the control signal in the +direction not shown in FIG. 15A is H11 and the duration during which the control signal is applied to the first actuator 30a and the second actuator 30b is T22.

As shown in FIG. 15B, the signal value of the control signal in the +direction is H11 and the duration during which the control signal is applied to the first actuator 30a and the second actuator 30b is T12. The signal value of the control signal in the −direction not shown in FIG. 15B is H12 and the duration during which the control signal is applied to the first actuator 30a and the second actuator 30b is T12. The duration T22 is longer than the duration T12.

The shutter 35 of the first actuator 30a to which the control signal is applied in Step S210 moves to a position to cover the first opening OP1. The shutter 35 of the first actuator 30a to which the control signal is applied in Step S220 moves to a position to cover the second opening OP2. The shutter 35 of the second actuator 30b to which the control signal is applied in Step S210 moves to a position to cover the third opening OP3. According to the operation shown in FIG. 14, the optical characteristics of the endoscope device 1 are switched from the first optical characteristics to the third optical characteristics specified by a user.

In this way, when a user inputs the instruction for switching optical characteristics through the operation unit 4a, the control signal in accordance with the instruction is applied to the first actuator 30a and the second actuator 30b. Consequently, the optical characteristics of the endoscope device 1 are switched to the desired optical characteristics.

The instruction for switching optical characteristics does not need to be input through the operation unit 4a. In other words, the processing in Step S200 is not essential. For example, a program defining the procedure of switching predetermined optical characteristics may be stored on a memory of the endoscope device 1 in advance. The control circuit 42 may read the program from the memory and may execute the processing in Step S210 and Step S220 in accordance with the program.

In the endoscope device 1 according to the fourth embodiment, as with the endoscope device 1 according to the first embodiment, the two actuators and the control unit 29 are connected to each other by two signal lines. For this reason, the endoscope device 1 is able to restrict increase in thickness of the insertion unit 11.

The two actuators are mounted in the tip end part 12 of the insertion unit 11. Three or more actuators may be mounted in the tip end part 12 of the insertion unit 11. Even when the number of actuators is three or more, the actuators are connected in series to each other. The control unit 29 and a plurality of actuators are connected to each other by two signal lines regardless of the number of actuators.

It is assumed that N actuators are mounted in the tip end part 12 of the insertion unit 11. The number N is a natural number of three or more. The application duration of the control signal for switching positions of the shutter 35 of the first actuator 30a is set such that positions of the shutter 35 of the first actuator 30a are switched when a control signal in a predetermined direction is applied to the first actuator 30a for longer than or equal to the first duration. The application duration of the control signal for switching positions of the shutter 35 of the first actuator 30a is set such that the application duration is the shortest among the application durations of all the control signals. The application duration of the control signal for switching positions of the shutter 35 of a (K+1)-th actuator is set so as to be longer than the application duration of the control signal for switching positions of the shutter 35 of a K-th actuator. The number K is a natural number of one or more and less than N.

Each control signal is applied to each actuator in order of the length of the application duration. The duration during which a control signal is continuously applied to each actuator gradually becomes short. A control signal in a direction causing the position of the shutter 35 of the K-th actuator to become the desired position is applied to each actuator for the minimum required duration for switching positions of the shutter 35 of the K-th actuator. In this way, positions of the shutter 35 of the K-th actuator are switched. Even when three or more actuators are mounted in the tip end part 12 of the insertion unit 11, the endoscope device 1 is able to switch positions of each shutter 35. In other words, the endoscope device 1 is able to switch optical characteristics of the endoscope device 1 to the desired optical characteristics.

When it is assumed that the number of actuators mounted in the endoscope device 1 is N, the number of optical characteristics that the endoscope device 1 is able to switch is two to the power of N. The number N is a natural number of two or more. For example, in a case in which three actuators are mounted in the endoscope device 1, the endoscope device 1 is able to switch eight types of optical characteristics. As the number of actuators mounted in the endoscope device 1 increases, the number of optical characteristics that the endoscope device 1 is able to switch increases accordingly.

Instead of the endoscope device 1 according to the first embodiment, the endoscope device 1a according to the second embodiment may be used.

(Fifth Embodiment)

A configuration of an endoscope device according to a fifth embodiment of the present invention is the same as the configuration of the endoscope device according to any one of the first to third embodiments, excluding the configuration described below. Hereinafter, the endoscope device 1 described in the first embodiment will be used.

In the endoscope device 1 according to the first embodiment, the number of turns of the first coil of the first actuator 30a is greater than the number of turns of the second coil of the second actuator 30b. In order to switch positions of the shutter 35 of the first actuator 30a, the first control signal having the first signal value needs to be applied to the first actuator 30a. In order to switch positions of the shutter 35 of the second actuator 30b, the second control signal having the second signal value greater than the first signal value needs to be applied to the second actuator 30b.

In the endoscope device 1 according to the fifth embodiment, a condition of the duration during which a control signal is continuously applied is necessary in addition to the above-described condition of a signal value. Specifically, only when a first control signal having a signal value less than a predetermined value or a second control signal having a signal value greater than or equal to the predetermined value is continuously applied to the first actuator 30a for longer than or equal to a first application duration (third duration), the first actuator 30a moves the first optical member. Only when the second control signal is continuously applied to the second actuator 30b for longer than or equal to a second application duration (fourth duration), the second actuator 30b moves the second optical member. The second application duration is shorter than the first application duration.

More specifically, only when a first control signal having a first signal value greater than or equal to a first value and less than a second value or a second control signal having a second signal value greater than or equal to the second value is continuously applied to the first actuator 30a for longer than or equal to the first application duration, the first actuator 30a moves the first optical member. The second value is greater than the first value. Only when the second control signal is continuously applied to the second actuator 30b for longer than or equal to the second application duration, the second actuator 30b moves the second optical member.

The signal source 41 applies the second control signal to the first actuator 30a and the second actuator 30b through the signal line 51 for longer than or equal to the second application duration and shorter than the first application duration in a first period. The signal source 41 applies the first control signal to the first actuator 30a and the second actuator 30b through the signal line 51 for longer than or equal to the first application duration in a second period different from the first period.

In order to control switching positions of the shutter 35 of the first actuator 30a and the second actuator 30b in accordance with the application duration of a control signal, for example, the weight of the first actuator 30a and the weight of the second actuator 30b need to be different from each other. For example, the first optical member is heavier than the second optical member. In other words, the shutter 35 of the first actuator 30a is heavier than the shutter 35 of the second actuator 30b.

The weight of the shutter 35 of the first actuator 30a is set such that positions of the shutter 35 of the first actuator 30a are switched when the first control signal in a predetermined direction having the first signal value is continuously applied to the first actuator 30a for longer than or equal to the first application duration. The weight of the shutter 35 of the second actuator 30b is set such that positions of the shutter 35 of the second actuator 30b are switched when the second control signal in a predetermined direction having the second signal value is continuously applied to the second actuator 30b for longer than or equal to the second application duration.

A method other than the method of differentiating the weights of the shutters 35 of the first actuator 30a and the second actuator 30b may be used. For example, a lubricant such as grease may be applied to the shutter 35 of at least one of the two actuators. As long as it is possible to switch positions of the shutter 35 of each actuator when the above-described control signal is applied to each actuator, any method may be used.

The first application duration is longer than the second application duration. For this reason, when the second control signal having the second signal value greater than the first signal value is continuously applied to the first actuator 30a and the second actuator 30b for longer than or equal to the first application duration, positions of the shutter 35 of the first actuator 30a and the second actuator 30b are switched. In order to avoid this, the signal source 41 continuously applies the second control signal to the first actuator 30a and the second actuator 30b for longer than or equal to the second application duration and shorter than the first application duration. In this way, positions of only the shutter 35 of the second actuator 30b are switched.

In the endoscope device 1 according to the fourth embodiment, control signals having different application durations are applied to each actuator in a predetermined order. In the endoscope device 1 according to the fifth embodiment, there is no limitation of the order of control signals that is based on application durations.

In the endoscope device 1 according to the fourth embodiment, torque applied to the magnet rotor 32 is constant and the amount of the torque is always large enough to rotate the magnet rotor 32. In the endoscope device 1 according to the fifth embodiment, signal values of a plurality of control signals are different from each other and application durations of the plurality of control signals are different from each other. Since signal values of the plurality of control signals are different from each other, the amount of the torque is different in accordance with the control signal.

Figure 16A:
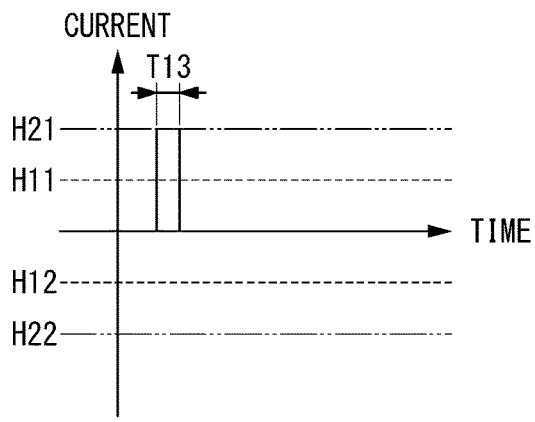
FIG. 16A is a diagram showing a waveform of a control signal applied to an actuator in an endoscope device according to a fifth embodiment of the present invention.
Figure 16B:
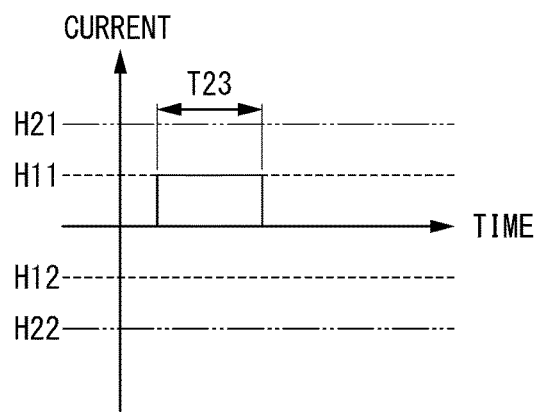
FIG. 16B is a diagram showing a waveform of a control signal applied to the actuator in the endoscope device according to the fifth embodiment of the present invention.

The change of positions of the shutter 35 of each actuator when a control signal shown in FIG. 16A and FIG. 16B is applied to the first actuator 30a and the second actuator 30b will be described. FIG. 16A shows a waveform of the second control signal. FIG. 16B shows a waveform of the first control signal. The horizontal axis in each drawing represents time and the vertical axis in each drawing represents current.

It is assumed that the shutter 35 of the first actuator 30a is heavier than the shutter 35 of the second actuator 30b. In other words, the moving speed of the shutter 35 of the first actuator 30a is lower than the moving speed of the shutter 35 of the second actuator 30b. It is assumed that the number of turns of the first coil of the first actuator 30a is greater than the number of turns of the second coil of the second actuator 30b. In other words, when control signals having the same signal values are applied to the first actuator 30a and the second actuator 30b, the torque applied to the magnet rotor 32 of the first actuator 30a is greater than the torque applied to the magnet rotor 32 of the second actuator 30b.

The signal value of the second control signal in the +direction shown in FIG. 16A is H21 and the duration during which the second control signal is applied to the first actuator 30a and the second actuator 30b is T13. The signal value of the first control signal in the +direction shown in FIG. 16B is H11 and the duration during which the first control signal is applied to the first actuator 30a and the second actuator 30b is T23.

The moving speed of the shutter 35 of the second actuator 30b is high. For this reason, the duration T13 during which the second control signal shown in FIG. 16A continues is long enough to switch positions of the shutter 35 of the second actuator 30b. The number of turns of the second coil of the second actuator 30b is small. However, since the signal value of the second control signal shown in FIG. 16A is high, the torque applied to the magnet rotor 32 of the second actuator 30b by the second control signal is large enough to switch positions of the shutter 35 of the second actuator 30b. Consequently, when the second control signal shown in FIG. 16A is applied to the second actuator 30b, positions of the shutter 35 of the second actuator 30b are switched.

The moving speed of the shutter 35 of the first actuator 30a is low. For this reason, the duration T13 during which the second control signal shown in FIG. 16A continues is not long enough to switch positions of the shutter 35 of the first actuator 30a. The number of turns of the first coil of the first actuator 30a is large and the signal value of the second control signal shown in FIG. 16A is high. For this reason, the torque applied to the magnet rotor 32 of the first actuator 30a by the second control signal shown in FIG. 16A is large enough to switch positions of the shutter 35 of the first actuator 30a. Consequently, when the second control signal shown in FIG. 16A is applied to the first actuator 30a, positions of the shutter 35 of the first actuator 30a are not switched.

The moving speed of the shutter 35 of the second actuator 30b is high. For this reason, the duration T23 during which the first control signal shown in FIG. 16B continues is long enough to switch positions of the shutter 35 of the second actuator 30b. The number of turns of the second coil of the second actuator 30b is small and the signal value of the first control signal shown in FIG. 16B is low. For this reason, the torque applied to the magnet rotor 32 of the second actuator 30b by the first control signal shown in FIG. 16B is not large enough to switch positions of the shutter 35 of the second actuator 30b. Consequently, when the first control signal shown in FIG. 16B is applied to the second actuator 30b, positions of the shutter 35 of the second actuator 30b are not switched.

The moving speed of the shutter 35 of the first actuator 30a is low. However, the duration T23 during which the first control signal shown in FIG. 16B continues is long enough to switch positions of the shutter 35 of the first actuator 30a. The signal value of the first control signal shown in FIG. 16B is low. However, since the number of turns of the first coil of the first actuator 30a is large, the torque applied to the magnet rotor 32 of the first actuator 30a by the first control signal shown in FIG. 16B is large enough to switch positions of the shutter 35 of the first actuator 30a. Consequently, when the first control signal shown in FIG. 16B is applied to the first actuator 30a, positions of the shutter 35 of the first actuator 30a are switched.

As described above, the endoscope device 1 is able to switch positions of the shutter 35 of the first actuator 30a and positions of the shutter 35 of the second actuator 30b independently in accordance with the signal value and the application duration of the control signal.

The endoscope device 1 according to the fifth embodiment continuously applies the first control signal having the small first signal value to the first actuator 30a and the second actuator 30b for a long duration. In this way, the endoscope device 1 according to the fifth embodiment is able to switch positions of only the shutter 35 of the first actuator 30a. In addition, the endoscope device 1 according to the fifth embodiment continuously applies the second control signal having the large second signal value to the first actuator 30a and the second actuator 30b for a short duration. In this way, the endoscope device 1 according to the fifth embodiment is able to switch positions of only the shutter 35 of the second actuator 30b. In other words, the endoscope device 1 according to the fifth embodiment is able to selectively and exclusively switch positions of the shutter 35 of the first actuator 30a and the second actuator 30b.

The first actuator 30a and the second actuator 30b are connected in series to each other. For this reason, the control signal output to the signal line 51 and the control signal applied to each actuator are the same.

The first actuator 30a to which the first control signal in the +direction having the first signal value is applied for longer than or equal to the first application duration moves the shutter 35 to a position to cover the second opening OP2. In addition, the first actuator 30a to which the first control signal in the −direction having the first signal value is applied for longer than or equal to the first application duration moves the shutter 35 to a position to cover the first opening OP1. When the second control signal having the second signal value is applied to the first actuator 30a for longer than or equal to the second application duration and shorter than the first application duration, the shutter 35 of the first actuator 30a does not move.

When the first control signal having the first signal value is applied to the second actuator 30b, the shutter 35 of the second actuator 30b does not move. In order to switch positions of the shutter 35 of the second actuator 30b, the second control signal having the second signal value greater than the first signal value needs to be applied to the second actuator 30b. The second actuator 30b to which the second control signal in the +direction having the second signal value is applied for longer than or equal to the second application duration moves the shutter 35 to a position to cover the fourth opening OP4. In addition, the second actuator 30b to which the second control signal in the −direction having the second signal value is applied for longer than or equal to the second application duration moves the shutter 35 to a position to cover the third opening OP3.

Figure 17:
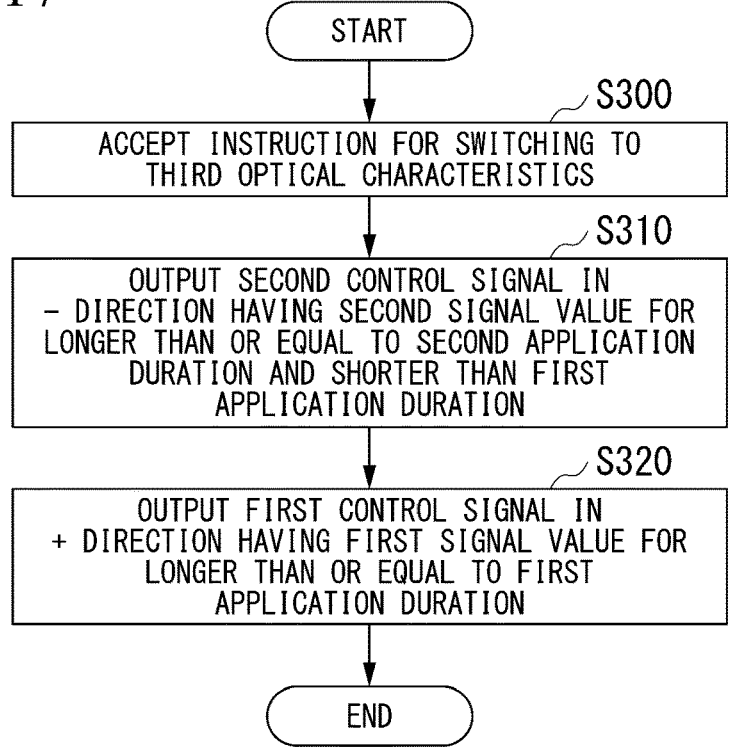
FIG. 17 is a flow chart showing a procedure of an operation of the endoscope device according to the fifth embodiment of the present invention.

FIG. 17 shows a procedure of an operation of the endoscope device 1. In FIG. 17, an operation of the endoscope device 1 is shown when the optical characteristics of the endoscope device 1 are switched from the second optical characteristics to the third optical characteristics. FIGS. 18A to 18C show the change of the optical characteristics in the operation shown in FIG. 17. In FIGS. 18A to 18C, the optical systems 21 to 26 are not shown.

Before the processing shown in FIG. 17 is executed, the shutter 35 of the first actuator 30a covers the first opening OP1 and the shutter 35 of the second actuator 30b covers the fourth opening OP4 as shown in FIG. 18A. When a user inputs an instruction for switching optical characteristics through the operation unit 4a, switching of the optical characteristics is executed. The operation unit 4a outputs the instruction input by a user to the control circuit 42. At this time, the control circuit 42 accepts an instruction for switching to the third optical characteristics (Step S300).

After Step S300, the control circuit 42 causes the signal source 41 to generate the second control signal in the −direction having the second signal value. The signal source 41 generates the second control signal and continuously outputs the generated second control signal to the signal line 51 for longer than or equal to the second application duration and shorter than the first application duration. In this way, the second control signal is applied to the first actuator 30a and the second actuator 30b (Step S310).

When Step S310 is executed, the shutter 35 of the second actuator 30b moves. The duration during which the second control signal is applied to the first actuator 30a is shorter than the first application duration. For this reason, the shutter 35 of the first actuator 30a does not move. Consequently, as shown in FIG. 18B, the shutter 35 of the first actuator 30a covers the first opening OP1 and the shutter 35 of the second actuator 30b covers the third opening OP3. In this way, the optical characteristics of the endoscope device 1 becomes the fourth optical characteristics.

After Step S310, the control circuit 42 causes the signal source 41 to generate the first control signal in the +direction having the first signal value. The signal source 41 generates the first control signal and outputs the generated first control signal to the signal line 51 for longer than or equal to the first application duration. In this way, the first control signal is applied to the first actuator 30a and the second actuator 30b (Step S320).

When Step S320 is executed, the shutter 35 of the first actuator 30a moves. The driving force of the shutter 35 generated in the second actuator 30b by the first control signal is not large enough to move the shutter 35. For this reason, the shutter 35 of the second actuator 30b does not move. Consequently, as shown in FIG. 18C, the shutter 35 of the first actuator 30*a* covers the second opening OP2 and the shutter 35 of the second actuator 30*b* covers the third opening OP3. In this way, the optical characteristics of the endoscope device 1 becomes the third optical characteristics.

Therefore, the signal source 41 applies the second control signal having the second signal value to the first actuator 30*a* and the second actuator 30*b* through the signal line 51 for longer than or equal to the second application duration and shorter than the first application duration in a first period in which Step S310 is executed. The signal source 41 applies the first control signal having the first signal value to the first actuator 30*a* and the second actuator 30*b* through the signal line 51 for longer than or equal to the first application duration in a second period in which Step S320 is executed.

Figure 19A:
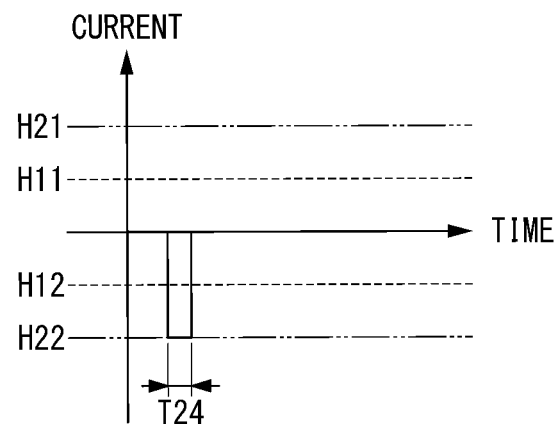
FIG. 19A is a diagram showing a waveform of a control signal applied to the actuator in the endoscope device according to the fifth embodiment of the present invention.
Figure 19B:
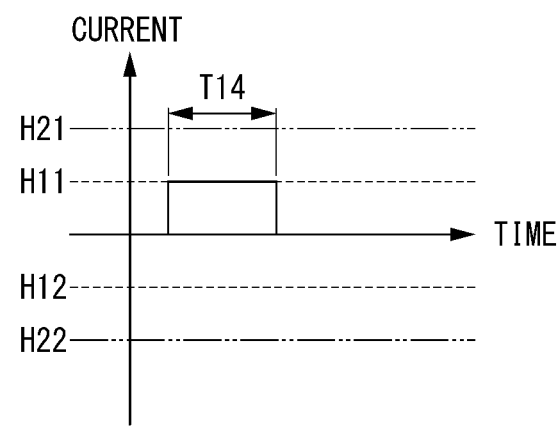
FIG. 19B is a diagram showing a waveform of a control signal applied to the actuator in the endoscope device according to the fifth embodiment of the present invention.

FIG. 19A shows a waveform of the second control signal applied to the first actuator 30*a* and the second actuator 30*b* in Step S310. FIG. 19B shows a waveform of the first control signal applied to the first actuator 30*a* and the second actuator 30*b* in Step S320. The horizontal axis in each drawing represents time and the vertical axis in each drawing represents current.

As shown in FIG. 19A, the signal value of the second control signal in the −direction is H22 and the duration during which the second control signal is applied to the first actuator 30*a* and the second actuator 30*b* is T24. The signal value of the second control signal in the +direction not shown in FIG. 19A is H21 and the duration during which the second control signal is applied to the first actuator 30*a* and the second actuator 30*b* is T24.

As shown in FIG. 19B, the signal value of the first control signal in the +direction is H11 and the duration during which the first control signal is applied to the first actuator 30*a* and the second actuator 30*b* is T14. The signal value of the first control signal in the −direction not shown in FIG. 19B is H12 and the duration during which the first control signal is applied to the first actuator 30*a* and the second actuator 30*b* is T14. The duration T24 is shorter than the duration T14.

The shutter 35 of the second actuator 30*b* to which the second control signal is applied in Step S310 moves to a position to cover the third opening OP3. The shutter 35 of the first actuator 30*a* to which the first control signal is applied in Step S320 moves to a position to cover the second opening OP2. According to the operation shown in FIG. 17, the optical characteristics of the endoscope device 1 are switched from the second optical characteristics to the third optical characteristics specified by a user.

In this way, when a user inputs the instruction for switching optical characteristics through the operation unit 4*a*, the control signal in accordance with the instruction is applied to the first actuator 30*a* and the second actuator 30*b*. Consequently, the optical characteristics of the endoscope device 1 are switched to the desired optical characteristics.

Either the first control signal or the second control signal may be applied to the first actuator 30*a* and the second actuator 30*b* first. When the second control signal having the second signal value is applied to the first actuator 30*a* and the second actuator 30*b* for longer than or equal to the second application duration and shorter than the first application duration, positions of only the shutter 35 of the second actuator 30*b* are switched. When the first control signal having the first signal value is applied to the first actuator 30*a* and the second actuator 30*b* for longer than or equal to the first application duration, positions of only the shutter 35 of the first actuator 30*a* are switched. For this reason, after the two control signals are applied to the first actuator 30*a* and the second actuator 30*b* in any order, the optical characteristics of the endoscope device 1 are switched to the third optical characteristics.

Instead of the endoscope device 1 according to the first embodiment, the endoscope device 1*b* according to the third embodiment may be used. The resistance value of the resistor R3 is less than the resistance value of the resistor R4. For example, the signal source 41 applies the second control signal having the second signal value to the second actuator 30*b* through the signal line 55 for longer than or equal to the second application duration and shorter than the first application duration in the first period in which Step S310 shown in FIG. 17 is executed. In addition, the signal source 41 applies the second control signal having a signal value greater than the second signal value to the first actuator 30*a* for longer than or equal to the second application duration and shorter than the first application duration in the first period.

When Step S310 is executed, the shutter 35 of the second actuator 30*b* moves. The duration during which the second control signal is applied to the first actuator 30*a* is shorter than the first application duration. For this reason, the shutter 35 of the first actuator 30*a* does not move.

The signal source 41 applies the first control signal having the first signal value to the first actuator 30*a* through the signal line 55 for longer than or equal to the first application duration in the second period in which Step S320 shown in FIG. 17 is executed. In addition, the signal source 41 applies the first control signal having the third signal value less than the first signal value to the second actuator 30*b* through the signal line 55 for longer than or equal to the first application duration in the second period. The third signal value is less than the second value. The third signal value may be less than the first value.

When Step S320 is executed, the shutter 35 of the first actuator 30*a* moves. The driving force of the shutter 35 generated in the second actuator 30*b* by the first control signal is not large enough to move the shutter 35. For this reason, the shutter 35 of the second actuator 30*b* does not move.

The instruction for switching optical characteristics does not need to be input through the operation unit 4*a*. In other words, the processing in Step S300 is not essential. For example, a program defining the procedure of switching predetermined optical characteristics may be stored on a memory of the endoscope device 1 in advance. The control circuit 42 may read the program from the memory and may execute the processing in Step S310 and Step S320 in accordance with the program.

In the fifth embodiment, effects similar to the effects in the first embodiments are obtained. In addition, the endoscope device 1 according to the fifth embodiment is able to switch positions of the shutter 35 of the first actuator 30*a* and positions of the shutter 35 of the second actuator 30*b* independently.

(Sixth Embodiment)

Figure 20:
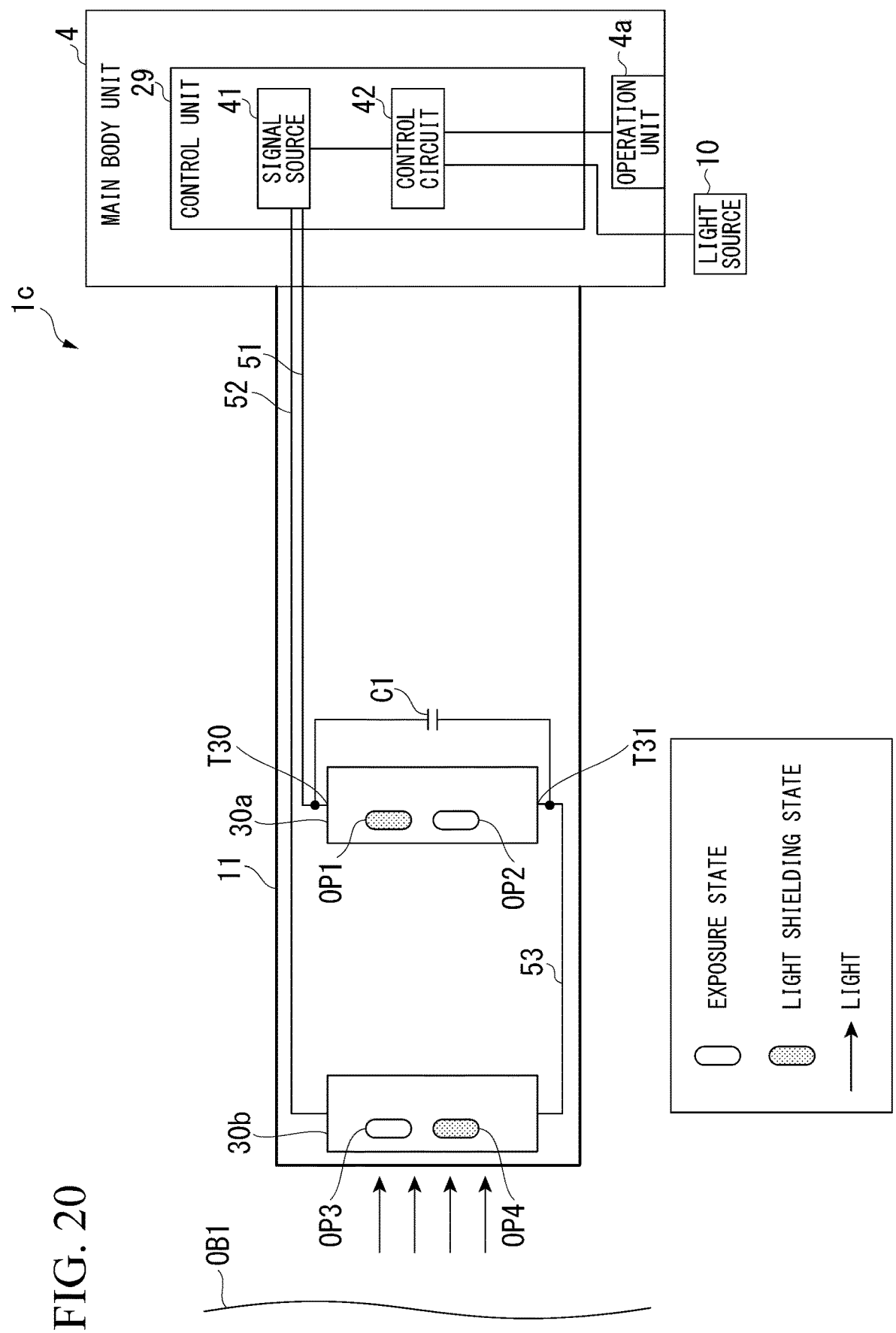
FIG. 20 is a block diagram showing a configuration of an endoscope device according to a sixth embodiment of the present invention.

FIG. 20 shows a configuration of an endoscope device 1*c* according to a sixth embodiment of the present invention. In terms of the configuration shown in FIG. 20, differences from the configuration shown in FIG. 2 will be described.

In FIG. 20, the optical systems 21 to 26 are not shown. The endoscope device 1*c* includes a condenser C1 connected to the signal line 51 in parallel with the first actuator 30*a*. The condenser C1 is connected to the signal line 51 and the signal line 53. The first actuator 30*a* includes a first terminal T30 and a second terminal T31. The condenser C1 is electrically connected to the first terminal T30 and the second terminal T31 of the first actuator 30*a*. The first actuator 30a and the condenser C1 are connected in parallel to the signal line 51 and the signal line 53.

In the endoscope device 1 according to the fifth embodiment, the weight of the shutter 35 of the first actuator 30a and the weight of the shutter 35 of the second actuator 30b are different from each other. Alternatively, a lubricant such as grease is applied to the shutter 35 of at least one of the first actuator 30a and the second actuator 30b. In the endoscope device 1c according to the sixth embodiment, the weight of the shutter 35 of the first actuator 30a and the weight of the shutter 35 of the second actuator 30b may be the same. In the endoscope device 1c according to the sixth embodiment, the number of turns of the first coil of the first actuator 30a is greater than the number of turns of the second coil of the second actuator 30b.

In terms of points other than the above, the configuration shown in FIG. 20 is similar to the configuration shown in FIG. 2.

Since the condenser C1 is connected to the signal line 51 in parallel with the first actuator 30a, a waveform of a control signal flowing in the first actuator 30a becomes dull due to the influence of the condenser C1. In other words, the waveform of the control signal deteriorates. For this reason, the waveform of the control signal flowing in the first actuator 30a and the waveform of the control signal flowing in the second actuator 30b are different from each other.

The capacity of the condenser C1 is set such that positions of the shutter 35 of the first actuator 30a are switched when the first control signal in a predetermined direction having the first signal value is continuously applied to the first actuator 30a for longer than or equal to the first application duration. In addition, the capacity of the condenser C1 is set such that positions of the shutter 35 of the first actuator 30a are not switched when the second control signal in a predetermined direction having the second signal value is continuously applied to the second actuator 30b for longer than or equal to the second application duration and shorter than the first application duration.

The control signal output from the signal source 41 in the endoscope device 1c according to the sixth embodiment is similar to the control signal output from the signal source 41 in the endoscope device 1 according to the fifth embodiment. However, the waveform of the control signal flowing in the first actuator 30a of the endoscope device 1c according to the sixth embodiment is different from the waveform of the control signal flowing in the first actuator 30a of the endoscope device 1 according to the fifth embodiment due to the influence of the condenser C1.

Figure 21A:
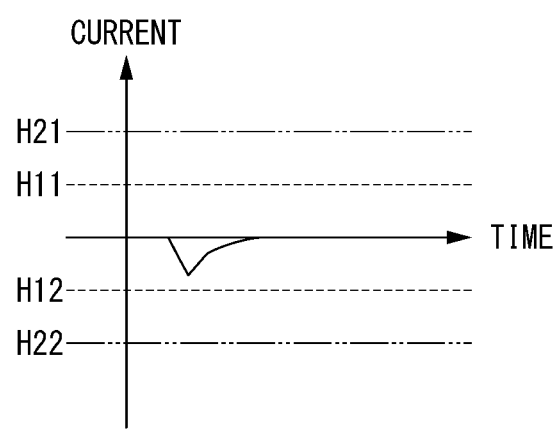
FIG. 21A is a diagram showing a waveform of a control signal applied to an actuator in the endoscope device according to the sixth embodiment of the present invention.
Figure 21B:
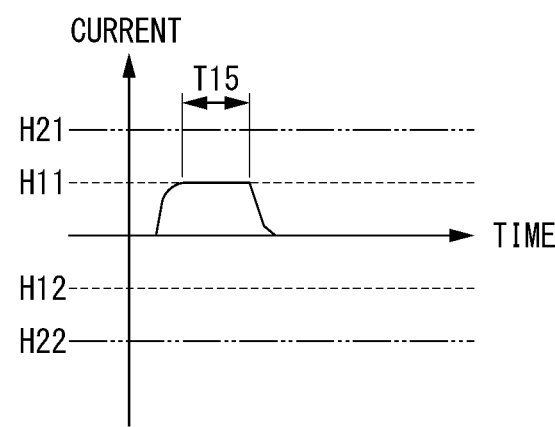
FIG. 21B is a diagram showing a waveform of a control signal applied to the actuator in the endoscope device according to the sixth embodiment of the present invention.

The waveform of the control signal flowing in the first actuator 30a when the endoscope device 1c operates in accordance with the procedure shown in FIG. 17 will be described. FIG. 21A shows a waveform of the control signal applied to the first actuator 30a in Step S310. FIG. 21B shows a waveform of the control signal applied to the first actuator 30a in Step S320. The horizontal axis in each drawing represents time and the vertical axis in each drawing represents current.

In Step S310, the second control signal in the −direction having the second signal value is continuously output to the signal line 51 for longer than or equal to the second application duration and shorter than the first application duration. At this time, the waveform of the second control signal applied to the second actuator 30b is similar to the waveform shown in FIG. 19A. The shutter 35 of the second actuator 30b to which the second control signal is applied moves to a position to cover the third opening OP3.

The control signal applied to the first actuator 30a changes later than the second control signal shown in FIG. 19A due to accumulation of electric charge to the condenser C1 or discharge of electric charge from the condenser C1. As shown in FIG. 19A, the signal value of the second control signal applied to the second actuator 30b changes from 0 to H22. For this reason, as shown in FIG. 21A, the signal value of the control signal applied to the first actuator 30a gently changes from 0 toward H22. When the signal value of the second control signal applied to the second actuator 30b changes from H22 to 0, the signal value of the control signal applied to the first actuator 30a has not reached H12. The signal value of the control signal applied to the first actuator 30a gently changes toward 0 due to the change of the second control signal applied to the second actuator 30b.

As shown in FIG. 21A, the signal value of the control signal applied to the first actuator 30a is less than H12 due to the influence of the condenser C1. The control signal having the signal value less than the first value is continuously applied to the first actuator 30a for shorter than the first application duration. The driving force of the shutter 35 generated in the first actuator 30a by the control signal is not large enough to move the shutter 35. For this reason, the shutter 35 of the first actuator 30a does not move.

In Step S320, the first control signal in the +direction having the first signal value is continuously output to the signal line 51 for longer than or equal to the first application duration. At this time, the waveform of the first control signal applied to the second actuator 30b is similar to the waveform shown in FIG. 19B. The shutter 35 of the second actuator 30b to which the first control signal is applied does not move.

As shown in FIG. 19B, the signal value of the first control signal applied to the second actuator 30b changes from 0 to H11. For this reason, as shown in FIG. 21B, the signal value of the control signal applied to the first actuator 30a gently changes from 0 toward H11. Before the duration T14 during which the first control signal is applied to the second actuator 30b passes by, the signal value of the control signal applied to the first actuator 30a becomes H11. When the signal value of the first control signal applied to the second actuator 30b changes from H11 to 0, the signal value of the control signal applied to the first actuator 30a gently changes toward 0.

As shown in FIG. 21B, the waveform of the control signal applied to the first actuator 30a becomes dull due to the influence of the condenser C1. However, the signal value of the control signal applied to the first actuator 30a reaches H11. The capacity of the condenser C1 is set such that a duration T15 during which the signal value of the control signal is H11 is longer than or equal to the first application duration. In this way, the shutter 35 of the first actuator 30a to which the control signal is applied moves to a position to cover the second opening OP2. According to the above-described operation, the optical characteristics of the endoscope device 1c are switched from the second optical characteristics to the third optical characteristics specified by a user.

Either the first control signal or the second control signal may be applied to the first actuator 30a and the second actuator 30b first. When the second control signal having the second signal value is applied to the first actuator 30a and the second actuator 30b, positions of only the shutter 35 of the second actuator 30b are switched. When the first control signal having the first signal value is applied to the first actuator 30a and the second actuator 30b, positions of only the shutter 35 of the first actuator 30a are switched. For this reason, after the two control signals are applied to the first actuator 30a and the second actuator 30b in any order, the optical characteristics of the endoscope device 1c are switched to the third optical characteristics.

In the sixth embodiment, the following effects are obtained in addition to the effects of the fifth embodiment. In the endoscope device 1c according to the sixth embodiment, the condenser C1 is connected to the signal line 51 in parallel with the first actuator 30a. For this reason, effects similar to the effects in the fifth embodiments are obtained regardless of the difference between the weights of the shutters 35 of the two actuators, or regardless of the method of applying grease or the like to the shutter 35 of at least one of the two actuators. Adding the condenser C1 in a manufacturing process is easier than adjusting the weight of the shutter 35, applying grease to the shutter 35, or the like. For this reason, manufacturing the endoscope device 1c according to the sixth embodiment is easier than manufacturing the endoscope device 1 according to the fifth embodiment.

(Seventh Embodiment)

Figure 22:
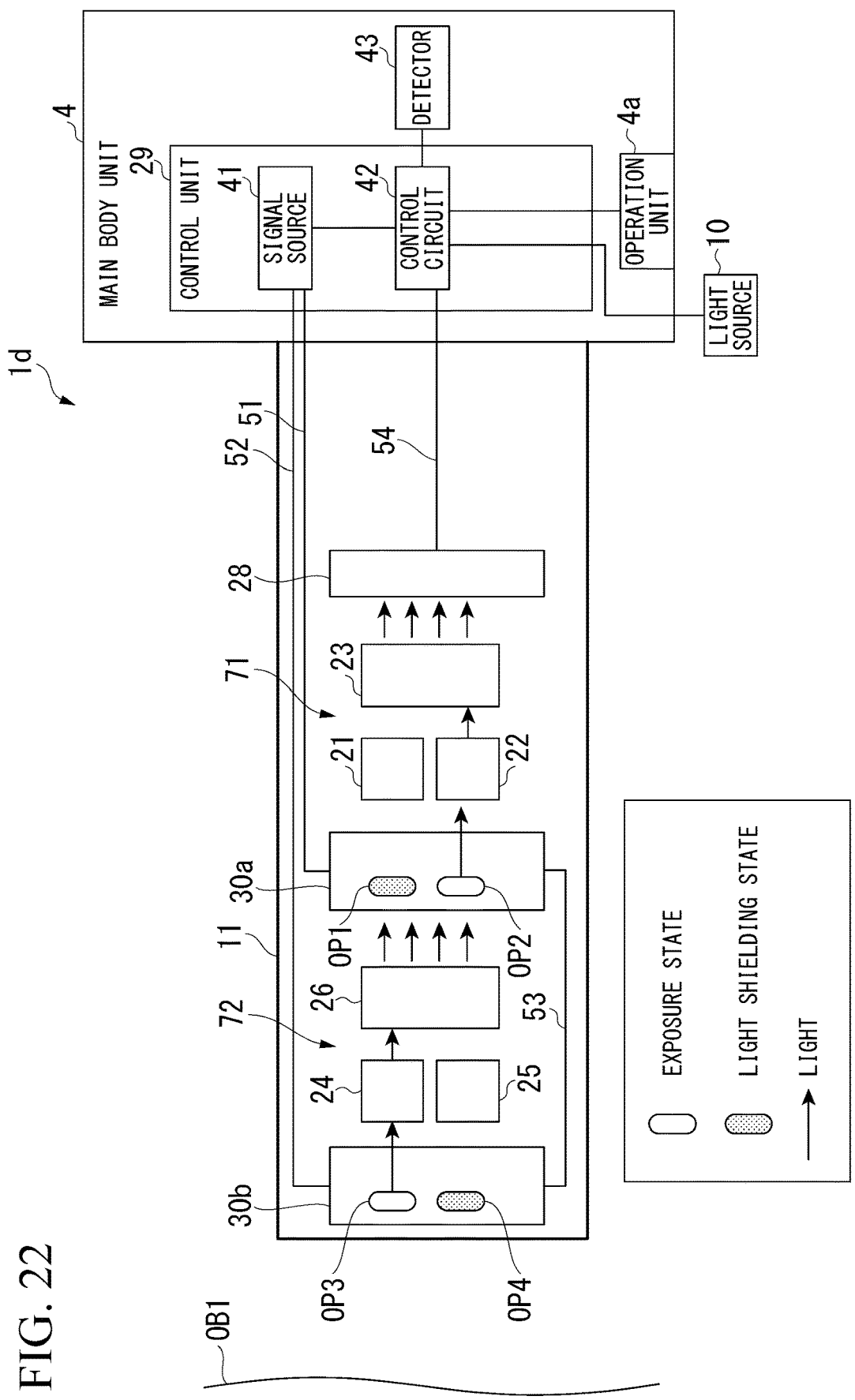
FIG. 22 is a block diagram showing a configuration of an endoscope device according to a seventh embodiment of the present invention.

FIG. 22 shows a configuration of an endoscope device 1d according to a seventh embodiment of the present invention. In terms of the configuration shown in FIG. 22, differences from the configuration shown in FIG. 2 will be described.

The main body unit 4 includes a detector 43 in addition to the configuration shown in FIG. 2. The detector 43 detects positions of the first optical member and the second optical member. In other words, the detector 43 detects positions of the shutters 35 of the first actuator 30a and the second actuator 30b. The control circuit 42 controls the signal source 41 such that the state of the endoscope device 1d becomes any one of a first state and a second state on the basis of the positions detected by the detector 43. The first state is a state in which the first control signal is continuously applied to the first actuator 30a and the second actuator 30b for longer than or equal to the first application duration. The second state is a state in which the second control signal is continuously applied to the first actuator 30a and the second actuator 30b for longer than or equal to the second application duration and shorter than the first application duration.

For example, the detector 43 is an image processing circuit including a processor or the like. The detector 43 detects a position of the shutter 35 on the basis of an imaging signal generated by the imaging device 28. For example, a mark is disposed on each of four optical paths that are switched by the shutters 35 of the first actuator 30a and the second actuator 30b. The shapes or the like of the four marks are different from each other so as to identify each optical path. An optical image of the mark is formed at a position around a light receiving surface of the imaging device 28. The detector 43 detects the mark from the imaging signal through image processing. The mark corresponding to the optical path through which light from the subject OB1 passes is detected. The detector 43 detects a position of the shutter 35 on the basis of the detected mark.

The first actuator 30a and the second actuator 30b may include a detector such as a magnetic sensor. The detector disposed in each of the first actuator 30a and the second actuator 30b detects a position of the shutter 35 by detecting the change of magnetism of, for example, a magnetic substance disposed in the shutter 35. As long as the detector is able to detect a position of the shutter 35, the detector may be constituted in any way.

In terms of points other than the above, the configuration shown in FIG. 22 is similar to the configuration shown in FIG. 2.

It is possible to provide the endoscope device 1d according to the seventh embodiment by disposing the detector 43 and changing the method of applying a control signal for any one of the endoscope devices according to the first to sixth embodiments. Hereinafter, the difference between the endoscope device 1d according to the seventh embodiment and the endoscope device 1 according to the fifth embodiment will be mainly described.

The advantage of detecting optical characteristics by using the detector 43 will be described. When the shock is applied to the tip end part 12 of the insertion unit 11, there are cases in which positions of the shutter 35 of the actuator mounted in the tip end part 12 of the insertion unit 11 are switched regardless of a state of a control signal. In order for an endoscope device not including the detector 43 to surely switch its optical characteristics to the desired state, the endoscope device needs to apply a control signal such that positions of the shutters 35 of all the actuators are switched to the desired positions.

If it is possible to detect that the position of the shutter 35 is the desired position before switching positions of the shutter 35, it is unnecessary to apply a control signal. Since there are cases in which positions of the shutter 35 of the actuator are unintentionally switched due to the above-described shock or the like, the endoscope device not including the detector 43 also applies a control signal that may not need to be applied.

The endoscope device 1d including the detector 43 is able to detect positions of the shutters 35 of the first actuator 30a and the second actuator 30b by using the detector 43. For this reason, the endoscope device 1d does not apply a control signal for moving the shutter 35 of which positions are unnecessary to be switched. In this way, there are cases in which the number of times the endoscope device 1d applies a control signal in order to switch its optical characteristics decreases, compared to the endoscope device 1 according to the fifth embodiment.

Figure 23:
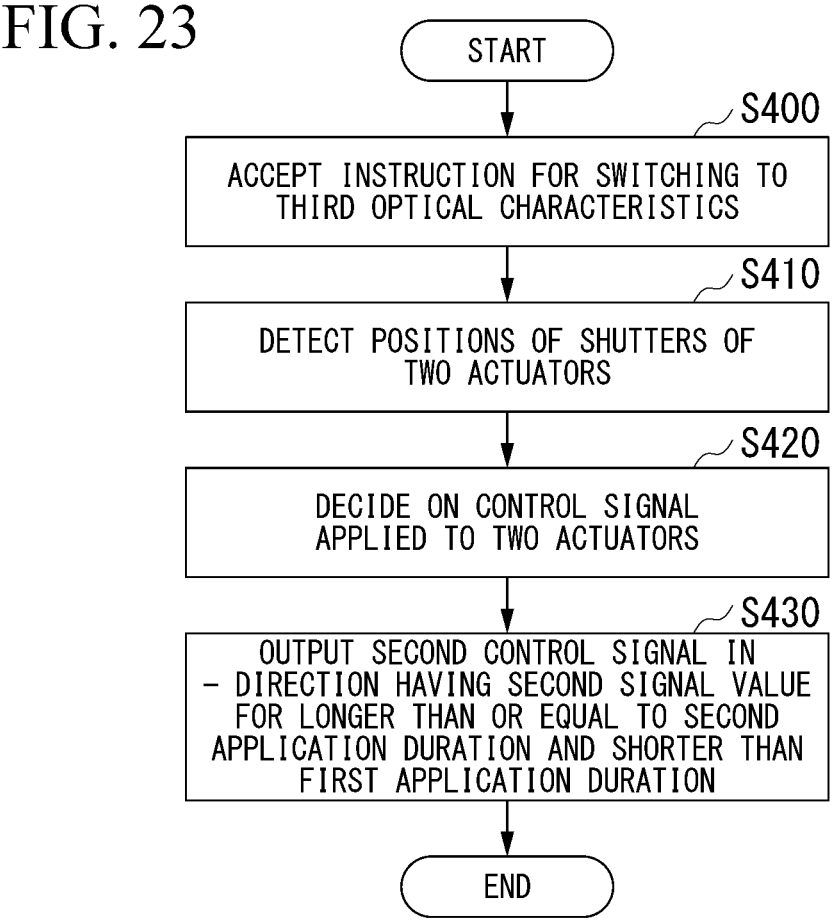
FIG. 23 is a flow chart showing a procedure of an operation of the endoscope device according to the seventh embodiment of the present invention.
Figure 24A:
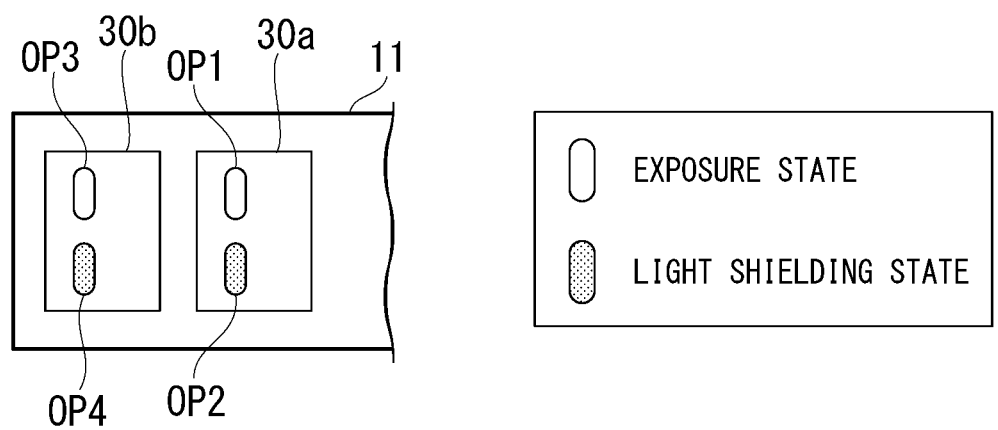
FIG. 24A is a diagram showing optical characteristics in the endoscope device according to the seventh embodiment of the present invention.
Figure 24B:
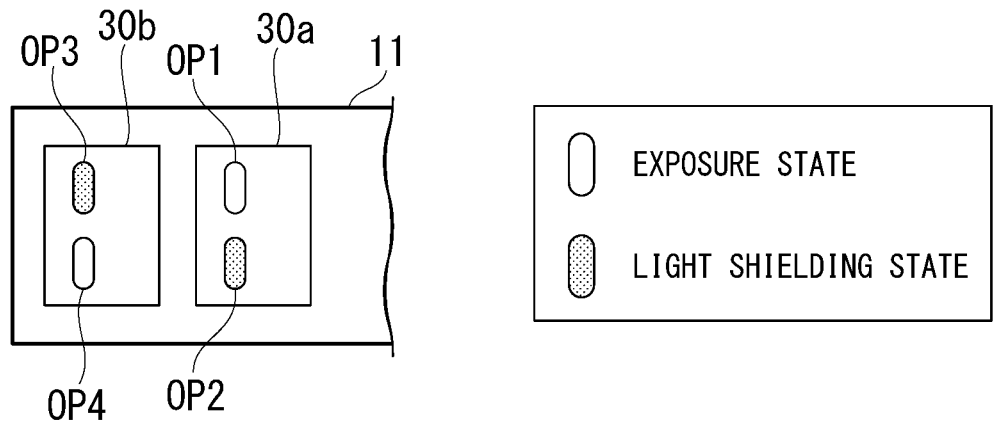
FIG. 24B is a diagram showing optical characteristics in the endoscope device according to the seventh embodiment of the present invention.

FIG. 23 shows a procedure of an operation of the endoscope device 1d according to the seventh embodiment. In FIG. 23, an operation of the endoscope device 1d is shown when the optical characteristics of the endoscope device 1d are switched from the first optical characteristics to the third optical characteristics. FIGS. 24A and 24B show the change of the optical characteristics in the operation shown in FIG. 23. In FIGS. 24A and 24B, the optical systems 21 to 26 are not shown.

Before the processing shown in FIG. 23 is executed, the shutter 35 of the first actuator 30a covers the second opening OP2 and the shutter 35 of the second actuator 30b covers the fourth opening OP4 as shown in FIG. 24A. When a user inputs an instruction for switching optical characteristics through the operation unit 4a, switching of the optical characteristics is executed. The operation unit 4a outputs the instruction input by a user to the control circuit 42. At this time, the control circuit 42 accepts an instruction for switching to the third optical characteristics (Step S400).

After Step S400, the control circuit 42 causes the detector 43 to detect positions of the shutters 35 of the first actuator 30a and the second actuator 30b. In this way, the detector 43 detects positions of the shutters 35 of the first actuator 30a and the second actuator 30b and notifies the control circuit 42 of a detection result (Step S410).

After Step S410, the control circuit 42 decides on a control signal to be applied to the first actuator 30a and the second actuator 30b on the basis of the positions detected in Step S410 (Step S420). The control circuit 42 determines to move the shutter 35 of the second actuator 30b in order to switch the optical characteristics of the endoscope device 1d from the first optical characteristics to the third optical characteristics in Step S420.

After Step S420, the control circuit 42 causes the signal source 41 to generate the second control signal in the −direction having the second signal value. The signal source 41 generates the second control signal and continuously outputs the generated second control signal to the signal line 51 for longer than or equal to the second application duration and shorter than the first application duration. In this way, the second control signal is applied to the first actuator 30a and the second actuator 30b (Step S430). In this way, the control circuit 42 controls the signal source 41 such that the state of the endoscope device 1d becomes the second state.

When Step S430 is executed, the shutter 35 of the second actuator 30b moves. The duration during which the second control signal is applied to the first actuator 30a is shorter than the first application duration. For this reason, the shutter 35 of the first actuator 30a does not move. Consequently, as shown in FIG. 24B, the shutter 35 of the first actuator 30a covers the second opening OP2 and the shutter 35 of the second actuator 30b covers the third opening OP3. In this way, the optical characteristics of the endoscope device 1d becomes the third optical characteristics.

Figure 25:
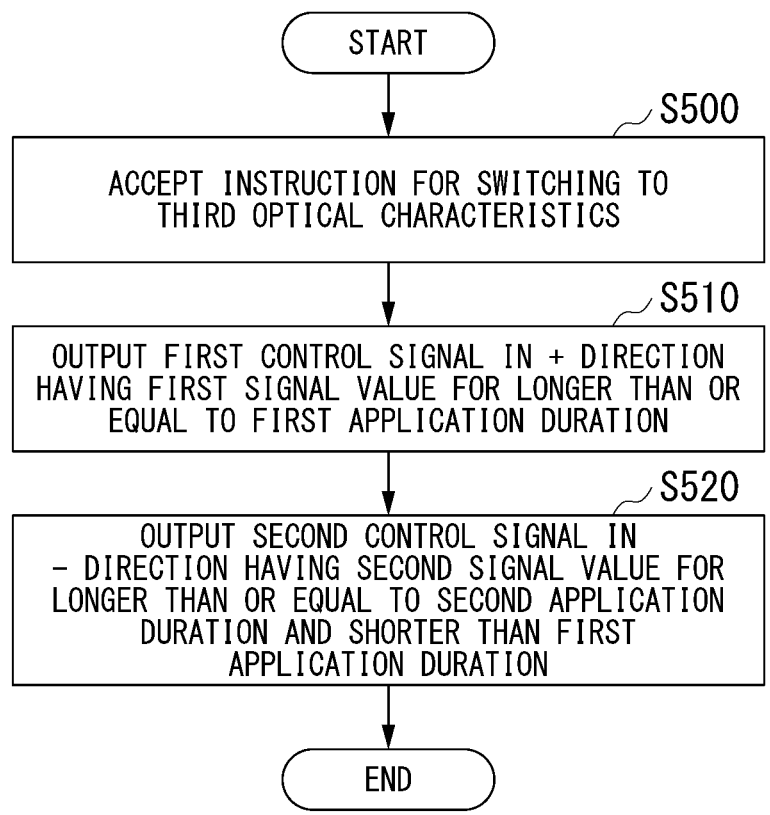
FIG. 25 is a flow chart showing a procedure of an operation of the endoscope device according to the fifth embodiment of the present invention.
Figure 26A:
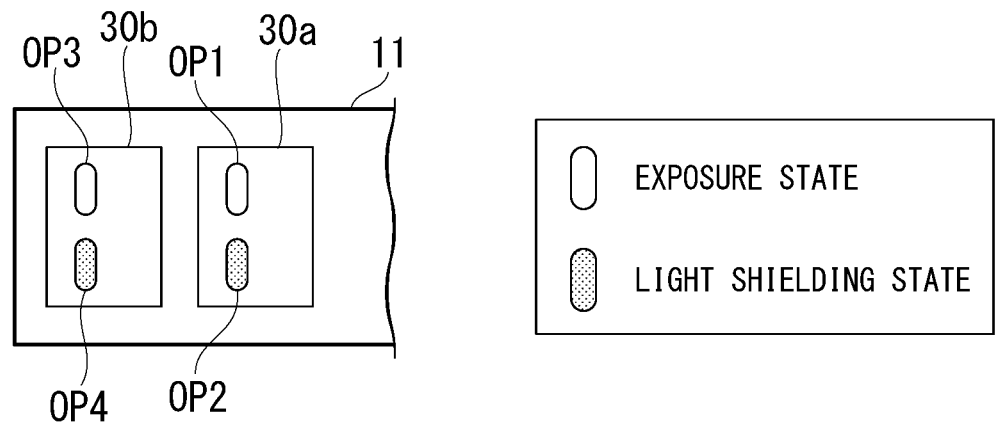
FIG. 26A is a diagram showing optical characteristics in the endoscope device according to the fifth embodiment of the present invention.
Figure 26B:
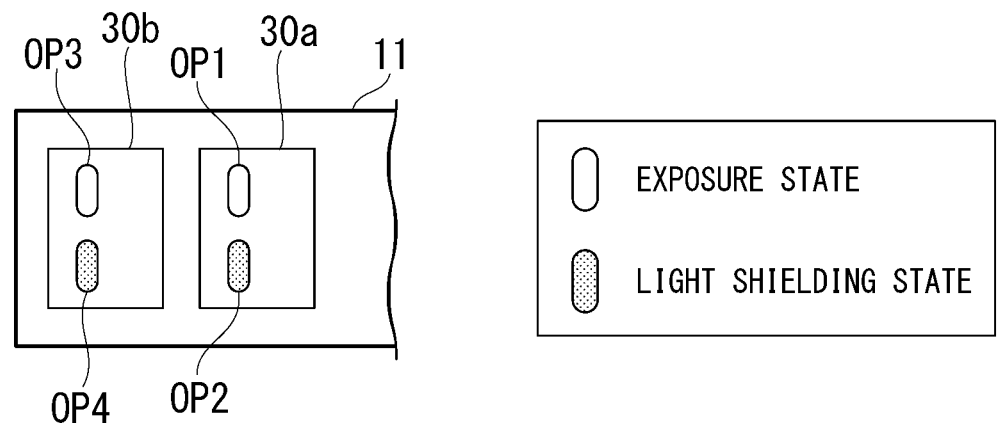
FIG. 26B is a diagram showing optical characteristics in the endoscope device according to the fifth embodiment of the present invention.
Figure 26C:
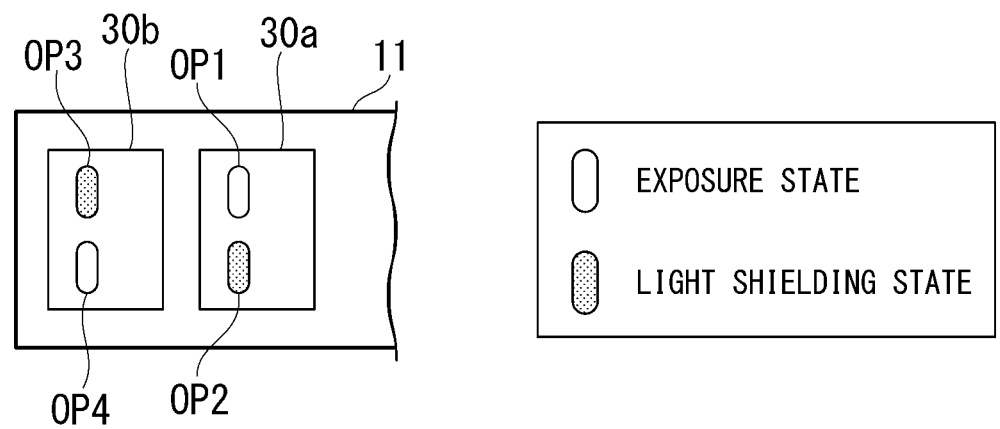
FIG. 26C is a diagram showing optical characteristics in the endoscope device according to the fifth embodiment of the present invention.

FIG. 25 shows a procedure of an operation of the endoscope device 1 according to the fifth embodiment. In FIG. 25, an operation of the endoscope device 1 is shown when the optical characteristics of the endoscope device 1 are switched from the first optical characteristics to the third optical characteristics. FIGS. 26A to 26C show the change of the optical characteristics in the operation shown in FIG. 25. In FIGS. 26A to 26C, the optical systems 21 to 26 are not shown.

Before the processing shown in FIG. 25 is executed, the shutter 35 of the first actuator 30a covers the second opening OP2 and the shutter 35 of the second actuator 30b covers the fourth opening OP4 as shown in FIG. 26A. This state is the same as the state shown in FIG. 24A. When a user inputs an instruction for switching optical characteristics through the operation unit 4a, switching of the optical characteristics is executed. The operation unit 4a outputs the instruction input by a user to the control circuit 42. At this time, the control circuit 42 accepts an instruction for switching to the third optical characteristics (Step S500).

After Step S500, the control circuit 42 causes the signal source 41 to generate the first control signal in the +direction having the first signal value. The signal source 41 generates the first control signal and continuously outputs the generated first control signal to the signal line 51 for longer than or equal to the first application duration. In this way, the first control signal is applied to the first actuator 30a and the second actuator 30b (Step S510).

The first control signal in the +direction is a signal for moving the shutter 35 of the first actuator 30a to the second opening OP2. Before Step S510 is executed, the shutter 35 of the first actuator 30a has already covered the second opening OP2. For this reason, when Step S510 is executed, the shutter 35 of the first actuator 30a does not move. The driving force of the shutter 35 generated in the second actuator 30b by the first control signal is not large enough to move the shutter 35. For this reason, the shutter 35 of the second actuator 30b does not move. In this way, as shown in FIG. 26B, the optical characteristics of the endoscope device 1 is kept in the third optical characteristics.

After Step S510, the control circuit 42 causes the signal source 41 to generate the second control signal in the −direction having the second signal value. The signal source 41 generates the second control signal and outputs the generated second control signal to the signal line 51 for longer than or equal to the second application duration and shorter than the first application duration. In this way, the second control signal is applied to the first actuator 30a and the second actuator 30b (Step S520).

When Step S520 is executed, the shutter 35 of the second actuator 30b moves. The duration during which the second control signal is applied to the first actuator 30a is shorter than the first application duration. For this reason, the shutter 35 of the first actuator 30a does not move. Consequently, as shown in FIG. 26C, the shutter 35 of the first actuator 30a covers the second opening OP2 and the shutter 35 of the second actuator 30b covers the third opening OP3. In this way, the optical characteristics of the endoscope device 1 becomes the third optical characteristics.

The endoscope device 1d according to the seventh embodiment detects states of the shutters 35 of the first actuator 30a and the second actuator 30b before positions of the shutters 35 of the first actuator 30a and the second actuator 30b are switched. In other words, the endoscope device 1d detects the optical characteristics of the endoscope device 1d before the optical characteristics are switched. In this way, the endoscope device 1d is able to generate only the control signal necessary for switching the optical characteristics.

The endoscope device 1 according to the fifth embodiment does not include the detector 43. In the endoscope device 1 according to the fifth embodiment, there are cases in which positions of the shutter 35 of the actuator are unintentionally switched due to the shock or the like. For this reason, the endoscope device not including the detector 43 also applies a control signal that may not need to be applied. In the example shown in FIG. 25, the first control signal in the +direction having the first signal value is applied to the first actuator 30a for longer than or equal to the first application duration. If it is possible to detect that the optical characteristics of the endoscope device 1 are the first optical characteristics, it is unnecessary to apply the first control signal.

In the seventh embodiment, the following effects are obtained in addition to the effects of the first to sixth embodiments. There are cases in which the number of times the endoscope device 1d applies a control signal in order to switch its optical characteristics decreases, compared to the number of times the endoscope device according to the first to sixth embodiments applies a control signal. For this reason, there are cases in which the power consumption of the endoscope device 1d decreases, compared to the power consumption of the endoscope device according to the first to sixth embodiments.

(First Modified Example of First to Seventh Embodiments)

A first modified example of the first to seventh embodiments will be described. In the first to seventh embodiments, the examples in which the control signal is a rectangular wave have been described. However, as long as it is possible to apply a control signal having a signal value within a predetermined range to a plurality of actuators for a predetermined duration, the control signal is not limited to a rectangular wave.

Figure 27A:
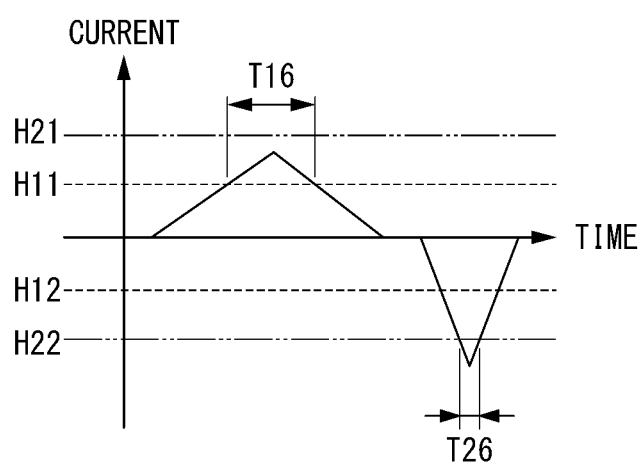
FIG. 27A is a diagram showing a waveform of a control signal in a first modified example of the first to seventh embodiments of the present invention.
Figure 27B:
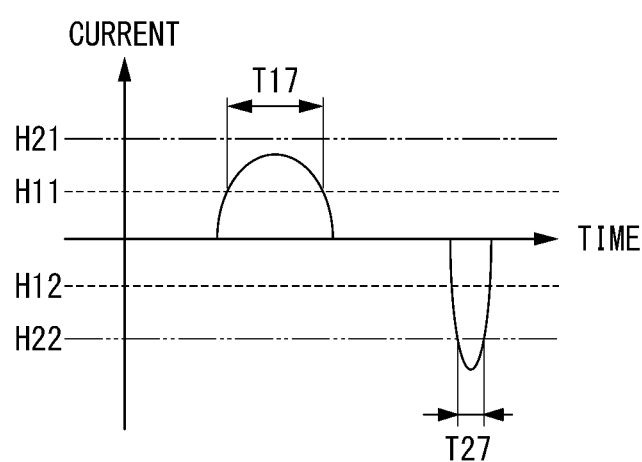
FIG. 27B is a diagram showing a waveform of a control signal in a first modified example of the first to seventh embodiments of the present invention.

FIG. 27A shows a waveform of a control signal that is a triangular wave. FIG. 27B shows a waveform of a control signal that is a sine wave. The horizontal axis in each drawing represents time and the vertical axis in each drawing represents current.

As shown in FIG. 27A, a first control signal in the +direction has a first signal value greater than H11 and less than H21. In addition, the duration during which the state in which the signal value of the first control signal is greater than H11 continues is T16. As shown in FIG. 27A, a second control signal in the −direction has a second signal value greater than H22. In addition, the duration during which the state in which the signal value of the second control signal is greater than H22 continues is T26. The duration T26 is shorter than the duration T16. The duration T26 and the duration T16 may be the same. Alternatively, the duration T26 may be longer than the duration T16.

As shown in FIG. 27B, a first control signal in the +direction has a first signal value greater than H11 and less than H21. In addition, the duration during which the state in which the signal value of the first control signal is greater than H11 continues is T17. As shown in FIG. 27B, a second control signal in the −direction has a second signal value greater than H22. In addition, the duration during which the state in which the signal value of the second control signal is greater than H22 continues is T27. The duration T27 is shorter than the duration T17. The duration T27 and the duration T17 may be the same. Alternatively, the duration T27 may be longer than the duration T17.

(Second Modified Example of First to Seventh Embodiments)

A second modified example of the first to seventh embodiments will be described. In the first to seventh embodiments, the two actuators and the control unit 29 are connected to each other by two signal lines. However, the number of signal lines connecting a plurality of actuators and the control unit 29 to each other is not limited to two.

For example, in the endoscope device of the related art in which three actuators are mounted in the tip end part of the insertion unit, the three actuators are connected to the control unit by a total of six signal lines. For example, in the endoscope device 1 according to the first embodiment, three actuators are connected to the control unit 29 by a total of two signal lines.

However, the three actuators may be connected to the control unit 29 by a total of four signal lines by modifying the configuration of the endoscope device 1 according to the first embodiment. In other words, two actuators are connected in series or in parallel to each other and are connected to the control unit 29 by two signal lines. The remaining one actuator may not be connected to the other two actuators and may be connected to the control unit 29 alone by the other two signal lines.

Even when the endoscope device 1 according to the first embodiment is constituted like this, the number of signal lines connecting a plurality of actuators and the control unit to each other decreases, compared to the endoscope device of the related art. Since the number of signal lines decreases, increase in thickness of the insertion unit 11 is restricted.

(Third Modified Example of First to Seventh Embodiments)

A third modified example of the first to seventh embodiments will be described. In the endoscope device according to the first to seventh embodiments, the optical systems 21 to 26, the first actuator 30a, the second actuator 30b, the first imaging optical system 71, and the second imaging optical system 72 are disposed in the tip end part 12 of the insertion unit 11. The optical systems 21 to 26, the first actuator 30a, the second actuator 30b, the first imaging optical system 71, and the second imaging optical system 72 may be disposed in an exchangeable optical adaptor. In the third modified example of the first to seventh embodiments, the tip end of the insertion unit 11 includes an optical adaptor. Hereinafter, three examples will be described.

FIG. 28 shows a configuration of an endoscope device 1e including an optical adaptor 2B. As shown in FIG. 28, the optical adaptor 2B is attached to the insertion unit 11. The optical adaptor 2B includes the optical systems 21 to 26, the first actuator 30a, the second actuator 30b, the first imaging optical system 71, and the second imaging optical system 72. The imaging device 28 is disposed in the tip end part 12 of the insertion unit 11.

FIG. 29 shows a configuration of an endoscope device 1f including an optical adaptor 2C. As shown in FIG. 29, the optical adaptor 2C is attached to the insertion unit 11. The optical adaptor 2C includes the optical systems 24 to 26, the second actuator 30b, and the second imaging optical system 72. The optical systems 21 to 23, the first actuator 30a, the first imaging optical system 71, and the imaging device 28 are disposed in the tip end part 12 of the insertion unit 11.

FIG. 30 shows a configuration of an endoscope device 1g including an optical adaptor 2D and an optical adaptor 2E. As shown in FIG. 30, the optical adaptor 2D is attached to the insertion unit 11 and the optical adaptor 2E is attached to the optical adaptor 2D. The optical adaptor 2D includes the optical systems 21 to 23, the first actuator 30a, and the first imaging optical system 71. The optical adaptor 2E includes the optical systems 24 to 26, the second actuator 30b, and the second imaging optical system 72. The imaging device 28 is disposed in the tip end part 12 of the insertion unit 11. The optical adaptor 2E may be attached to the insertion unit 11 and the optical adaptor 2D may be attached to the optical adaptor 2E.

(Fourth Modified Example of First to Seventh Embodiments)

A fourth modified example of the first to seventh embodiments will be described. The endoscope device according to the first to seventh embodiments switches a plurality of optical paths in the first imaging optical system 71 and the second imaging optical system 72. The endoscope device may switch optical paths within an illumination optical system by switching optical characteristics. In other words, the endoscope device may switch light beams emitted to a subject.

Figure 31:
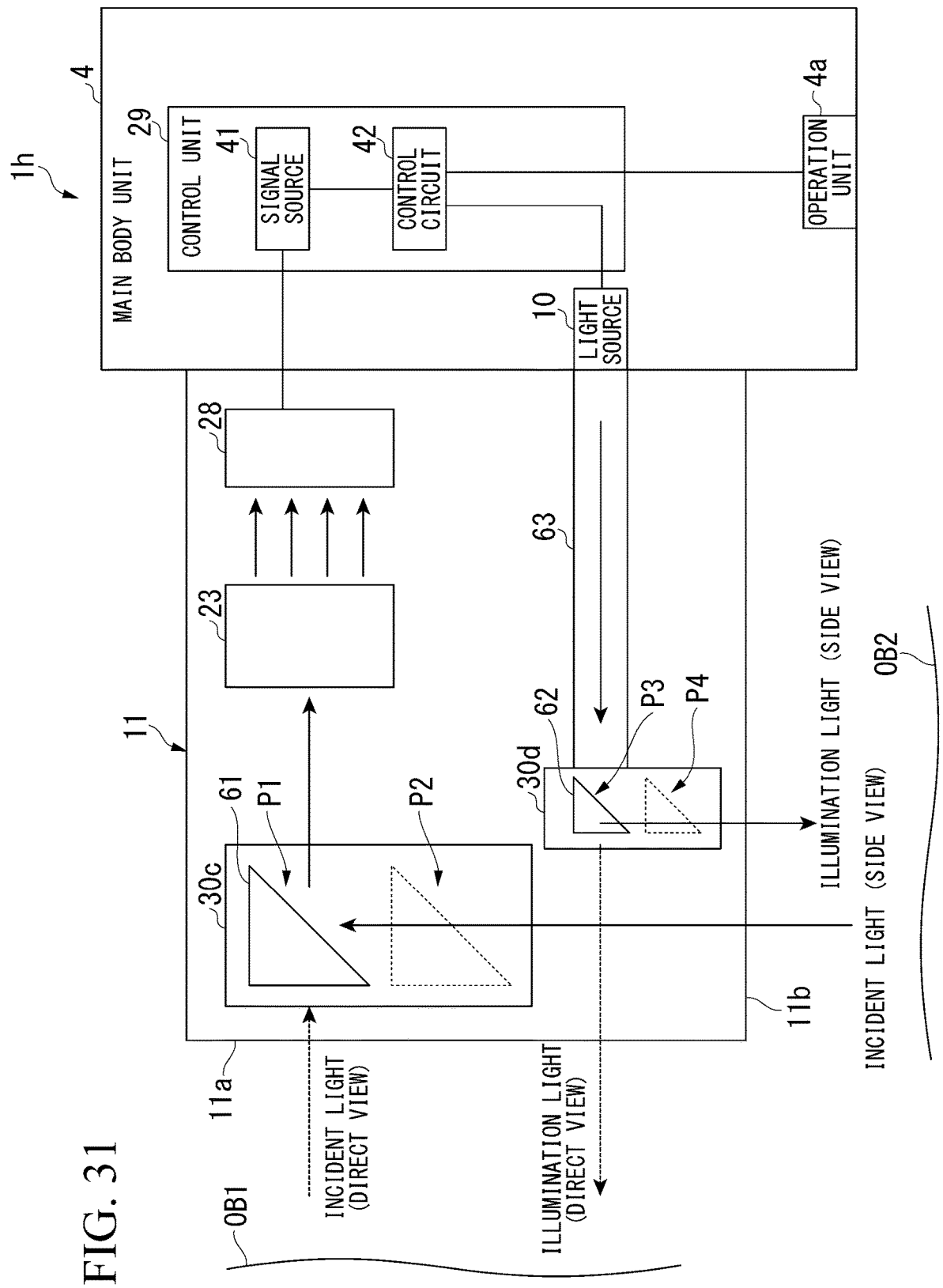
FIG. 31 is a block diagram showing a configuration of an endoscope device according to a fourth modified example of the first to seventh embodiments of the present invention.
Figure 32:
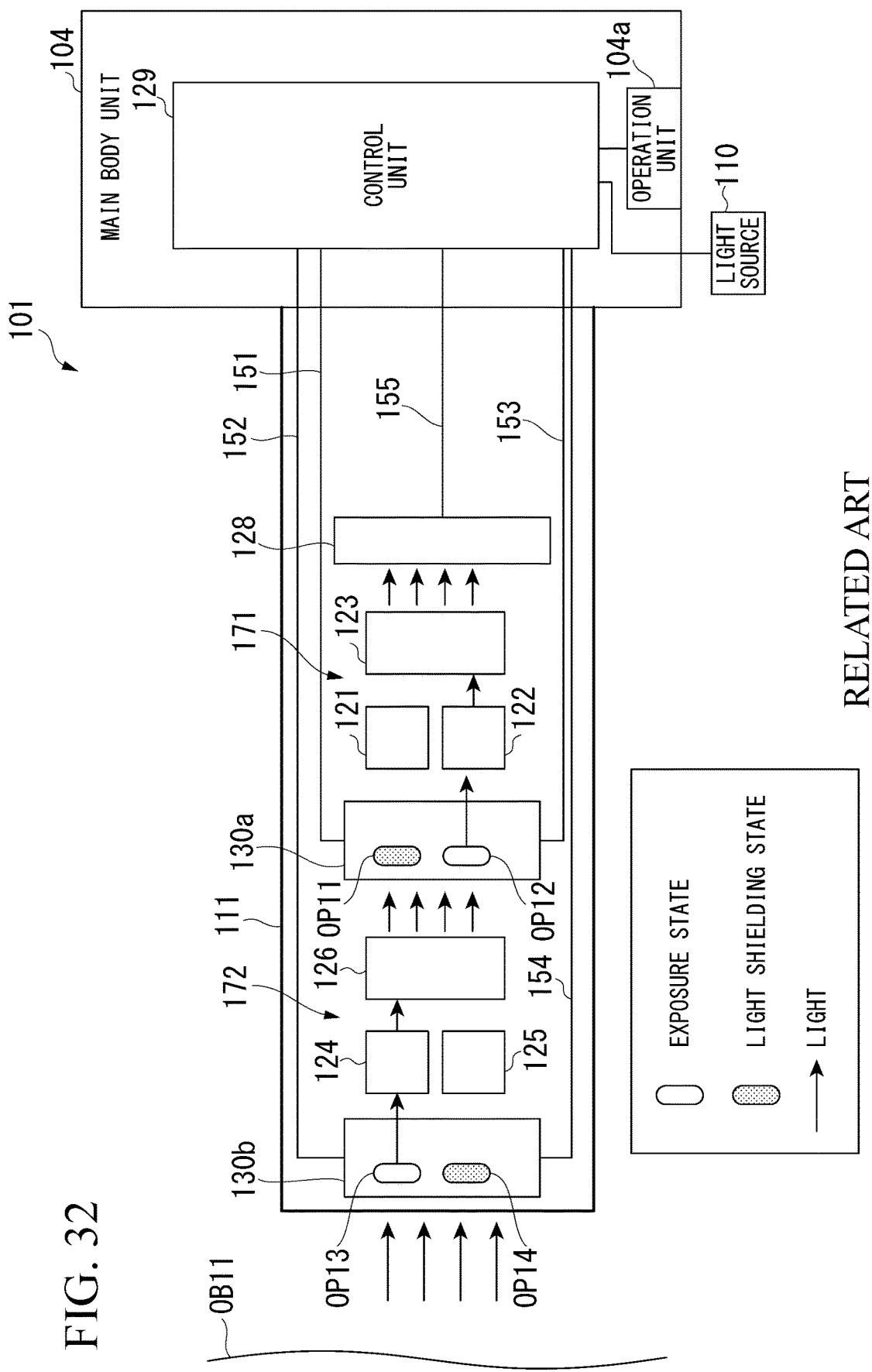
FIG. 32 is a block diagram showing a configuration of an endoscope device of related art.
Figure 33:
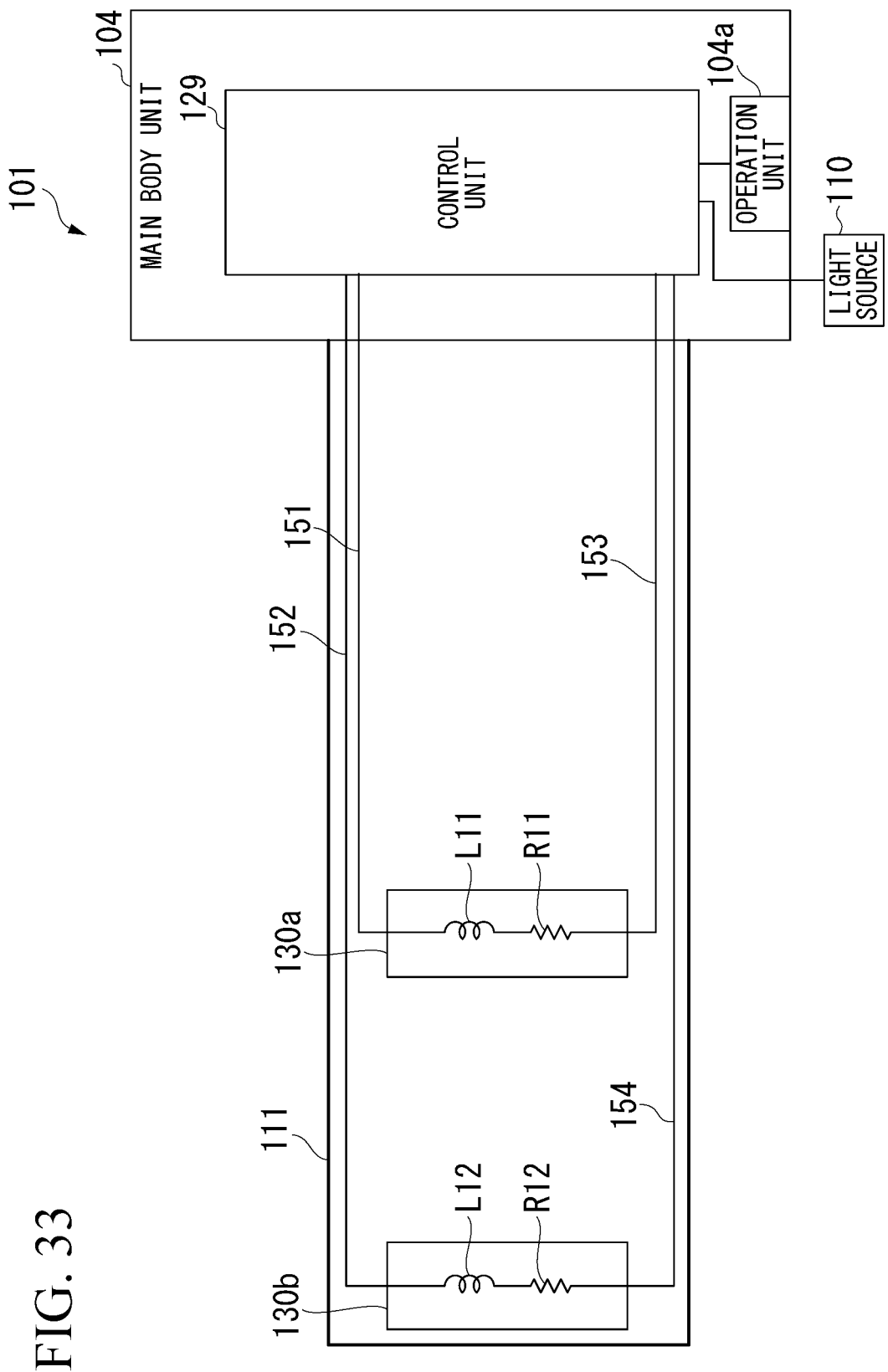
FIG. 33 is a diagram showing an equivalent circuit of actuators in the endoscope device of the related art.
Figure 34A:
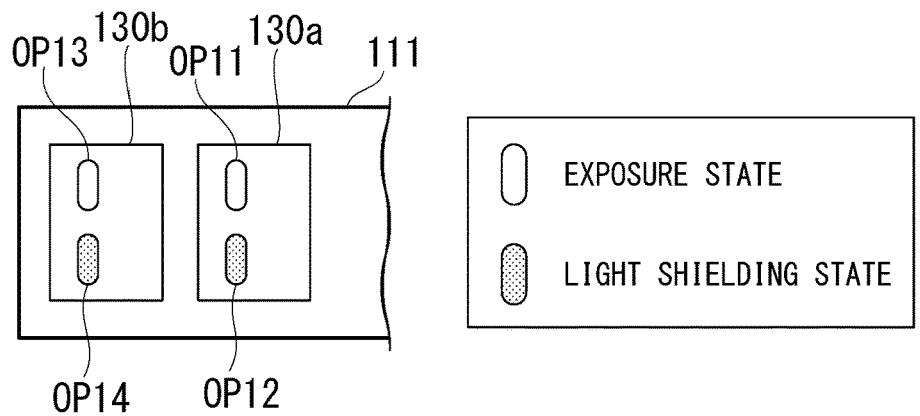
FIG. 34A is a diagram showing optical characteristics in the endoscope device of the related art.
Figure 34B:
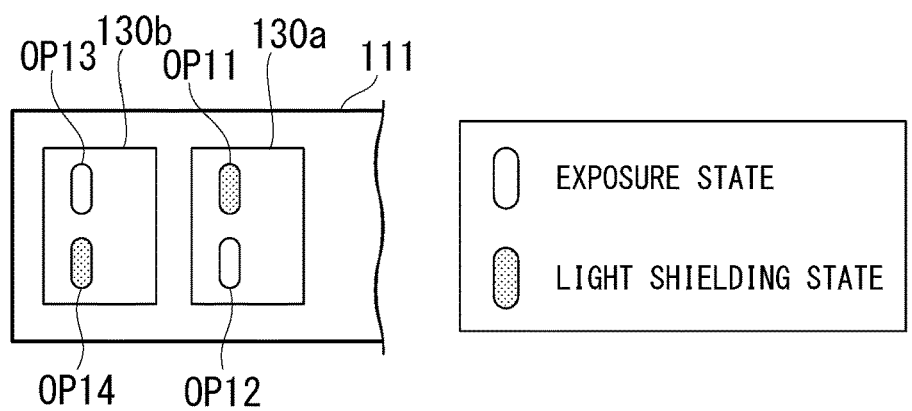
FIG. 34B is a diagram showing optical characteristics in the endoscope device of the related art.
Figure 34C:
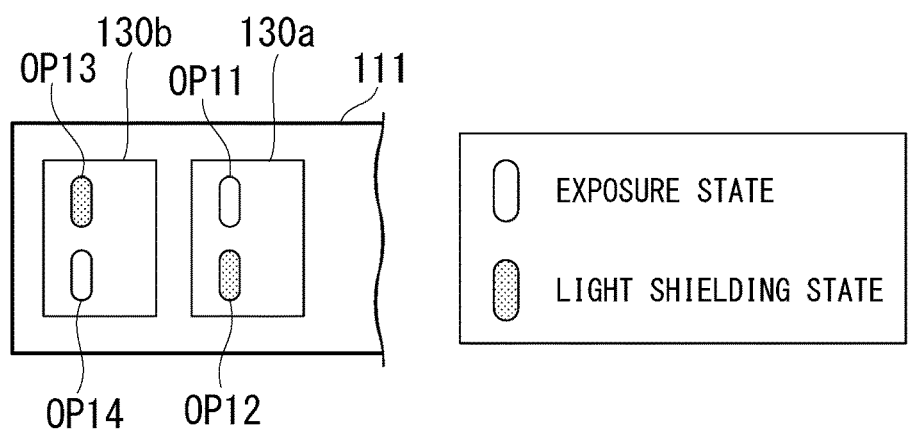
FIG. 34C is a diagram showing optical characteristics in the endoscope device of the related art.
Figure 34D:
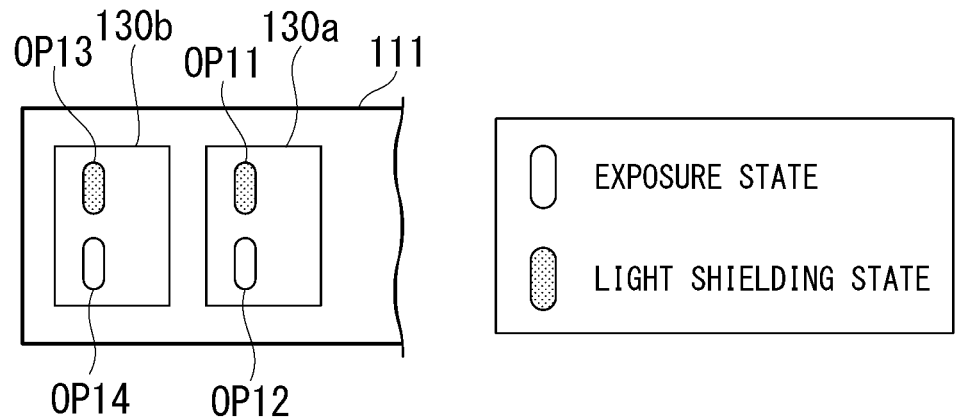
FIG. 34D is a diagram showing optical characteristics in the endoscope device of the related art.
Figure 35:
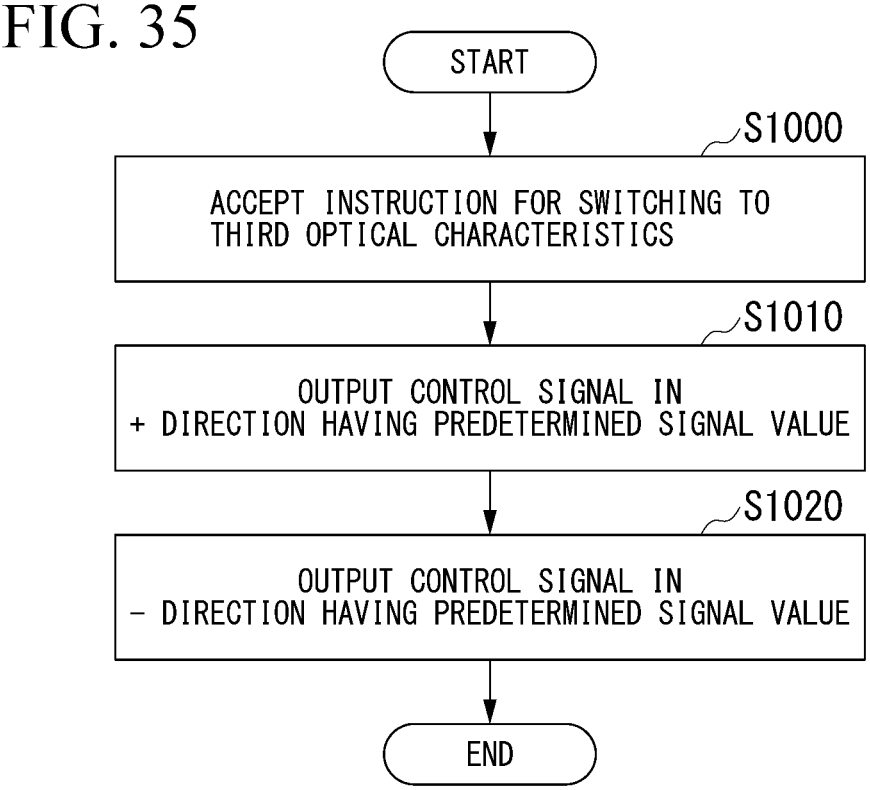
FIG. 35 is a flow chart showing a procedure of an operation of the endoscope device of the related art.
Figure 36A:
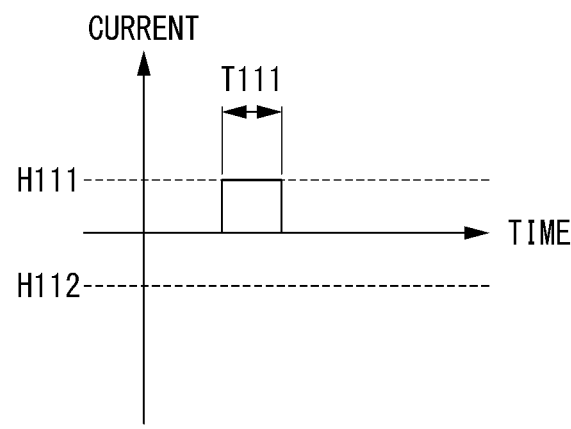
FIG. 36A is a diagram showing a waveform of a control signal applied to an actuator in the endoscope device of the related art.
Figure 36B:
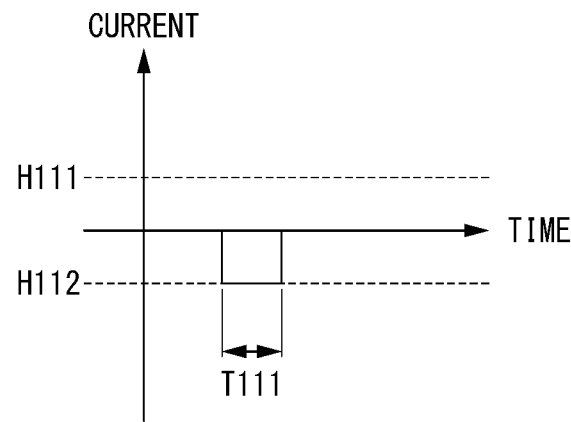
FIG. 36B is a diagram showing a waveform of a control signal applied to the actuator in the endoscope device of the related art.

FIG. 31 shows a configuration of an endoscope device 1h according to the fourth modified example of the first to seventh embodiments. In terms of the configuration shown in FIG. 31, differences from the configuration shown in FIG. 2 will be described. For convenience of illustration, the light source 10 is shown in the main body unit 4.

As shown in FIG. 31, the insertion unit 11 includes a first actuator 30c, a second actuator 30d, the optical system 23, the imaging device 28, a first prism 61, a second prism 62, and a light guide 63. An optical system of the endoscope device 1h includes an imaging optical system and an illumination optical system. The optical system 23 and the first prism 61 are optical members of the imaging optical system. The second prism 62 and the light guide 63 are optical members of the illumination optical system.

The imaging optical system is disposed between the subject OB1 and the imaging device 28 and is disposed between the subject OB2 and the imaging device 28. The subject OB1 faces a tip end surface 11a of the insertion unit 11. The subject OB2 faces a side surface 11b of the insertion unit 11. The illumination optical system is disposed between the light source 10 and the subject OB1 and is disposed between the light source 10 and the subject OB2. The position of the imaging optical system in the above description represents a position on an optical path that light to be incident to the imaging device 28 passes through. The position of the illumination optical system in the above description represents a position on an optical path that light to be emitted to the subject OB1 or the subject OB2 passes through. The imaging optical system is disposed between the tip end surface 11a of the insertion unit 11 and the imaging device 28 and is disposed between the side surface 11b of the insertion unit 11 and the imaging device 28 in the optical path that light to be incident to the imaging device 28 passes through. The illumination optical system is disposed between the light source 10 and the tip end surface 11a of the insertion unit 11 and is disposed between the light source 10 and the side surface 11b of the insertion unit 11 in the optical path that light to be emitted to the subject OB1 or the subject OB2 passes through.

The first prism 61 is able to move between a first position P1 and a second position P2. The first position P1 is a position through which light incident to the tip end surface 11a of the insertion unit 11 and light incident to the side surface 11b of the insertion unit 11 pass. The second position P2 is a position through which light incident to the side surface 11b of the insertion unit 11 passes and light incident to the tip end surface 11a of the insertion unit 11 does not pass. When the first prism 61 is disposed at the first position P1, the first prism 61 blocks light incident to the tip end surface 11a of the insertion unit 11 and reflects light incident to the side surface 11b of the insertion unit 11 toward the optical system 23. Light reflected by the first prism 61 is incident to the optical system 23. When the first prism 61 is disposed at the second position P2, the first prism 61 does not block light incident to the tip end surface 11a of the insertion unit 11. Light incident to the tip end surface 11a of the insertion unit 11 is incident to the optical system 23. When the first prism 61 is disposed at the second position P2, light incident to the side surface 11b of the insertion unit 11 is reflected by the first prism 61 without being incident to the optical system 23.

The second prism 62 is able to move between a third position P3 and a fourth position P4. The third position P3 is a position through which light passing through the light guide 63 passes. The fourth position P4 is a position through which light passing through the light guide 63 does not pass. When the second prism 62 is disposed at the third position P3, the second prism 62 reflects light passing through the light guide 63 toward the side surface 11b of the insertion unit 11. Light reflected by the second prism 62 is emitted to the subject OB2. When the second prism 62 is disposed at the fourth position P4, the second prism 62 does not block light passing through the light guide 63. Light passing through the light guide 63 is emitted to the subject OB1.

The light guide 63 is disposed through the tip end part 12, the bending part 13, and the base end part 14 of the insertion unit 11 and is disposed inside the operation unit 15, the cable 16, and the connector 17 shown in FIG. 1. The light guide 63 transmits light generated in the light source 10 to the tip end part 12 of the insertion unit 11.

The first actuator 30c moves the first prism 61 that is the first optical member between the first position P1 and the second position P2. The second actuator 30d moves the second prism 62 that is the second optical member between the third position P3 and the fourth position P4.

In terms of points other than the above, the configuration shown in FIG. 31 is similar to the configuration shown in FIG. 2.

When the first prism 61 is disposed at the first position P1 and the second prism 62 is disposed at the third position P3, light passing through the light guide 63 is emitted to the subject OB2 and light reflected by the subject OB2 is incident to the imaging device 28. For this reason, the imaging device 28 is able to acquire a side-view image.

When the first prism 61 is disposed at the second position P2 and the second prism 62 is disposed at the fourth position P4, light passing through the light guide 63 is emitted to the subject OB1 and light reflected by the subject OB1 is incident to the imaging device 28. For this reason, the imaging device 28 is able to acquire a direct-view image.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An endoscope system comprising:
   a first optical member;
   a second optical member;
   a first actuator capable of controlling the first optical member;
   a second actuator capable of controlling the second optical member; and
   a signal source configured to output a control signal to the first actuator and the second actuator,
   wherein the first actuator and the second actuator are electrically connected to the signal source,
   the first actuator is configured to move the first optical member when the control signal is applied to the first actuator,
   the second actuator is configured to move the second optical member only when the control signal having a signal value greater than or equal to a predetermined value is applied to the second actuator, and
   the signal source is configured to apply the control signal having the signal value greater than or equal to the predetermined value or the control signal having a signal value less than the predetermined value to the first actuator and is configured to apply the control signal having the signal value greater than or equal to the predetermined value to the second actuator.

2. The endoscope system according to claim 1,
   wherein the signal source is configured to apply the control signal having the signal value less than the predetermined value to the first actuator and the second actuator after the signal source applies the control signal having the signal value greater than or equal to the predetermined value to the first actuator and the second actuator.

3. The endoscope system according to claim 1,
   wherein the first actuator and the second actuator are electromagnetic actuators,
   the first optical member is a shutter or a prism,
   the second optical member is a shutter different from the first optical member in a case in which the first optical member is a shutter, and
   the second optical member is a prism different from the first optical member in a case in which the first optical member is a prism.

4. The endoscope system according to claim 1,
   wherein the first actuator includes a first coil that generates a magnetic force acting on the first optical member when the control signal is applied to the first actuator, the second actuator includes a second coil that generates a magnetic force acting on the second optical member when the control signal is applied to the second actuator, and a number of turns of the first coil is greater than a number of turns of the second coil.

5. The endoscope system according to claim 1, wherein the first actuator includes a first permanent magnet fixed to the first optical member, the second actuator includes a second permanent magnet fixed to the second optical member, and a magnetic force of the first optical member is stronger than a magnetic force of the second permanent magnet.

6. The endoscope system according to claim 1, wherein the first actuator includes:

a first magnetic substance; and a first coil wound around the first magnetic substance and configured to cause the first magnetic substance to be magnetized when the control signal is applied to the first actuator, the second actuator includes:

a second magnetic substance; and a second coil wound around the second magnetic substance and configured to cause the second magnetic substance to be magnetized when the control signal is applied to the second actuator, and a magnetic force generated in the first magnetic substance when the first magnetic substance is magnetized is stronger than a magnetic force generated in the second magnetic substance when the second magnetic substance is magnetized.

7. The endoscope system according to claim 1, further comprising a signal line connecting the first actuator and the second actuator to the signal source, wherein the first actuator and the second actuator are connected in parallel to the signal line, and the second actuator includes a resistor electrically connected to the signal line.

8. The endoscope system according to claim 1, further comprising:

a resistor; and a signal line connecting the first actuator and the second actuator to the signal source, wherein the first actuator and the second actuator are connected in parallel to the signal line, and the resistor is connected in series to the second actuator and electrically connected to the signal line.

9. The endoscope system according to claim 1, further comprising:

a signal line connecting the first actuator and the second actuator to the signal source;

a first resistor; and a second resistor, wherein the first actuator and the second actuator are connected in parallel to the signal line, the first resistor is connected in series to the first actuator and electrically connected to the signal line, and the second resistor is connected in series to the second actuator and electrically connected to the signal line.

10. The endoscope system according to claim 1, wherein, the first actuator is configured to move the first optical member when the control signal is continuously applied to the first actuator for longer than or equal to a first application duration, the second actuator is configured to move the second optical member only when the control signal having the signal value greater than or equal to the predetermined value is continuously applied to the second actuator for longer than or equal to a second application duration, the first application duration is longer than the second application duration, the signal source is configured to continuously apply the control signal having the signal value greater than or equal to the predetermined value to the first actuator and the second actuator for longer than or equal to the second application duration and shorter than the first application duration, and the signal source is configured to continuously apply the control signal having the signal value less than the predetermined value to the first actuator and the second actuator for longer than or equal to the first application duration.

11. The endoscope system according to claim 10, wherein a timing at which the control signal having the signal value greater than or equal to the predetermined value is applied to the first actuator and the second actuator is different from a timing at which the control signal having the signal value less than the predetermined value is applied to the first actuator and the second actuator.

12. The endoscope system according to claim 10, wherein the first actuator and the second actuator are electromagnetic actuators, the first optical member is a shutter, the second optical member is a shutter different from the first optical member.

13. The endoscope system according to claim 10, wherein the first optical member is heavier than the second optical member.

14. The endoscope system according to claim 10, further comprising:

a condenser; and a signal line connecting the first actuator and the second actuator to the signal source, wherein the first actuator and the second actuator are connected in series to each other, and the condenser is connected to the signal line in parallel with the first actuator.

15. The endoscope system according to claim 10, further comprising:

a detector configured to detect positions of the first optical member and the second optical member; and a control circuit configured to control the signal source such that a state of the endoscope system becomes any one of a first state and a second state on the basis of the positions detected by the detector, wherein, the first state is a state in which the control signal having the signal value less than the predetermined value is continuously applied to the first actuator and the second actuator for longer than or equal to the first application duration, and the second state is a state in which the control signal having the signal value greater than or equal to the predetermined value is continuously applied to the first actuator and the second actuator for longer than or equal to the second application duration and shorter than the first application duration.

16. An optical adaptor for an endoscope, the optical adaptor comprising:

a first optical member;

a second optical member;

a first actuator configured to operate when a control signal having a predetermined signal value is applied to the first actuator and configured to move the first optical member; and
a second actuator configured to operate only when a control signal having a signal value greater than the predetermined signal value is applied to the second actuator and configured to move the second optical member,
wherein the first actuator and the second actuator are electrically connected to each other.

17. The optical adaptor according to claim 16,
wherein, the first actuator is configured to move the first optical member when the control signal having the predetermined signal value is continuously applied to the first actuator for longer than or equal to a first application duration,
the second actuator is configured to move the second optical member only when the control signal having the signal value greater than or equal to the predetermined signal value is continuously applied to the second actuator for longer than or equal to a second application duration, and
the first application duration is longer than the second application duration.

18. A method of controlling an endoscope system, the method comprising:
a first step; and
a second step,
wherein the endoscope system includes:
a first optical member;
a second optical member;
a first actuator capable of controlling the first optical member;
a second actuator capable of controlling the second optical member; and
a signal source configured to output a control signal to the first actuator and the second actuator,
the first actuator and the second actuator are electrically connected to the signal source,
the first actuator is configured to move the first optical member when the control signal is applied to the first actuator,
the second actuator is configured to move the second optical member only when the control signal having a signal value greater than or equal to a predetermined value is applied to the second actuator,
the signal source is configured to apply the control signal having the signal value greater than or equal to the predetermined value or the control signal having a signal value less than the predetermined value to the first actuator in the first step, and
the signal source is configured to apply the control signal having the signal value greater than or equal to the predetermined value to the second actuator in the second step.

* * * * *